(12) United States Patent
Ahrens et al.

(10) Patent No.: US 7,659,448 B2
(45) Date of Patent: Feb. 9, 2010

(54) PLANT REGULATORY SEQUENCES FOR SELECTIVE CONTROL OF GENE EXPRESSION

(75) Inventors: Jeffrey Ahrens, Manchester, MO (US); Jill Deikman, Davis, CA (US); Philip Miller, Ballwin, MO (US); Ming Peng, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 634 days.

(21) Appl. No.: 10/827,659

(22) Filed: Apr. 19, 2004

(65) Prior Publication Data

US 2005/0235382 A1 Oct. 20, 2005

Related U.S. Application Data

(60) Provisional application No. 60/463,974, filed on Apr. 18, 2003, provisional application No. 60/530,725, filed on Dec. 18, 2003.

(51) Int. Cl.
| | |
|---|---|
| *A01H 5/00* | (2006.01) |
| *C12N 15/82* | (2006.01) |
| *C12N 15/87* | (2006.01) |
| *C12N 5/14* | (2006.01) |
| *C12N 15/63* | (2006.01) |
| *C07H 21/04* | (2006.01) |

(52) U.S. Cl. .................. 800/295; 800/278; 800/279; 800/312; 800/317.3; 800/317.4; 800/320; 800/320.1; 800/320.2; 800/320.3; 435/320.1; 435/419; 435/468; 536/24.1

(58) Field of Classification Search ................ None
See application file for complete search history.

(56) References Cited

U.S. PATENT DOCUMENTS

| 6,084,089 A * | 7/2000 | Mine et al. ................. 536/24.1 |
| 2005/0160500 A1 | 7/2005 | Castigioni et al. ........... 800/288 |
| 2005/0235377 A1 | 10/2005 | Dasgupta et al. ............ 800/280 |

OTHER PUBLICATIONS

Kim et al. (Plant Molecular Biology, 24:105-117, 1994).*
Benfey et al. (Science 250:959-966,1990).*
Database Genbank, Database Accession No. AF031235, 1998.
Database Genbank, Database Accession No. AJ310994, 2001.
Database Genbank, Database Accession No. D13044, 2004.
Database Genbank, Database Accession No. D26563, 1999.
Database Genbank, Database Accession No. U01377, 1997.
Database Genbank, Database Accession No. U14665, 1995.
Database Genbank, Database Accession No. U63993, 1996.
Lorkovic et al., "Pre-mRNA splicing in higher plants," *Trends in Plant Sciences*, 5:160-167, 2000.
Shinozaki et al., "Molecular responses to dehydration and low temperature: differences and cross-talk between two stress signaling pathways," *Current Opinions in Plant Biology*, 3(3):217, 2000.

* cited by examiner

*Primary Examiner*—Vinod Kumar
(74) *Attorney, Agent, or Firm*—Erin C. Robert, Esq.; Sonnenschein Nath & Rosenthal LLP

(57) ABSTRACT

The current invention relates to enhancing gene expression in a plant during abiotic stress. More specifically the invention relates to a promoter that could be used to drive the expression of structural genes or other DNA sequences. We disclose the sequence of the promoter and give examples showing the function of the promoter.

28 Claims, 24 Drawing Sheets

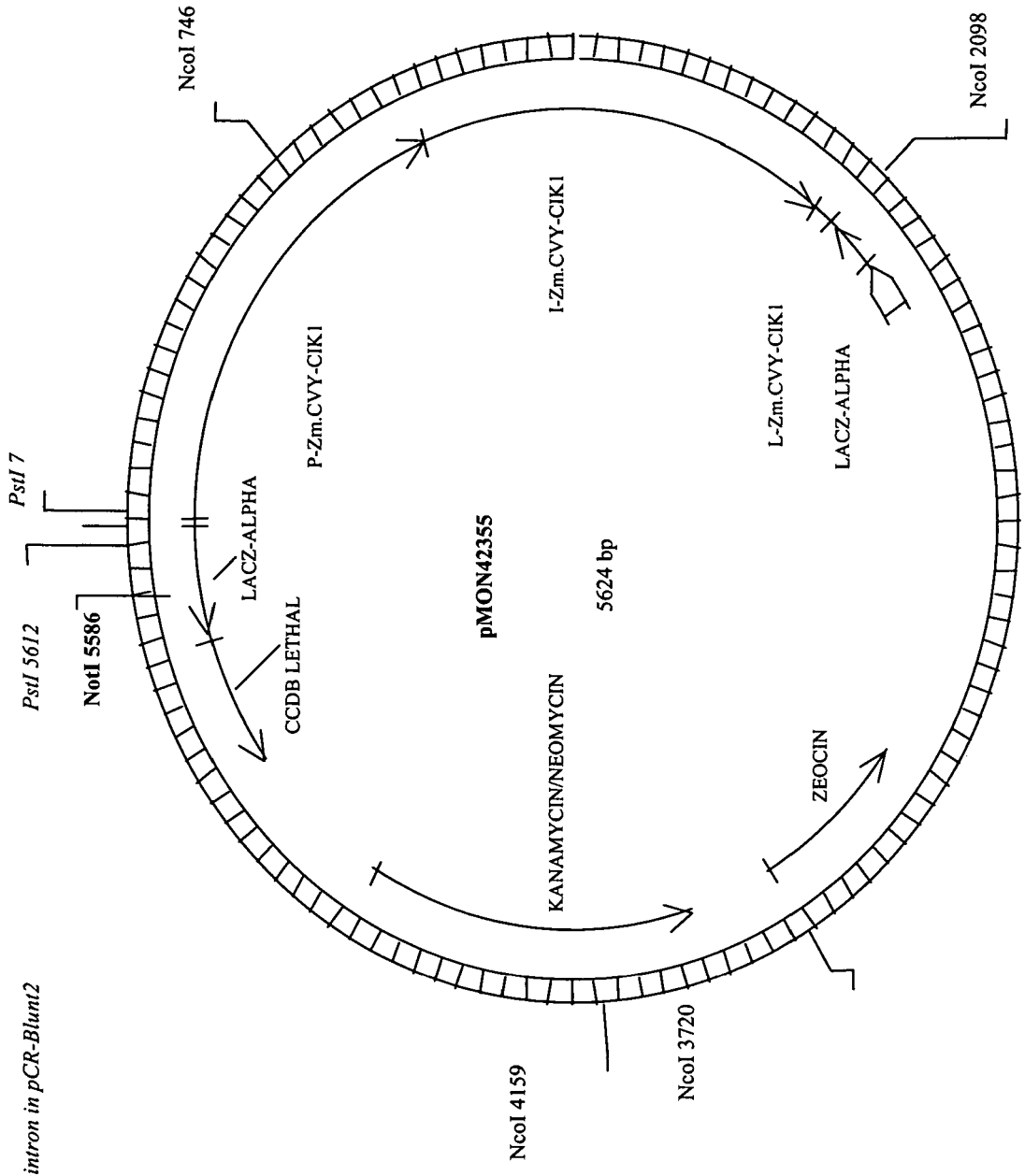
Figure 1. *P-CVY-CIK1+intron in pCR-Blunt2*

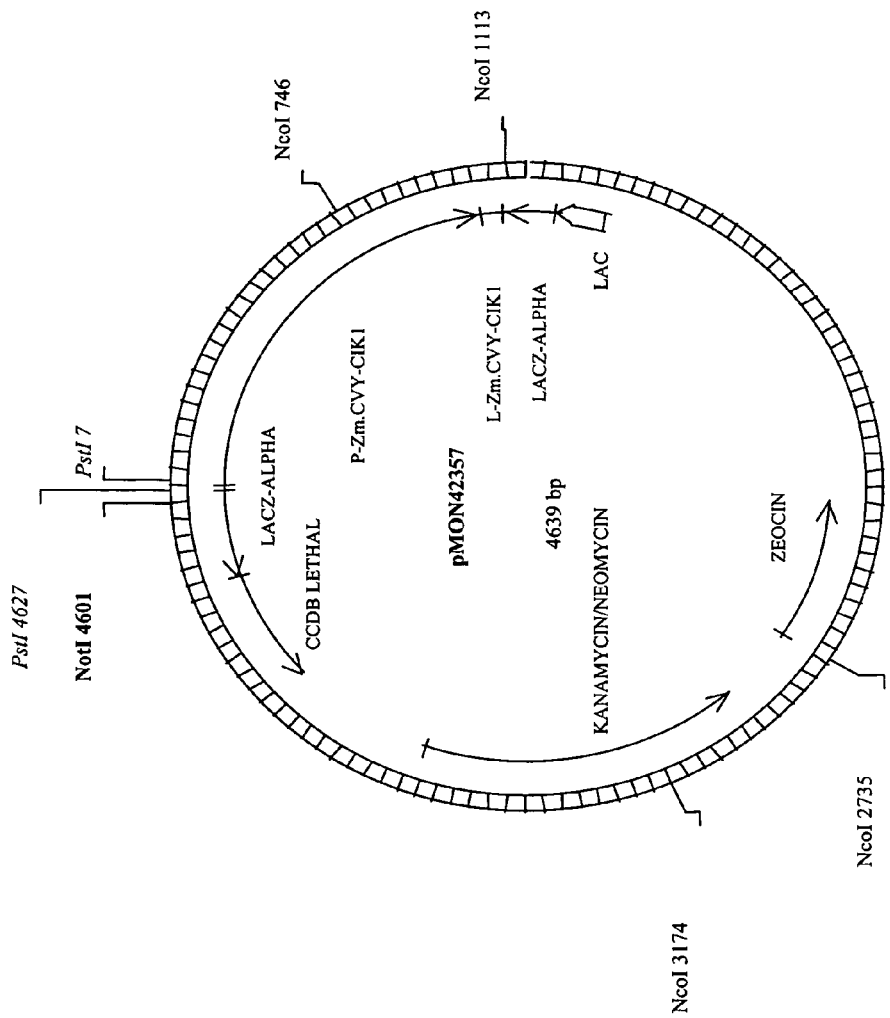
Figure 2. *P-CVY-CIK1 w/o intron in pCR-BluntII*

Figure 3.

```
   1 ATCCACGCTC GCTCGGGTGT CGGGTCAGAT CGATCCAGTT GGGCACGTA ATAATCCTTT
  61 TCCCCAGAAG GAGTGGAACC CCTCCTCCCC GTCCAATCCA ATCAAAGCGA CCAATCGACT
 121 GGCTGTCCTA CACACACACA AAACGACCCG AGGCGACACA CCGCAGCAGT GATCATTCTG
 181 AGCATTTGCA GAAAAAGGAG AACGTCCCGA AATCCTGGTG GTTGTATTGT GTGATTGCTC
 241 ACTCAGTCCG TGCAGGGTCA GGGTGAAGCC AAGCCAACAA CCCAACGCTC GCTGGGAGTA
 301 GGGTCCACCG GATTTATTGG CAGTACATCG CTGTTTGGTC CTCCTGCCCT TCGCTTATTT
 361 TTTAATTCGG CAGACGTGCA CAGACAGGGC ACCACCGGAC CAAGGAAGGG CGCACACCGT
 421 CGTCAGTCAC CAGGTGGGTG TGATCAGCAG CCGCTTCTCT TGTGCTGCTT TATAGCGTAT
 481 GAAATTCCAG TGTCCCTGTT CCACCTGCAT GCAATTGGTT TGACTGAACA ACATGATAGC
 541 AAGTGATACT ATATATATTT TTATAGAGGA ACACAGTGAA AAAATATTTA GTATTATTAC
 601 GTGCATGAAA TTGTATTCAC AGTTATCCCT GATGCAACGC AATTGTTCAA TATATAGCAG
 661 TATATATTAT ACGAAGTATA TATGTATATC TAATTTTATG AGACCGGGAG AAGGTGTATT
 721 CACAGTACAG TGCAGGGCCA TGGCCATGCA GCCCTTGGGG CCTGAAAAGG GTCGCGTGAA
 781 GTGGCCAACG CTGTGCAATT GCAACCAAAC AAACTTTTGG TGGCGGGGTC CCTGTCCCTG
 841 GCCGGCTTTG CCCACAGGCC ACAGCGCATC ACACACCGC TTTATAGCGC CACCCCACCA
 901 CCCTCGTCTC TCCCCCCGTC GAGCACACAA CACACCCTCC TCGTCCTCCA ATCCAATCAA
 961 CCTGGTAGAC TCGCTTCGCT TCTCCCCCCA GCTCGGACGG AGCTCCTCGC AGCAGCCGCC
1021 GATCAACCTG CGCTCGGGCT CAGGCTGGA AGgtgagagc tcagtgcctc gtcccgcccg
1081 cccaaatct ggttcttgtg ctggctctgg ctgtcgctg cacgaattct gcatctgtt
1141 ctttcgagac gcaattcccg gaccgtgggc tttggtttcg gagggggccg agagtaaggc
1201 gttaggactt tctccgagct gcaaggccgc tcgtcgttgc ggcatttttc gtttcgcttg
1261 tcctgtgatg agagatgtgc atttccctt ggcgggctta ccgttccctg ctcgtctgta
1321 tgtgtgtatg tttgtgtgac cttttcccca agccaggct gcgcctttct cttgctgttt
1381 ctttcagcag tacagacgcg catctgtaca ggccttttt tcggtcctgg gttatgattg
1441 atccgttaac agttggtcac ctgcctatac caagtgctgg ctgtttaata tgtactataa gcttcttggt
1501 gccgctgcct ctgcctatac gactttatgc gctgcctgca caagtctcag ccatctgtgg
1561 gaacgtgtgt ctctcaccta ccttcatat tgcactagct ggattgaatc attctgctt
1621 ggagagatgt ccggtcattt cggtcacta catttcatc tcgcgtacta gttttgttt
1681 tgttttgcga gagagtaatt atttccctt tttttttaat atttactgtc tcctgtccca tttgctgttt
1741 ctttacccag aaatttccac cagattcagt caaacgaaac tcctgtgctc tttttttct
1801 cccttcaaa agggtgtgta accgactacc gactcagata atataagtgc ggtcacatat
1861 cacatgatat catctcgcct ctctccttc tcctgtgttt tatttttctt tttctaacc
1921 acagcgtgat gaacttcttt tttttttggg gggggggg aacggctggt tcactgaaca cagcttagcg
1981 aacatgaatg ggtagtttta caactaatgc ttttttta ggggtaacta actgtagGTG
2041 TTGAAGAGA ATAGCCTGAA GGTTCACAGT AACCTTCATC TGTCGGAAGC C
```

Figure 5. *P-CVY-CIK1 pro in 32502 (no introns)*

Figure 7.   corr. CIK1-GUS (no intron)

Figure 8.  corr. *CIK1-rACT-GUS*

Figure 9.  p-CVY-CIK1 (w/intron) in 32502

Figure 10. *pCIK1::iCIK1::GUS in agro vector*

PLANT REGULATORY SEQUENCES FOR SELECTIVE CONTROL OF GENE EXPRESSION

CROSS REFERENCE TO RELATED APPLICATIONS

This application claims benefit under 35 USC §119(e) of U.S. provisional application Ser. No. 60/463,974 filed Apr. 18, 2003 and U.S. application Ser. No. 60/530,725 filed Dec. 18, 2003, both of which are herein incorporated by reference.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named CVY-CIK1-ST25.txt, which is 49,152 bytes and was created on Apr. 19, 2004, are hereby incorporated by reference.

FIELD OF THE INVENTION

The present invention relates to the isolation and use of nucleic acid molecules for control of gene expression in plants, specifically novel plant promoters, and derivatives thereof. More specifically the invention relates to promoters used to enhance expression of a gene during abiotic stress, including cold stress.

BACKGROUND OF THE INVENTION

One of the goals of plant genetic engineering is to produce plants with agronomically important characteristics or traits. Recent advances in genetic engineering have provided the requisite tools to transform plants to contain and express foreign genes (Kahl et al. (1995) World Journal of Microbiology and Biotechnology 11:449-460). Particularly desirable traits or qualities of interest for plant genetic engineering would include, but are not limited to, resistance to insects and other pests and disease-causing agents, tolerances to herbicides, enhanced stability, yield, or shelf-life, environmental tolerances, and nutritional enhancements. The technological advances in plant transformation and regeneration have enabled researchers to take pieces of DNA, such as a gene or genes and incorporate the exogenous DNA into the plant's genome. The gene or gene(s) can then be expressed in the plant cell to exhibit the added characteristic(s) or trait(s).

Promoters are regulatory elements that play an integral part in the overall expression of a gene or gene(s). It is advantageous to have a variety of promoters to tailor gene expression such that a gene or gene(s) is transcribed efficiently at the correct time during plant growth and development, in a location in the plant, and/or in the amount necessary to produce the desired effect. In one case, for example, constitutive expression of a gene product may be beneficial in one location of the plant, but less beneficial in another part of the plant. In other cases, it may be beneficial to have a gene product produced at a certain developmental stage of the plant, or in response to certain environmental or chemical stimuli. The commercial development of genetically improved germplasm has also advanced to the stage of introducing multiple traits into crop plants, also known as a gene stacking approach. In this approach, multiple genes conferring different characteristics of interest can be introduced into a plant. It is important when introducing multiple genes into a plant, that each gene is modulated or controlled for expression and that the regulatory elements are diverse, to reduce the potential of gene silencing which can be caused by processes including but not limited to recombination or methylation of homologous sequences. In light of these and other considerations, it is apparent that control of gene expression and regulatory element diversity are important in plant biotechnology.

Therefore a need exists for promoters that have been shown to direct the transcription of genes during stressful conditions. A promoter that upregulates endogenous gene expression when the plant within which it resides was placed in a stressful condition could be used to drive heterologous genes from a number of different pathways, including but not limited to signaling molecules, transcription factors, or enzymes that could provide tolerance to the stresses that induced transcription from the endogenous promoter, or other genes. This upregulation of genes could lead to better yield through enhancement of the transgenic plant's tolerance for stress.

SUMMARY OF THE INVENTION

The present invention provides an isolated promoter sequence capable of modulating or initiating transcription of a DNA sequence to which it is operably linked. The isolated promoter sequences can be used to create recombinant DNA molecules for selectively modulating expression of any operatively linked gene and provide additional regulatory element diversity in a plant expression vector in single gene or gene stacking approaches. Moreover, isolated plant promoter sequences that comprise nucleic acid polynucleotides are provided. These isolated promoter sequences have the biological activity of expressing operably linked nucleic acid molecules when the plant is exposed to a stressful environment.

The present invention further provides nucleic acid molecules comprising a DNA polynucleotide sequence set forth in SEQ ID NO: 1, 14-18, or any fragments, regions, or cis elements (motifs) of the sequence that are capable of regulating transcription of an operably linked DNA. Transcription could occur in a plant cell. Transcription could be directed in a plant cell exposed to a plant stress environment, including cold stress, and their use therefore. The present invention also relates to the use of at least one fragment, region, or cis element (motif) of SEQ ID NO: 1, 14-18, that alone or combined with other nucleic acids creates a chimeric promoter capable of initiating and/or modulating transcription of an operably linked DNA sequence.

A still further aspect of the present invention relates to full length, truncation, or deletion derivatives 45% to 100% identical and or hybridize to SEQ ID NO: 1, 14-18, that are capable of functioning in a plant cell to modulate or initiate transcription of an operably linked DNA sequence in a plant, and methods of their isolation, and recombinant DNA molecules comprising SEQ ID NOs: 1, 14-18.

In a further embodiment of the present invention, plants, plant cells, tissues, seeds, or plant parts containing a heterologous or chimeric DNA construct containing a promoter of the present invention stably integrated within the plant genome is provided. Fertile transgenic plants containing a recombinant DNA molecule comprising SEQ ID NO: 1, 14-18, or any fragment, region, or cis element of SEQ ID NO: 1, 14-18, as a regulatory element initiating transcription of an operably linked heterologous DNA sequence stably integrated into the plant's genome are also provided herein. The fertile transgenic plants monocot or dicot plants could include, but are not limited to, corn, wheat, rye, rice, oat, barley, turfgrass, sorghum, millet, sugarcane, millet, sugarcane, tobacco, tomato, potato, soybean, cotton, canola, alfalfa, sunflower, strawberry, and cotton.

The invention provides transgenic plants comprising a promoter of the present invention that upregulates transcription in stressful or other condition transcribing and/or modulating the transcription of an operably linked heterologous DNA sequence in a plant. Also provided is a transgenic plant of the present invention that has increased yield or increased tolerance to stressful characteristics as a result of the heterologous expression of a selected DNA sequence in a plant through use of the promoter sequences of the present invention. The invention also contemplates transcription of polynucleotides by the disclosed promoter that could affect any phenotype in a plant, including but not limited to, cold tolerance, disease resistance, abiotic stress tolerance, enhanced cold tolerance, enhanced salt tolerance, enhanced cold germination, enhanced drought tolerance, enhanced freezing tolerance, enhanced biotic stress tolerance, insect resistance, herbicide tolerance, and/or yield.

The invention includes promoters that function in plants that include, or are produced, from, motifs included herein (for example Tables 9, 10, and 11).

The foregoing and other aspects of the present invention will become apparent from the following detailed description and accompanying drawings and sequence listings.

BRIEF DESCRIPTION OF THE DRAWINGS

FIG. 1. Shown is a map of plasmid pMON42355.

FIG. 2. Shown is a map of plasmid pMON42357.

FIG. 3. Illustrates the sequence of CVY-CIK1 promoter, intron, and 5'UTR; SEQ ID NO:1. The 5'UTR was determined from EST clones. 5'UTR, identified initially in cDNA clones for CVY-CIK1, are underlined. An intron was identified when the promoter was cloned from genomic DNA (intron indicated in lower case letters).

A. Five-day-old LH172plants. Lanes labeled "Shoot-25" and "Root-25" are control plants grown in the dark for five days at 25 degrees C. Lanes labeled "shoot 25-4" and "root 25-4" were grown in the dark for four days at 25 degrees C., then transferred to 4 degrees C. for 24 hours.

B. These lanes contain RNA from root and shoots of LH320 seedlings grown for approx. five days at 25 degrees C. in the dark, then transferred to 10 degrees C. for the times listed (e.g. 2H=2 hours) before harvest ("R"=root RNA, "S"=shoot RNA).

C. RNA in these lanes is from callus tissue at various stages during the transformation process (the callus used for this tissue was being transformed with pMON30113, a construct containing a 35S::NPTII cassette and a 35S::GFP cassette as a control).

D. RNA from LH320 seedlings grown in the dark for approximately four days at 25 degrees C., then shocked at the temperatures listed for approximately 21 hours before harvest.

E. RNA from LH320 plants grown for 20 days at 25 degrees C. under 12 hour light/dark conditions. Lanes marked "leaf-25" and "root-25" were harvested after 20 days. Lanes marked "leaf 25-40" and "root 25-40" were transferred to 40 degrees C. temperatures for an additional 22 hours as a heat shock before harvest.

F. RNA from several leaves of a V18 stage C corn plant. This plant was a non-transformed LH320 plant growing in the greenhouse. This RNA was used to determine if this gene was expressing in leaves of older plants (tassel was present on this plant).

G. RNA from LH172 plants grown for 21 days at 25 degrees C. RNA was harvested from non-shocked plants ("leaf-3 wk") and plants shocked at 13 degrees C. for approximately 22 hours before harvesting.

H. RNA from LH 172 plants grown in the field as a part of a drought screen. RNA was isolated from leaves of plants that were well watered ("leaf—con") and leaves of plants under drought stress ("leaf—dry").

Figure 12:
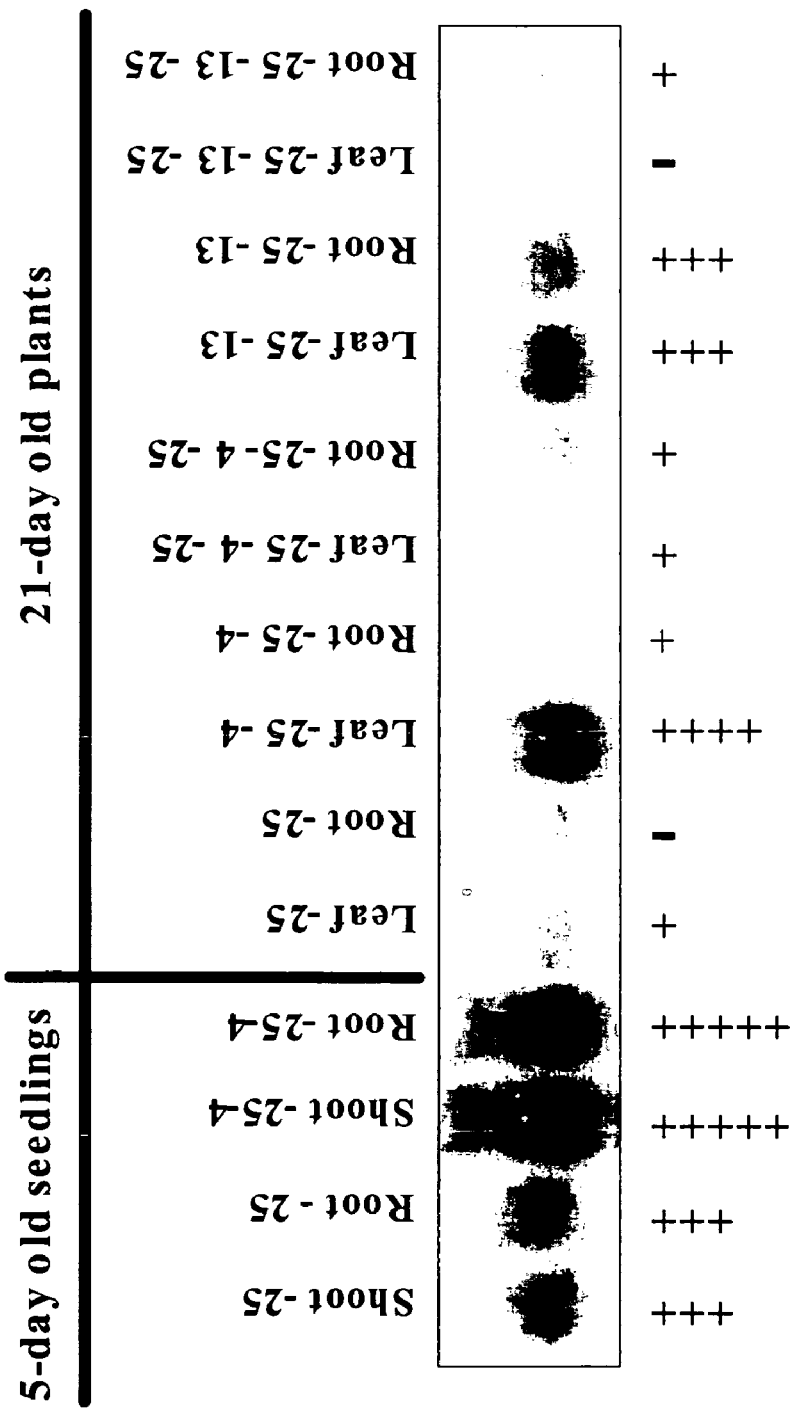

FIG. 12. The tissue treatments for each RNA sample are described. Briefly, the label "leaf-25-4-25" indicates that this lane contains leaf tissue grown for 21 days at 25 degrees C., shifted to 4 degrees C. for 22 hours, and returned to 25 degrees C. for 6 hours. All the other lanes follow this labeling pattern (grown at 25 degrees C., shocked at x C for 22 hours, then returned to 25 degrees C. or not for 6 hours after shock). The 5-day-old seedling tissue was grown for 5 days at 25 degrees C. in the dark and frozen (control). The cold shocked tissue was grown for four days at 25 degrees C., then shifted to 4 degrees C. for 25 hours and then frozen. Below each lane in the figure is an evaluation of the relative expression level in each sample ("−" indicates little or no expression, "+" indicates very low levels of expression, and increasing numbers of "+" symbols indicate increasing levels of expression of this gene).

Figure 13:
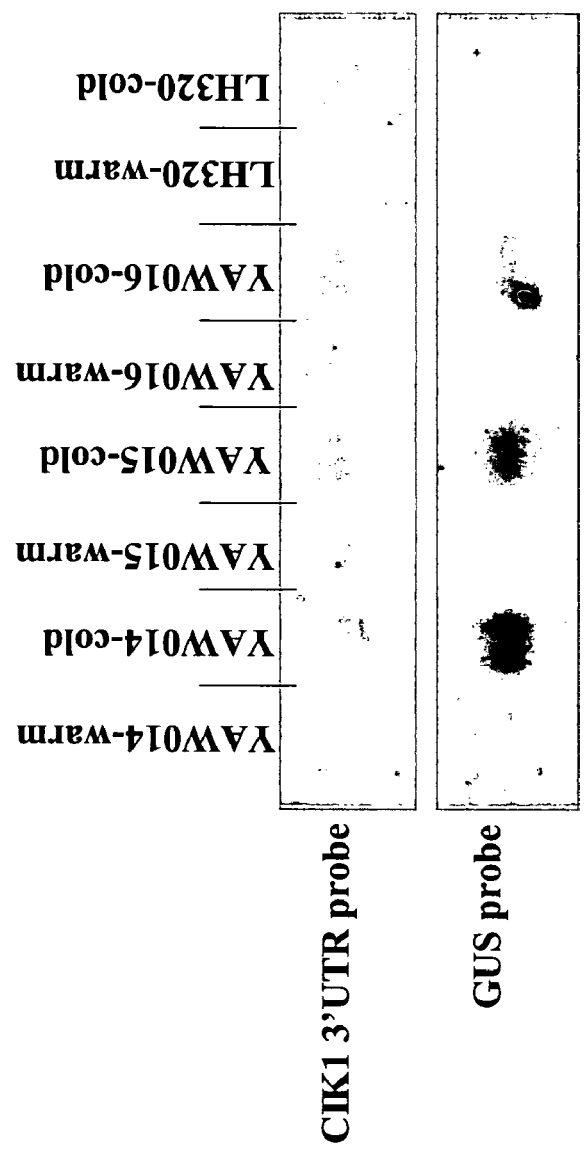

FIG. 13. Leaf samples from three separate R0 events for the event YAW (transformed with pMON42360) were sampled and treated for 17 hours at either 13 degrees C. or 30 degrees C. Two identical RNA blots were made with the isolated RNA. The upper blot was hybridized with a probe made against the endogenous CVY-CIK1 3'UTR (to determine the expression pattern of the endogenous CVY-CIK1 gene), while the lower blot was hybridized with a probe made against the GUS reporter gene (to determine the expression of the cloned CVY-CIK1 promoter).

Figure 14:
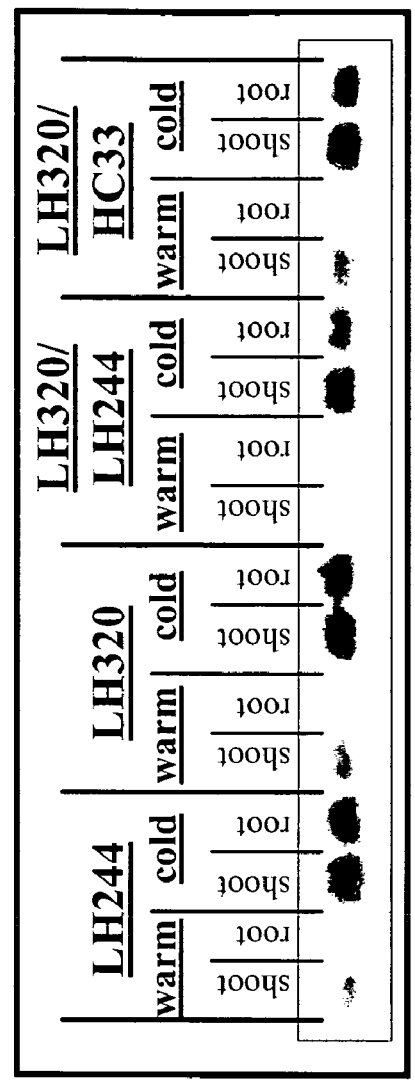

FIG. 14. RNA was isolated from inbreds (LH244 and LH320) and hybrids (LH320/LH244 and LH320/HC33) which were grown for 4 days at 25 degrees C. in the dark, then shifted to 10 degrees C. (cold) or left at 25 degrees C. (warm) for an additional 23 hours. The blot was hybridized with a DIG-labeled probe for the CVY-CIK1 3'UTR and exposed to film for one minute.

Figure 15:
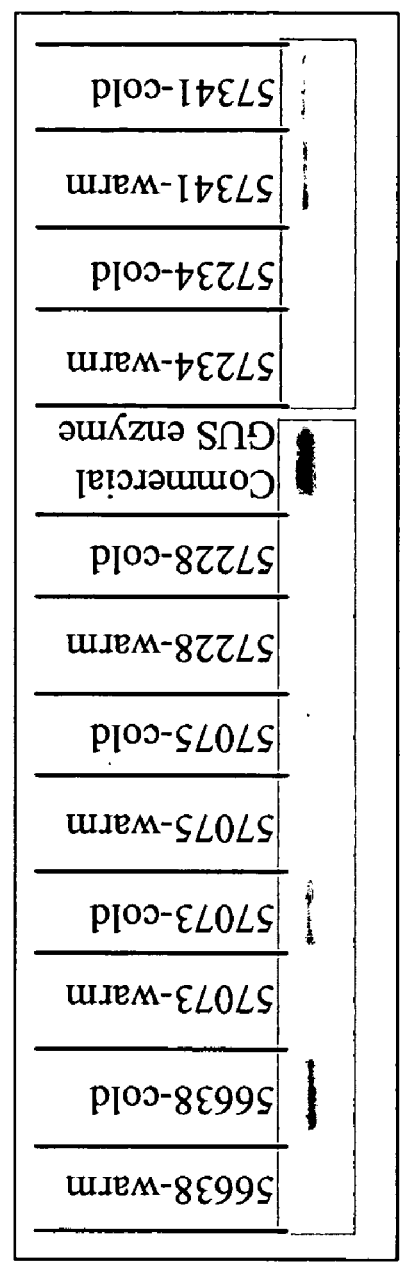

FIG. 15. This Western blot was performed with protein extracted from 4 day old shoot tissue. Warm and cold treatments of the plants are described in the text. The bands shown here for each event run at the expected size for the GUS protein (approximately 66 kDa). 30 ug of protein was used in each lane. Three events (Zm_S 56638, Zm_S 57073, and Zm_S 57075) show a clear increase in the level of GUS protein in the cold treated samples. One event (Zm_S 57234) shows a slight increase in the level of GUS protein in response to cold. Two events (Zm_S 57228 and Zm_S 57341) do not show an increase in GUS expression in response to cold treatment.

Figure 16:
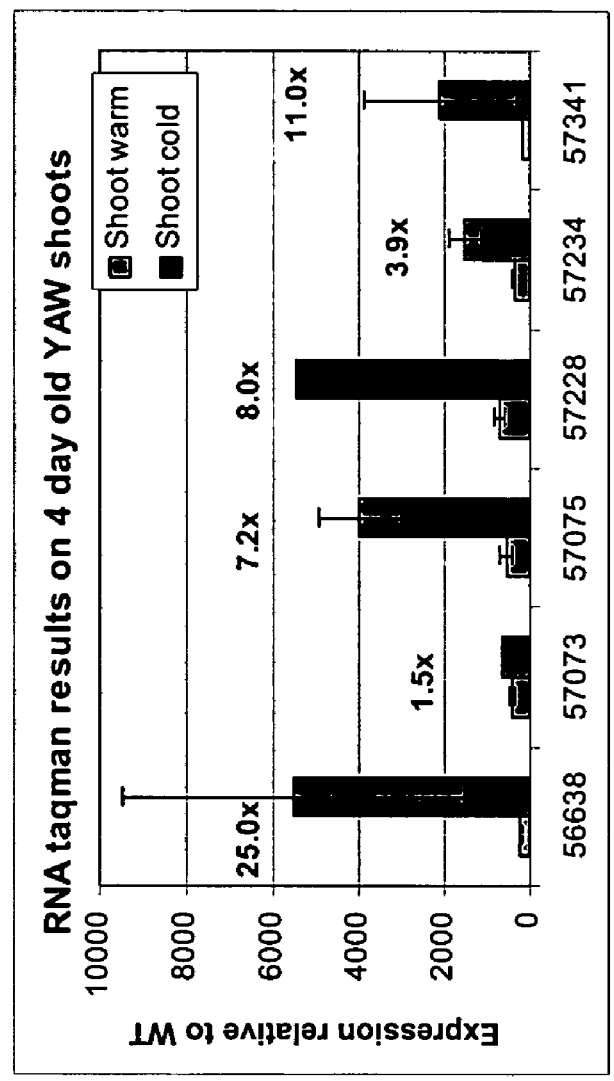

FIG. 16. RNA Taqman results in 4 day old shoot tissue with and without cold shock. Error bars indicate standard deviation. The fold difference in expression between cold and warm treated tissues is indicated above each event.

Figure 17:
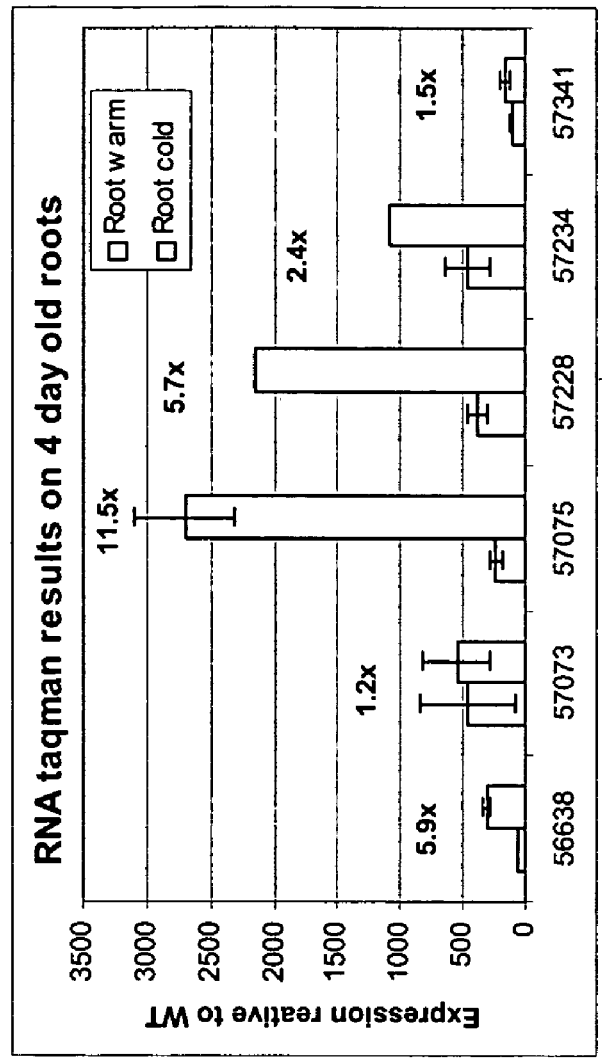

FIG. 17. RNA taqman analysis on 4 day old root tissue with and without cold shock. Error bars indicate standard deviation. The fold difference in expression between cold and warm treated tissues is indicated above each event.

Figure 18:
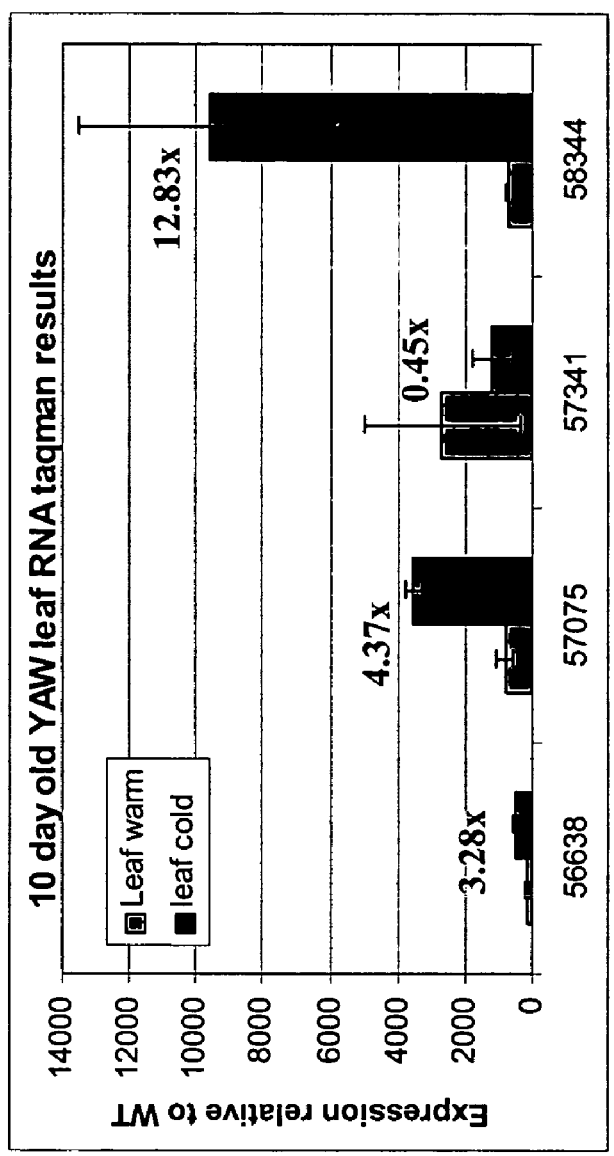

FIG. 18. RNA Taqman analysis of leaf samples from cold and warm treated transgenic plants transformed with pMON42360. The data for each point is an average of readings for two plants for each event. The error bars indicate standard deviation. The fold difference between the cold and warm is indicated above each set of bars.

Figure 19:
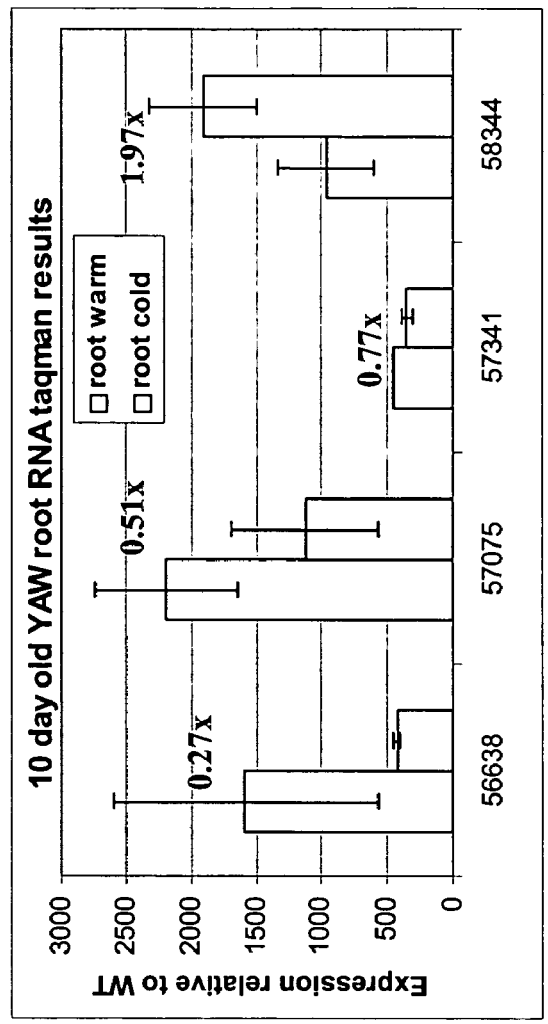

FIG. 19. RNA Taqman analysis of root samples from cold and warm treated transgenic plants transformed with pMON42360. The data for each point is an average of readings for two plants for each event. The error bars indicate standard deviation. The fold difference between the cold and warm is indicated above each set of bars.

Figure 20:
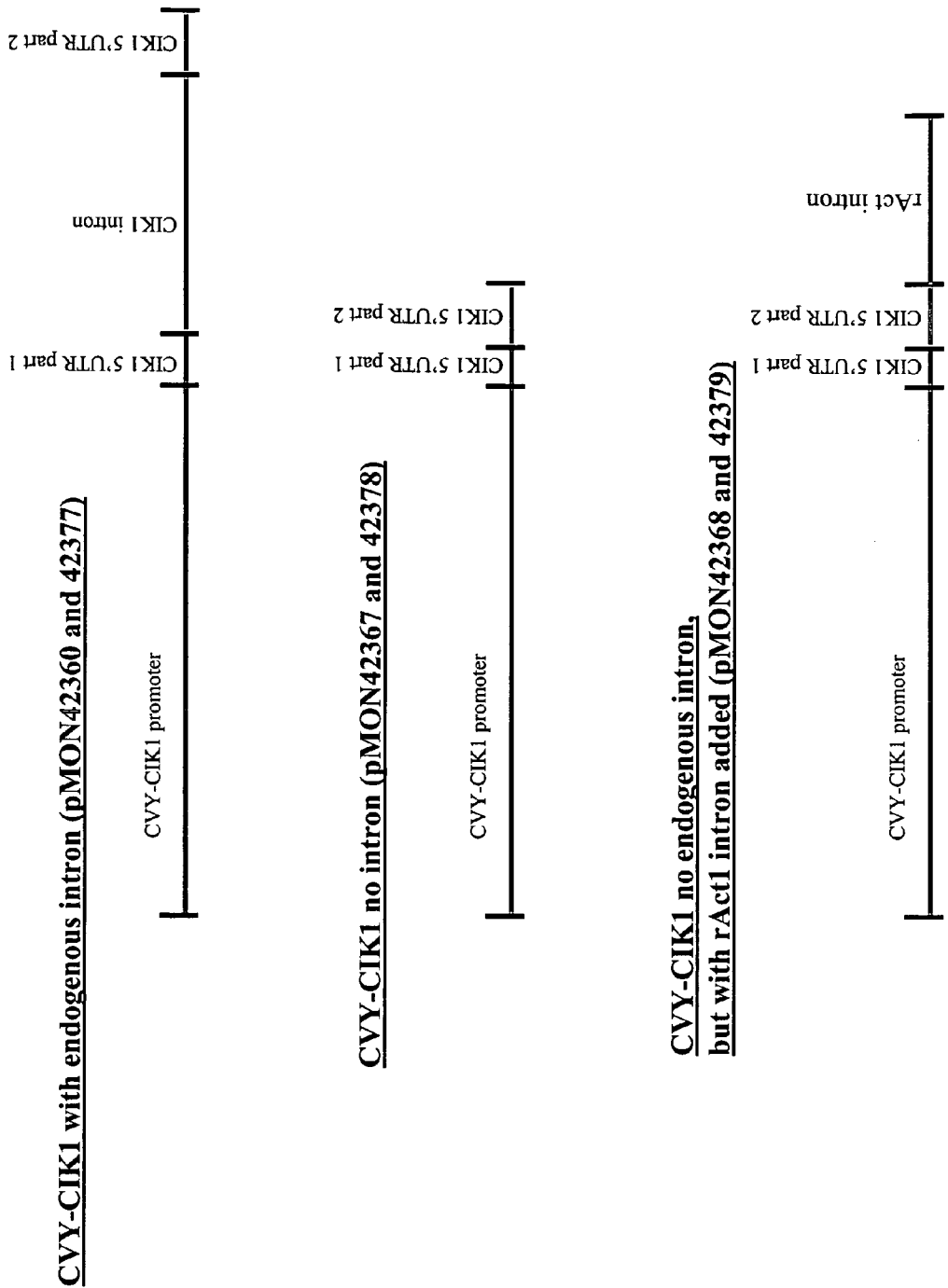

FIG. 20. This figure shows the three DNA constructs placed in plant to test the activity of the CVY-CIK1 promoter. The constructs include the promoter with intron and 5' UTR (from pMON 42360 and pMON42377), the promoter with intron removed (from pMON42367 and 42378), and the promoter with endogenous intron removed but rice actin intron added (from pMON42368 and 42379).

Figure 21:
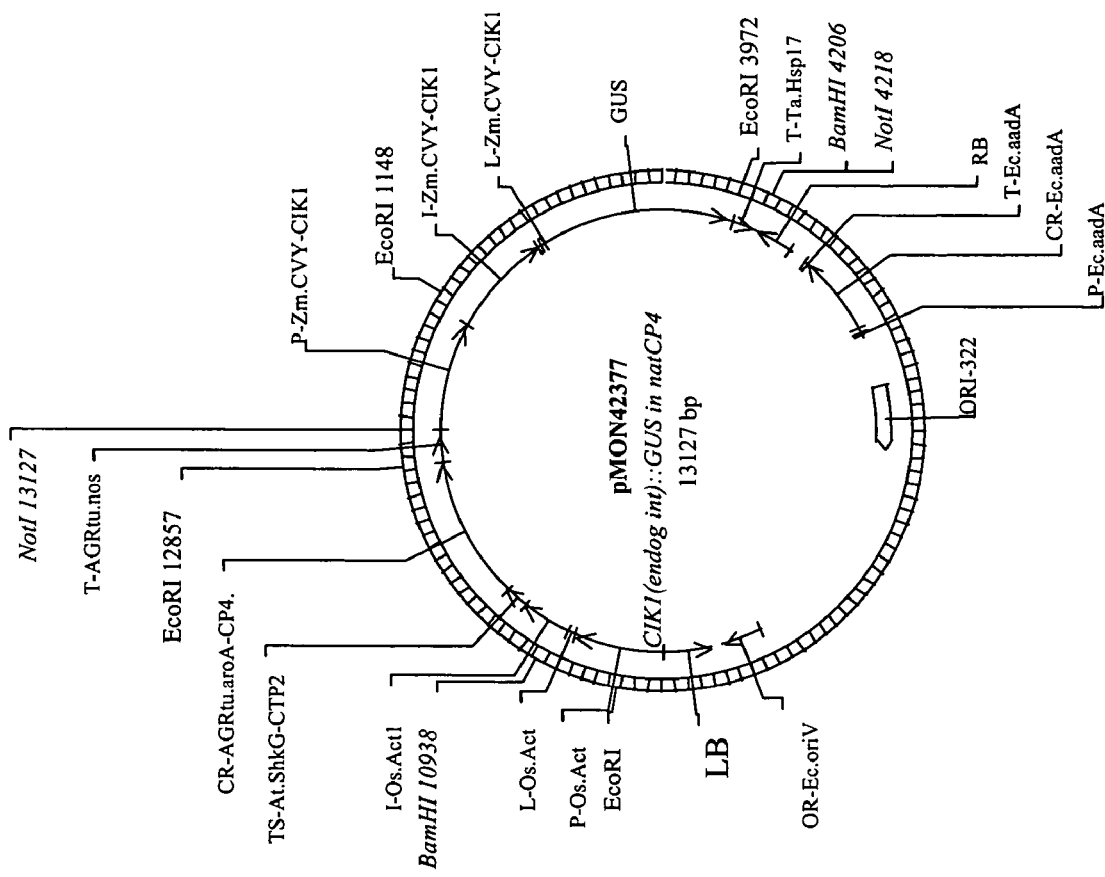
Figure 22:
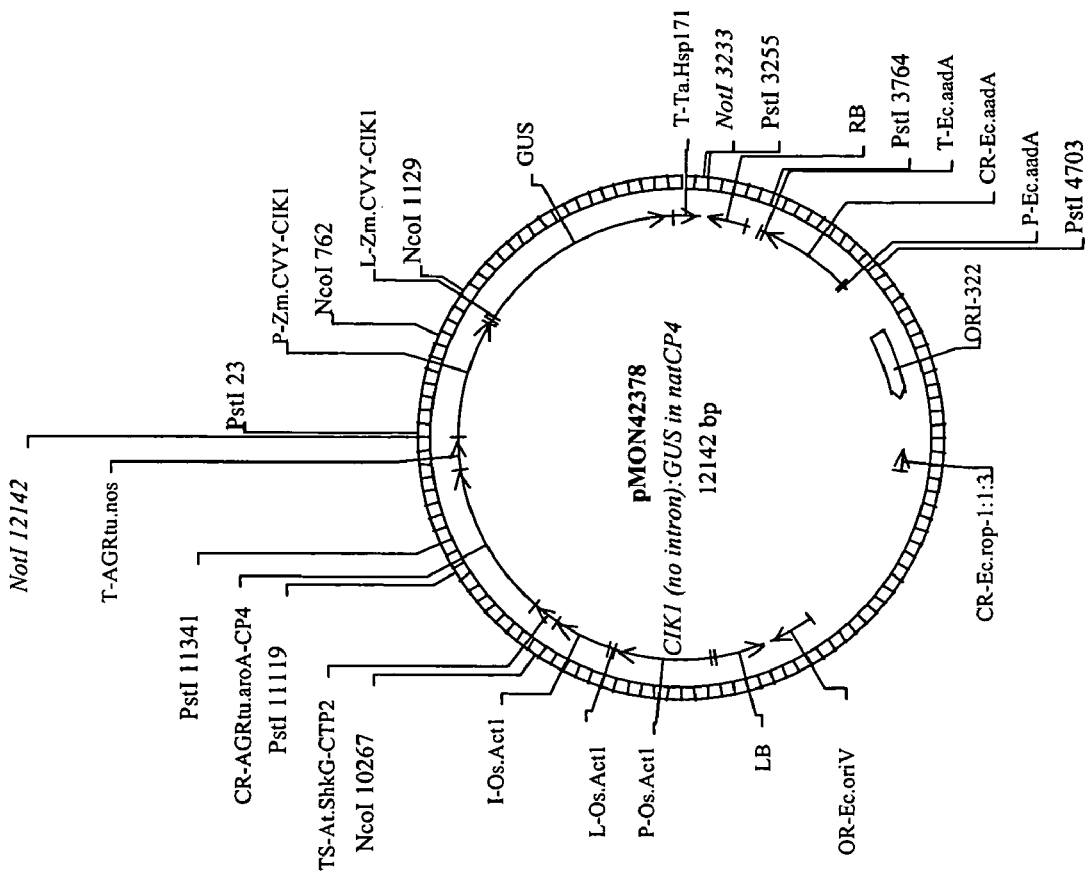
Figure 23:
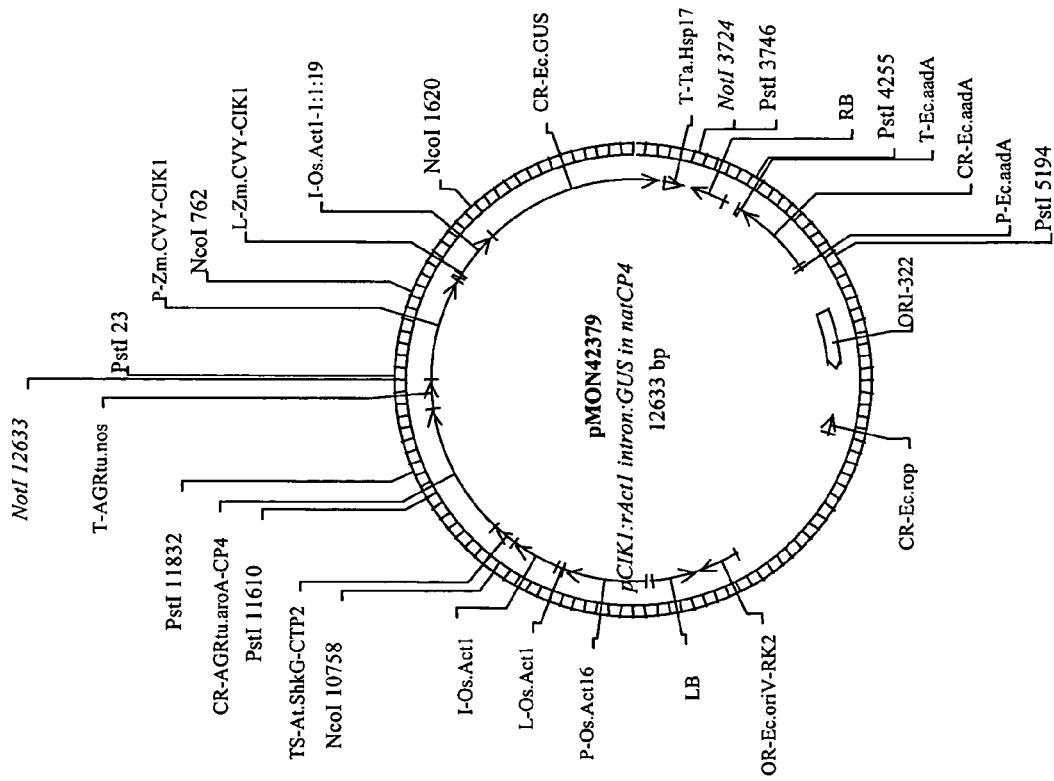
Figure 24:
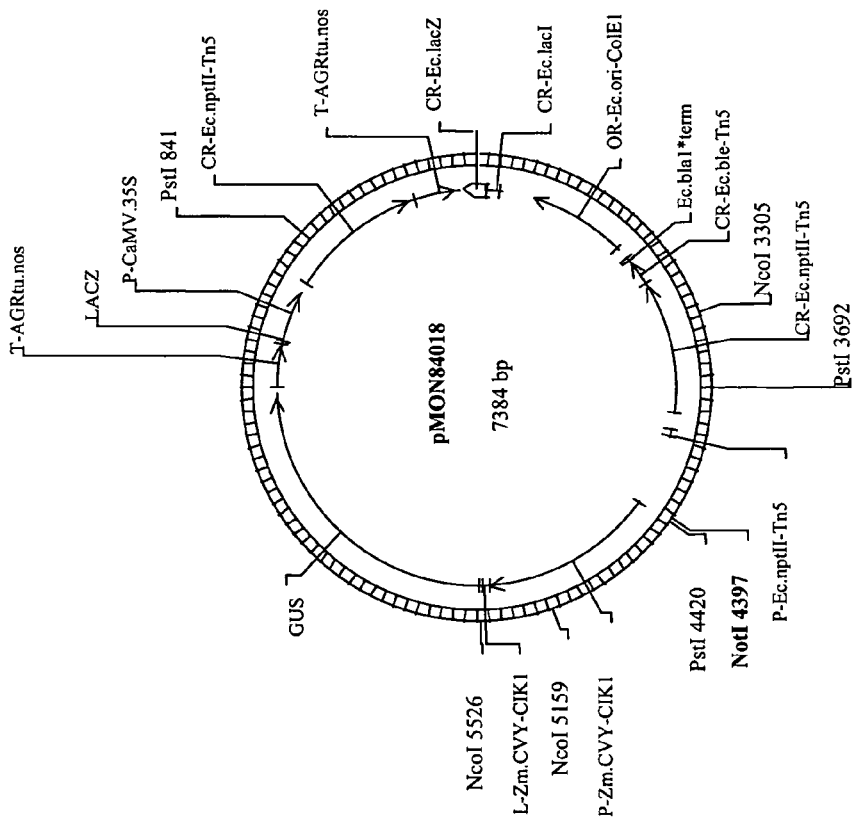

FIG. 21 shows a map of plasmid pMON 42377.
FIG. 22 shows a map of plasmid pMON 42378.
FIG. 23 shows a map of plasmid pMON 42379.
FIG. 24 shows a map of plasmid pMON84018.

DETAILED DESCRIPTION OF THE INVENTION

This invention relates to transcription during abiotic stress in a plant. More specifically the invention relates to isolated DNA sequences, and methods of use of such sequences, and plants containing the DNA sequences (and protein) that directs transcription of operably linked DNA sequences. Such a sequence, and derivatives thereof, can be used to cause the expression of a heterologous DNA sequence which can be transcribed into a sense RNA, anti-sense RNA, RNAi, mRNA, hnRNA, rRNA, or other nucleic acid in a plant. In a particular method, the disclosed promoter upregulates expression in some tissue, or the entire plant, when the plant is placed under some stress, for example cold stress. It could be advantageous to express some genes, or other RNA sequences, in a plant when the plant is placed in a stressful condition. Desired nucleic acid molecules, including genes, could include genes induced by stress in plants, or genes from other organisms (such as bacteria or fungi) that are induced by stress in their native organism. Expression of these genes by a promoter that increases expression under conditions stressful to the plant could increase stress tolerance of said plant. Increased stress tolerance could lead to increased yield, aspects of which could include better germination, increased growth rate, and other advantageous outcomes.

The selected DNA may further comprise DNA from a cloning vector, such as plasmid DNA, or alternatively, may have been introduced as an expression cassette isolated from such vector DNA. The selected DNA may also comprise a sequence encoding a signal peptide. Examples of signal peptides that could be used include a peroxisomal targeting peptide or a chloroplast transit peptide. Examples of a chloroplast transit peptide include the group consisting of chlorophyll a/b binding protein transit peptide, small subunit of ribulose bisphosphate carboxylase transit peptide, EPSPS transit peptide, and dihydrodipocolinic acid synthase transit peptide.

A transgenic plant comprising a selected DNA in accordance with the invention may be any species of plant, including a monocotyledonous or dicotyledonous plant. Examples of monocotyledonous plants include wheat, maize, rye, rice, oat, barley, turfgrass, sorghum, millet and sugarcane. In one embodiment of the invention, the monocotyledonous plant is maize. Examples of dicotyledonous plants include tobacco, tomato, potato, soybean, cotton, canola, alfalfa, sunflower, and cotton. In one embodiment of the invention the dicotyledonous plant is a soybean plant. The transgenic plant prepared in accordance with the invention may be of any generation, including a fertile or sterile $R_0$ transgenic plant as well as seeds thereof, wherein the seed comprises SEQ ID NOs.: 1, 14-17, or a fragment, portion, part, or Cis element (motif) thereof. Also included within the invention are progeny plants of any generation such as a fertile $R_0$ transgenic plant, wherein the progeny plant comprises a heterologous SEQ ID NO: 1, 14-18, or a fragment, portion, part, or Cis element thereof, as well as seed of a progeny plant.

As indicated, an important aspect of the invention provides derivatives of the disclosed promoter. In particular, the current invention includes sequences which have been derived from the disclosed promoter disclosed herein. One efficient means for preparing such derivatives comprises introducing mutations into the sequences of the invention, for example, the sequence given in SEQ ID NO: 1, 14-18. Such mutants may potentially have enhanced or altered function relative to the native sequence, or alternatively, may be silent with regard to function.

Particular sequences which provide the disclosed promoter with desirable expression characteristics could be identified and these or similar sequences introduced into other related or non-related sequences via mutation. Similarly, non-essential elements may be deleted without significantly altering the function of the elements. It is further contemplated that one could mutagenize these sequences in order to enhance their utility in expressing transgenes in a particular species, for example, in maize.

The means for mutagenizing a DNA segment encoding a promoter sequence of the current invention are well-known to those of skill in the art. Mutagenesis may be performed in accordance with any of the techniques known in the art, such as, but not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 12 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single-stranded and double-stranded form. Typical vectors useful in site-directed mutagenesis include vectors such as the M13 phage. These phage are readily commercially available and their use is well known to those skilled in the art. Double-stranded plasmids also are routinely employed in site-directed mutagenesis which eliminates the step of transferring the gene of interest from a plasmid to a phage.

Site-directed mutagenesis can be performed by first obtaining a single-stranded vector or melting apart of two strands of a double-stranded vector which includes within its sequence a DNA sequence which encodes a promoter of the present invention. An oligonucleotide primer bearing the desired mutated sequence is prepared, generally synthetically. This primer is then annealed with the single-stranded vector and subjected to DNA polymerizing enzymes such as the *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The preparation of sequence variants of the selected promoter DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants. Also, myriad other PCR based techniques exist that allow the creation of mutated DNA sequences.

In addition to the corn promoter and its derivatives described herein, one would expect that the described promoter has homologus promoters in corn and other plants. The inventors expect that these promoters will function in a similar way to the described promoter. One such promoter is described in SEQ ID NO 18. This promoter is from rice. These promoters can be identified through the use of sequence similarity searching for either the promoter or the gene to which the promoter is naturally operably linked. Many algorithms and methods are known in the art for accomplishing this task.

As used herein corn line A refers to LH172, corn line B refers to LH244, corn line C refers to LH320, and corn line D refers to HC33.

"Homology" refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For a protein sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, more preferably 30%, more preferably 40%, more preferably 50% identical, more preferably 60%, more preferably 70%, more preferably 80%, more preferably 88%, more preferably 92%, most preferably 95%, across any substantial (25 nucleotide or amino acid, more preferably 50 nucleotide or amino acid, more preferably 100 nucleotide or amino acid, or most preferably the entire length of the shorter sequence) region of the molecule (DNA, RNA, or protein molecule).

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source or species, is modified from its original form; for example, a gene from a fungus being expressed in a plant; or a gene from the same species present under a different promoter, or a promoter driving the expression of a gene or RNA in a non-native location within the genome.

"Germination" is defined as the beginning of growth or development in a seed, spore, or zygote, especially after a period of dormancy. Germination is often used as a broad term, but can be more specifically defined as beginning "with water uptake by the seed (imbibition) and ends with the start of elongation by the embryonic axis, usually the radicle" (Bewley, et al., *Seeds: Physiology of Development and Germination* Plenum Press, New York, 1994, p. 1 {ISBN 0-306-44784-7}). Cold germination is germination occurring at temperatures below (two or more degrees Celsius below) those normal for a particular species or particular strain of plant.

An "isolated" nucleic acid sequence or DNA molecule is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

A first nucleic acid sequence displays "substantial identity" (or is "substantially identical") to a reference nucleic acid sequence if, when optimally aligned (with appropriate nucleotide insertions or deletions totaling less than 20 percent of the reference sequence over the window of comparison) with the other nucleic acid (or its complementary strand); there is at least about 60% nucleotide equivalence; at least about 70%; at least about 80% equivalence; at least about 85% equivalence; at least about 90%; at least about 95%; and/or at least about 98% equivalence over a comparison window of at least 20 nucleotide positions; at least 50 nucleotide positions, at least 100 nucleotide positions; over the entire length of the first nucleic acid. Optimal alignment of sequences for aligning a comparison window may be conducted by algorithms; preferably by computerized implementations of these algorithms (i.e. Wisconsin Genetics Software Package Release 7.0-10.0, Genetics Computer Group, 575 Science Dr., Madison, Wis.). The reference nucleic acid may be a full-length molecule or a portion of a longer molecule.

Hybridization conditions are sequence dependent and will be different in different circumstances. As used herein "stringent conditions" are selected to be about 5° C. lower than the thermal melting point (Tm) for the specific sequence at a defined ionic strength and pH. The "thermal melting point" is the temperature (under defined ionic strength and pH) at which 50% of a target molecule hybridizes to a completely complementary molecule. Appropriate stringent conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6, incorporated herein by reference in its entirety. For example, the salt concentration in the wash step can be selected from a low stringent condition of about 2.0×SSC at 50° C. to a high stringency of about 0.2×SSC at 50° C. In addition, the temperature in the wash step can be increased from low stringent conditions at room temperature, about 22° C., to high stringent conditions at about 65° C. Both temperature and salt concentration may be varied, or either the temperature or the salt concentration may be held constant while the other variable is changed. For the purposes of this disclosure, stringent conditions include at least one wash in 2.0× SSC at a temperature of at least about 50° C. for 20 minutes, or equivalent conditions.

A first nucleic acid sequence is "operably linked" with a second nucleic acid sequence when the sequences are so arranged that the first nucleic acid sequence effects the function of the second nucleic-acid sequence. Often, the two sequences are part of a single contiguous nucleic acid molecule and sometimes are adjacent. For example, a promoter is operably linked to a gene if the promoter regulates or mediates transcription of the gene.

The term "nucleotide sequence" as used herein means both the sense and antisense strands of a nucleic acid molecule as either individual single strands or in the duplex. It includes, but is not limited to, self-replicating plasmids, chromosomal sequences, and infectious polymers of DNA or RNA.

A nucleotide sequence is said to be the "complement" of another nucleotide sequence if they exhibit complete complementarity. As used herein, molecules are said to exhibit "complete complementarity" when every nucleotide of one of the sequences is complementary to a nucleotide of the other.

As used herein the terms "a coding sequence", "structural DNA sequence" and "a structural nucleotide sequence" mean a nucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant nucleotide sequences.

The term "recombinant DNAs" or "recombinant DNA molecules" as used herein means DNA that contains a genetically engineered modification through manipulation via mutagenesis, restriction enzymes, and the like. The nucleic acid itself can come from either naturally occurring sources or can be created in the laboratory. It can also include all vectors created by DNA engineering, for example, all the DNA molecules included herein designated by pMON. For example, it can include molecules containing naturally occurring DNA or cDNA, or DNA molecules of synthetic origin in a plasmid, or isolated. A "recombinant" nucleic acid or "recombinant DNA molecule" can be made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988). The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

Both terms "polypeptide" and "protein", as used herein, mean a polymer composed of amino acids connected by peptide bonds. An amino acid unit in a polypeptide (or protein) can be called a residue. The terms "polypeptide" and "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a polypeptide, that polypeptide is specifically reactive to antibodies elicited to the same polypeptide but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties*, 2nd ed., T. E. Creighton, W.H. Freeman and Company, New York (1993). Many detailed reviews are available on this subject, such as, for example, those provided by Wold, F., Post-translational Protein Modifications. Perspectives and Prospects, pp. 1-12 in *Post-translational Covalent Modification of Proteins*, B. C. Johnson, Ed., Academic Press, New York (1983); Seifter et al., *Meth. Enzymol.* 182:626-M (1990) and Rattan et al., *Protein Synthesis: Post-translational Modifications and Aging*, Ann. N.Y. Acad. Sci. 663:48-62 (1992), herein incorporated by reference in their entirety. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine-containing and the methionine-less amino terminal variants of the polypeptide of the invention. Thus, as used herein, the terms "protein" and "polypeptide" include any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids. This definition is meant to include norleucine, ornithine, homocysteine, and homoserine.

The term "amino acid sequence" means the sequence of amino acids in a polypeptide (or protein) that is written starting with the amino-terminal (N-terminal) residue and ending with the carboxyl-terminal (C-terminal) residue. "Percentage of sequence identity" is determined by comparing two optimally aligned sequences over a comparison window, wherein the portion of the polynucleotide or amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

One skilled in the art will recognize that the values of the above substantial identity of nucleotide sequences can be appropriately adjusted to determine corresponding sequence identity of two nucleotide sequences encoding the polypeptides of the present invention by taking into account codon degeneracy, conservative amino acid substitutions, reading frame positioning and the like.

"Expression" means the transcription and stable accumulation of sense, RNAi, or antisense RNA derived from the nucleic acid molecule of the present invention. Expression may also refer to translation of mRNA into a polypeptide.

The term "a gene" means the segment of DNA that is involved in producing a polypeptide. Such segment of DNA includes regulatory sequences preceding (5' non-coding sequences) and following (3' non-coding sequences) the coding region as well as intervening sequences (introns) between individual coding segments (exons). A "Native gene" means a gene as found in nature with its own regulatory sequences. "Chimeric gene" means any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" means a native gene in its natural location in the genome of an organism. A "foreign gene" means a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Propagule" includes all products of meiosis and mitosis from a plant cell, including but not limited to, seed and parts of the plant able to propagate a new plant. For example, propagule includes a shoot, root, or other plant part that is capable of growing into an entire plant. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

A "substantial portion" of a nucleotide sequence comprises enough of the sequence to afford specific identification and/or isolation of a nucleic acid molecule comprising the sequence. Nucleotide sequences can be evaluated either manually by one skilled in the art, or by using computer based sequence comparison and identification tools that employ algorithms such as BLAST (Basic Local Alignment Search Tool; Altschul et al. *J Mol. Biol.* 215:403-410 (1993)). In general, a sequence of thirty or more contiguous nucleotides is necessary in order to putatively identify a nucleotide sequence as homologous to a gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid molecule comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

For example, nucleic acid molecules described herein, either as cDNAs or genomic DNAs, could be isolated directly by using all or a substantial portion of the nucleic acid molecules of the present invention as DNA hybridization probes to screen cDNA or genomic libraries from any desired plant employing methodology well known to those skilled in the art. Methods for forming such libraries are well known in the art. Specific oligonucleotide probes based upon the nucleic acid molecules of the present invention can be designed and synthesized by methods known in the art. Moreover, the entire sequences of the nucleic acid molecules can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full length cDNA or genomic DNAs under conditions of appropriate stringency.

Alternatively, the nucleic acid molecules of interest can be amplified from nucleic acid samples using amplification techniques. For instance, the disclosed nucleic acid molecules may be used to define a pair of primers that can be used with the polymerase chain reaction.

In addition, two short segments of the nucleic acid molecules of the present invention may be used in polymerase chain reaction protocols to amplify longer nucleic acid molecules from DNA or cDNA produced from RNA. For example, the skilled artisan can follow the RACE protocol (Frohman et al., Proc. Natl. Acad. Sci. USA 85:8998 (1988) to generate cDNAs by using PCR to amplify copies of the region between a single point in the transcript and the 3' or 5' end. Primers oriented in the 3' and 5' directions can be designed from the nucleic acid molecules of the present invention. Using commercially available 3'RACE or 5'RACE systems (Gibco BRL, Life Technologies, Gaithersburg, Md. U.S.A.), specific 3' or 5' cDNA fragments can be isolated (Ohara et al., Proc. Natl. Acad. Sci. USA 86:5673 (1989); Loh et al., Science 243:217 (1989), both of which are herein incorporated by reference in their entireties). Products generated by the 3' and 5' RACE procedures can be combined to generate full-length cDNAs (Frohman and Martin, Techniques 1: 165 (1989).

Another aspect of the present invention relates to methods for obtaining a nucleic acid molecule comprising a nucleotide sequence described herein (i.e. see sequence listing). One method of the present invention for obtaining a nucleic acid molecule encoding all or a substantial portion of the amino acid sequence of a protein encoded on the same gene as the sequences described herein would be: (a) probing a cDNA or genomic library with a hybridization probe comprising a nucleotide sequence encoding all or a substantial portion of a DNA, cDNA, or RNA molecule described herein (b) identifying a DNA clone that hybridizes under stringent conditions to the hybridization probe; (c) isolating the DNA clone identified in step (b); and (d) sequencing the cDNA or genomic fragment that comprises the clone isolated in step (c).

Another method of the present invention for obtaining a nucleic acid molecule described herein: (a) synthesizing a first and a second oligonucleotide primer, wherein the sequences of the first and second oligonucleotide primer encode two different portions of the nucleotide sequence described herein, and are manufactured in such a way as to allow DNA amplification (for example, PCR®) (Maniatis et al., Molecular Cloning: A Laboratory Manual, Second Edition (1989) Cold Spring Harbor Laboratory, Cold Spring Harbor, N.Y., Hartl, et al., Genetics, Analysis of genes and genomes, 5$^{th}$ edition, Jones and Bartlett Publishers, Inc., Sudbury, Mass.); and (b) amplifying and obtaining the nucleic acid molecule directly from genomic libraries using the first and second oligonucleotide primers of step (a) wherein the nucleic acid molecule encodes all or a substantial portion of the sequence described herein.

All or a substantial portion of the nucleic acid molecules of the present invention may also be used as probes for genetically and physically mapping the genes that they are a part of, and as markers for traits linked to those genes. Such information may be useful in plant breeding in order to develop lines with desired phenotypes. For example, the nucleic acid molecules of the present invention may be used as restriction fragment length polymorphism (RFLP) markers. Southern blots (Maniatis et al., Molecular Cloning: A Laboratory Manual, Second Edition (1989) Cold Spring Harbor Laboratory, Cold Spring Harbor, N.Y.) of restriction-digested plant genomic DNA may be probed with the nucleic acid fragments of the present invention. The resulting banding patterns may then be subjected to genetic analyses using computer programs such as MapMaker (Lander et al., *Genomics* 1:174-181 (1987), or can be analyzed by one skilled in the art, in order to construct a genetic map. Fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the nucleotide sequence of the present invention in the genetic map previously obtained using this population (Botstein et al., *Am. J. Hum. Genet.* 32:314-331 (1980).

Methods for determining gene expression, even expression of a gene from an introduced transgene are common in the art, and include RT-PCR, Northern blots, and Taqman®. Taqman® (PE Applied Biosystems, Foster City, Calif.) is described as a method of detecting and quantifying the presence of a DNA or RNA/cDNA molecule and is fully described in the instructions provided by the manufacturer, and at their website. Briefly, in the case of a genomic sequence a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert DNA due to successful amplification and hybridization.

The term "transgenic plant" means a plant that contains an exogenous nucleic acid, which can be derived from the same plant species or from a different species. By "exogenous" it is meant that a nucleic acid molecule originates from outside the plant which the nucleic acid molecule is introduced. An exogenous nucleic acid molecule can have a naturally occurring or non-naturally occurring nucleotide sequence. One skilled in the art understands that an exogenous nucleic acid molecule can be a heterologous nucleic acid molecule derived from a different plant species than the plant into which the nucleic acid molecule is introduced or can be a nucleic acid molecule derived from the same plant species as the plant into which it is introduced. Exogenous nucleic acid molecules may be transferred into a plant cell by the use of a recombinant DNA construct (or vector) designed for such a purpose.

"Plant cell", as used herein, includes without limitation, seeds suspension cultures, embryos, meristematic regions, callus tissue, leaves, roots, shoots, gametophytes, sporophytes, pollen, microspores, and any other part of any of various photosynthetic, eukaryotic, multicellular or unicellular organisms of the kingdom Plantae characteristically producing embryos, containing chloroplasts, having cellulose cell walls, and often lacking the power of locomotion.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

"Plant genomic DNA" is defined as DNA isolated from a plant, seed, plant tissue, tissue culture cell(s), seed(s), or any other portion of a plant wherein a portion of genetic blueprint for a plant can be isolated. Plant genomic DNA may include the contents of the nucleus of a cell, the contents of the nucleus and the organelles, or the contents of the meiotic products of a plant.

The present invention also provides a plant recombinant DNA construct (or vector) for producing transgenic plants, wherein the plant recombinant DNA construct (or vector) comprises a nucleotide sequence described herein. Method which are well known to those skilled in the art may be used to prepare the plant recombinant DNA construct (or vector) of the present invention. These methods include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1988).

A plant recombinant DNA construct (vector) of the present invention will typically comprise a selectable marker which confers a selectable phenotype on plant cells. Selectable markers may also be used to select for plants or plant cells that contain the exogenous nucleic acid molecules encoding polypeptides of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., *Mol. Gen. Genet.* 199:183-188 (1985)) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988)) which encodes glyphosate resistance; a nitrilase gene which confers resistance to bromoxynil (Stalker et al., *J. Biol. Chem.* 263:6310-6314 (1988)); a mutant acetolactate synthase gene (ALS) which confers imidazolinone or sulphonylurea resistance (European Patent Application 154,204 (Sep. 11, 1985)); and a methotrexate resistant DHFR gene (Thillet et al., *J. Biol. Chem.* 263:12500-12508 (1988)).

A plant recombinant DNA construct (vector) of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987); Jefferson et al., *EMBO J.* 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., *Proc. Natl. Acad. Sci.* (U.S.A.) 75:3737-3741 (1978)), a gene which encodes an enzyme for which various chromogenic substrates are known (e.g., PADAC, a chromogenic cephalosporin); a luciferase gene (Ow et al., *Science* 234:856-859 (1986)) a xylE gene (Zukowsky et al., *Proc. Natl. Acad. Sci.* (U.S.) 80:1101-1105 (1983)) which encodes a catechol dioxygenase that can convert chromogenic catechols; an α-amylase gene (Ikatu et al., *Bio/Technol.* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to melanin; an α-galactosidase, which will cause a color change in a chromogenic α-galactose substrate.

Included within the terms "selectable or screenable marker genes" are also genes which encode a secretable marker whose secretion can be detected as a means of identifying or selecting for transformed cells. Examples include markers which encode a secreted antigen that can be identified by antibody interaction, or even secreted enzymes which can be detected catalytically. Secreted proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (Biochem. Soc. Trans. 15, 17-19 (1987)) to identify transformed cells.

In preparing the recombinant DNA constructs (vectors) of the present invention, the various components of the construct or fragments thereof will normally be inserted into a convenient cloning vector, e.g., a plasmid that is capable of replication in a bacterial host, e.g., *E. coli*. Numerous cloning vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A plant recombinant DNA construct (vector) of the present invention may also include a chloroplast transit peptide, in order to target the polypeptide of the present invention to the plastid. The term "plastid" means the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized polypeptides are expressed from nuclear genes as precursors and are targeted to the plastid by a chloroplast transit peptide (CTP), which is removed during the import steps. Examples of such chloroplast polypeptides include the small subunit of ribulose-1,5-biphosphate carboxylase (ss-RUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid polypeptides may be targeted to the chloroplast by use of polypeptide fusions with a CTP and that a CTP sequence is sufficient to target a polypeptide to the plastid. Those skilled in the art will also recognize that various other recombinant DNA constructs can be made that utilize the functionality of a particular plastid transit peptide to import the enzyme into the plant cell plastid depending on the promoter tissue specificity.

Transgenic plants of the present invention preferably have incorporated into their genome or transformed into their chloroplast or plastid genomes an exogenous nucleic acid molecule (or "transgene"), which comprises at least a nucleotide sequence that comprises a nucleotide sequence described herein. Transgenic plants are also meant to comprise progeny (descendant, offspring, etc.) of any generation of such a transgenic plant, and the propagules, seeds, and parts of those plants. Plant parts, without limitation, include seed, endosperm, ovule and pollen, leaves, roots, tubers, and all other products of mitosis and meiosis.

Many agronomic traits can affect "yield". For example, these could include, without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. For example, these could also include, without limitation, efficiency of germination (including germination in stressed conditions), growth rate (including growth rate in stressed conditions), ear number, seed number per ear, seed size, composition of seed (starch, oil, protein), characteristics of seed fill. "Yield" can be measured in may ways, these might include test weight, seed weight, seed number per plant, seed weight, seed number per unit area (i.e. seeds, or weight of seeds, per acre), bushels per acre, tonnes per acre, tons per acre, kilo per hectare. In an embodiment, a plant of the present invention might exhibit an enhanced trait that is a component of yield. An enhanced trait is a trait, or phenotype of a plant, that is changed in a way that could be viewed as an agronomic improvement when compared to a non-transgenic plant of the same, or very similar, genotype.

"Promoter" refers to a DNA sequence that binds an RNA polymerase (and often other transcription factors as well) and promotes transcription of a downstream DNA sequence. Said sequence can be an RNA that has function, such as rRNA (ribosomal RNA) or tRNA (transfer RNA). Often, the RNA produced is a hetero-nuclear (hn) RNA that has introns which are spliced out to produce an mRNA (messenger RNA). A "plant promoter" is a native or non-native promoter that promotes transcription in plant cells.

Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, cold, or chemicals such as ethanol, jasmonate, salicylic acid, or safeners. Inducible promoters are often "enhanced" in their transcription of genes, namely a gene is often on at some low level prior to the inductive event, and on at a higher level for some period during, and possibly after, the inductive event.

Any plant promoter can be used as a 5' regulatory sequence for modulation expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, nature 290:304-310, 1981; Gruss et al., Proc. Nat. Acad. Sci. USA 78:943-947, 1981; and Khoury and Gruss, Cell 27:313-314, 1983) extending from around 100 bp to 1,000 bp or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr, et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991)). Alternatively, heterologous regulatory sequences can be added to the 5' upstream region of an inactive, truncated promoter, e.g., a promoter including only the core TATA and, sometimes, the CCAAT elements (Fluhr, et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or "cis-elements," or "motifs" each of which can confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). "cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, in: Martin, Curr. Opinions Biotech. 7:130-138, 1996; Murai, In: Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. The promoter sequences of the present invention can contain "cis elements" which can modulate gene expression. Cis elements can be part of the promoter, or can be upstream or downstream of said promoter. Cis elements (or groups thereof) acting at a distance from a promoter are often referred to as repressors or enhancers. Enhancers act to upregulate the transcriptional initiation rate of RNA polymerase at a promoter, repressors act to decrease said rate. In some cases the same elements can be found in a promoter and an enhancer or repressor.

Cis elements (motifs) can be identified by a number of techniques, including deletion analysis, i.e., deleting one or more nucleotides from the 5' end or internal to a promoter; DNA binding protein analysis using Dnase I footprinting, methylation interference, electrophoresis mobility-shift assays (EMSA or gel shift assay), in vivo genomic footprinting by ligation-mediated PCR, and other conventional assays; or by sequence similarity with known cis element motifs by conventional sequence comparison methods. The fine structure of a cis element can be further studied by mutagenesis (or substitution) of one or more nucleotides or by other conventional methods. See, e.g., Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. A functional plant promoter could be produced by combining or excising one, two, three, four, five, six, seven, eight, nine, ten, eleven, twelve, thirteen, fourteen, fifteen, sixteen, seventeen, eighteen, nineteen, twenty, twenty-one, twenty-two or more motifs from one promoter and combining those motifs to create another promoter using recombinant DNA technology.

Cis elements can be obtained by chemical synthesis or by cloning from promoters that includes such elements, and they can be synthesized with additional flanking sequences that contain useful restriction enzyme sites to facilitate subsequence manipulation. In one embodiment, the promoters are comprised of multiple distinct "cis-acting transcriptional regulatory elements," or simply "cis-elements," each of which can modulate a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). For example, combinations of cis element regions or fragments of the $^{35}$S promoter can show tissue-specific patterns of expression (see U.S. Pat. No. 5,097,025). In one embodiment sequence regions comprising "cis elements" of the nucleic acid sequences of SEQ ID NO: 1, 14-18 can be identified using computer programs designed specifically to identity cis elements, domains, or motifs within sequences by a comparison with known cis elements or can be used to align multiple 5' regulatory sequences to identify novel cis elements. Activity of a cloned promoter or putative promoter (cloned or produced in any number of ways including but not limited to; isolation from an endogenous piece of genomic DNA directly by cloning or by PCR; chemically synthesizing the piece of DNA) can be tested in any number of ways including testing for RNA (Northern, Taqman®, quantitative PCR, etc.) or production of a protein with an activity that is testable (i.e. GUS, chloremphenicol acetyl transferase (CAT)). Multimerization of elements or partial or complete promoters can change promoter activity (i.e. e35S, U.S. Pat. Nos. 5,359,142, 5,196,525, 5,322,938, 5,164,316, and 5,424,200, all herein incorporated by reference). Cis elements may work by themselves or in concert with other elements of the same or different type, i.e. hormone- or light-responsive elements.

The technological advances of high-throughput sequencing and bioinformatics have provided additional molecular tools for promoter discovery. Particular target plant cells, tissues, or organs at a specific stage of development, or under particular chemical, environmental, or physiological conditions can be used as source material to isolate the mRNA and construct cDNA libraries. The cDNA libraries are quickly sequenced and the expressed sequences catalogued electronically. Using sequence analysis software, thousands of sequences can be analyzed in a short period, and sequences from selected cDNA libraries can be compared. The combination of laboratory and computer-based subtraction methods allows researchers to scan and compare cDNA libraries and identify sequences with a desired expression profile. For example, sequences expressed preferentially in one tissue can be identified by comparing a cDNA library from one tissue to cDNA libraries of other tissues and electronically "subtracting" common sequences to find sequences only expressed in the target tissue of interest. The tissue enhanced sequence can then be used as a probe or primer to clone the corresponding full-length cDNA. A genomic library of the target plant can then be used to isolate the corresponding gene and the associated regulatory elements, including promoter sequences.

A "fragment" of the present invention is a contiguous nucleic acid of ten or more nucleotides, with 80% or greater identity to the nucleic acid sequence in question.

The term "tissue-specific promoter" means a regulatory sequence that causes an enhancement of transcription from a downstream gene in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

It is further recognized that since in most cases the exact boundaries of regulatory sequences have not been completely defined, DNA fragments of different lengths may have identical promoter activity.

"Stress" is a condition occurring in response to external influences capable of affecting the physical characteristics of a plant. Characteristics include, but are not limited to, all biotic and abiotic stresses that could influence a plant, from infection to environment.

"Abiotic stress" is stress caused to a plant by any means, or weather condition, that does not include another living organism. For example, drought, heat, cold, water stress, salt stress, lack of light, too much light, or any other of a myriad of conditions caused by the environment that the plant is placed in not being optimal for the growth, yield, or survival of said plant.

In a preferred embodiment of the invention, a transgenic plant expressing the desired protein is to be produced. Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile mediated delivery of the desired polynucleotide.

Agrobacterium-mediated transformation is achieved through the use of a genetically engineered soil bacterium belonging to the genus Agrobacterium. A number of wild-type and disarmed strains of Agrobacterium tumefaciens and Agrobacterium rhizogenes harboring Ti or Ri plasmids can be used for gene transfer into plants. Gene transfer is done via the transfer of a specific DNA known as "T-DNA", that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation". Following the inoculation, the Agrobacterium and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880; U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication WO 95/06128), barley, wheat (U.S. Pat. No. 5,563,055, specifically incorporated herein by reference in its entirety), rice, oat, rye, sugarcane, and sorghum; as well as a number of dicots including tobacco, soybean (U.S. Pat. No. 5,322,783, specifically incorporated herein by reference in its entirety), sunflower, peanut, cotton, tomato, and legumes in general (U.S. Pat. No. 5,563,055, specifically incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline.

The regeneration, development, and cultivation of plants from various transformed explants is well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

It has also been observed in the art that some stress responses have similar effects on the plant, and resistance to one may provide resistance to another. This is seen, for example, between the responses to dehydration and low temperature (Shinozaki, et al., Current Opinions in Plant Biology 3 (3):217, 2000).

The CVY-CIK1 promoter encompasses the entire DNA sequence set forth in SEQ ID NO:1. It also encompasses the polynucleotide sequence naturally surrounding SEQ ID NO:1 in the genome of a plant, and any portion of the polynucleotide sequence comprising a plant promoter, including but not limited to SEQ ID NOs: 14-17.

The laboratory procedures in recombinant DNA technology used herein are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y. (1989).

Plasmids discussed herein all contain an origin of replication for propagation in bacteria, for example, *E. coli*. All also contain a selectable marker for determining which bacteria contain said plasmid, for example, a beta-lactamase that cleaves the beta-lactam ring in present in many antibiotics, for example, carbenicillin and penicillin.

The nomenclature for DNA bases as set forth at 37 CFR § 1.822 is used. The standard one- and three-letter nomenclature for amino acid residues is used.

The definitions and methods included herein are provided to better define the current invention and to guide those of ordinary skill in the art in the practice of the present invention. Unless otherwise noted, terms are to be understood according to conventional usage by those of ordinary skill in the art. Definitions of common terms used in molecular biology and molecular genetics can also be found in Lewin, *Genes VII*, Oxford University Press and Cell Press, New York, 2000; Buchanan, et al., *Biochemistry and Molecular Biology of Plants*, Courier Companies, USA, 2000; Lodish, et al., *Molecular Cell Biology*, W.H. Freeman and Co., New York, 2000. Common terms in genetics can be found in the prior as well as Lynch, et al., *Genetics and Analysis of Quantitative Traits*, Sinauer and Associates, Sunderland, Mass., 1998; Gonick, et al., *The Cartoon Guide to Genetics*, HarperCollins Publishers, New York, 1983; Hartwell, et al., *Genetics: From Genes to Genomes*, McGraw-Hill Companies, Boston, Mass., 2000; Hartl, et al., *Genetics: Analysis of Genes and Genomes*, Jones and Bartlett Publishers, Sudbury, Mass., 2000; Strachan, et al., *Human Molecular Genetics*, John Wiley and Sons, New York, 1999.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application is specifically and individually indicated to be incorporated by reference.

The following examples are included to demonstrate embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings and examples is to be interpreted as illustrative and not in a limiting sense.

EXAMPLES

Shown below are examples detailing some of the experiments that were done. Constructs were made with the promoter and derivatives thereof with different selectable markers for transformation. Sets of constructs were made, each with different selectable markers, and different experiments were done with each set. Changes were also made to other expression elements (such as introns).

RNA for the following examples was, or could be, isolated in the following way: Frozen plant tissues are ground into a fine powder under liquid nitrogen using a ceramic mortar and pestle. RNA is then extracted from this powder using the Trizol reagent from Invitrogen/GibcoBRL (Carlsbad, Calif.; catalog number 15596) according to the manufacturers instructions. C following a number is meant to indicate degrees Celcius.

Example 1

Cloning of the CVY-CIK1 Promoter Region (SEQ ID NO: 1) from the Genomic DNA of Corn Oligos were used to amplify a 5' region of the CVY-CIK1 gene from corn (Wigor line) genomic DNA (oligos from Invitrogen).

```
                                          (SEQ ID NO: 2)
JA01-19: TCG GTG ACA ATG CAG CCC TCT TAG C (SEQ ID NO: 3)
JA01-20: ag cca tgg CTT CCG ACA GAT GAA GGT TAC T (SEQ ID NO: 4)
JA01-21: ATC CGC CGC CGA TGG AAG AGG AG (SEQ ID NO: 5)
JA01-22: at ctg cag ATC CAC GCT CGC TCG GGT GT
```

Oligo JA01-20 was engineered with a NcoI restriction site on the 5'end to allow for restriction digestion and cloning into a compatibly cut vector. Oligo JA01-22 was engineered with a PstI site on the 5' end to allow for restriction digestion and cloning into a compatibly cut vector.

A primary PCR reaction was performed with the High Fidelity PCR System from Roche Molecular Biochemicals (Roche), Indianapolis, Ind. (cat # 1732641) (according to the manufacturer's instructions) using oligos JA01-19 and JA01-21 to amplify the CVY-CIK1 upstream sequence from genomic corn DNA (Wigor genotype). This PCR reaction amplified the CVY-CIK1 promoter sequence, including the 5'UTR and an apparent endogenous 5'UTR intron and first exon.

| Reaction conditions: | volume (ul) |
| --- | --- |
| Wigor genomic DNA (0.58 ug/ul) | 1.0 |
| 10 mM dNTP mix | 2.0 |
| JA01-19 (10 uM) | 3.0 |
| JA01-21 (10 uM) | 3.0 |
| 10× PCR buffer | 10.0 |
| Polymerase enzyme mix (3.5 U/ul) | 0.75 |
| Water | 80.25 |

Cycling Conditions:
1. 94° C. for 2 minutes
2. 94° C. for 15 seconds
3. 63° C. for 30 seconds
4. 72° C. for 2 minutes
5. repeat steps 2-4 for a total of 10 times
6. 94° C. for 15 seconds
7. 63° C. for 30 seconds
8. 72° C. for 2 minutes (plus an additional 5 seconds per cycle)
9. repeat steps 6-8 for a total of 15 cycles
10. 72° C. for 7 minutes Use 1 ul of a 1/20 dilution of the PCR product from the above reaction in an additional PCR reaction using the nested oligos JA01-20 and JA01-22. Repeat as above, except change the annealing temperature in steps 3 and 7 to 56° C. instead of 63° C. Run 15 ul of the nested PCR product on an agarose gel, cut out PCR product and purify DNA using the Qiaquick Gel Extraction Kit as directed by the manufacturer (Qiagen, catalog #28704). Ligate the PCR fragment into the pCR-Blunt II vector in the Zero Blunt TOPO PCR cloning Kit (Invitrogen cat. #K2800-20) as directed by the manufacturer to produce pMON42355 (FIG. 1). The insert was sequenced.

Example 2

An intron in the 5' untranslated region (5' UTR) was identified and a plasmid created where this "intronless" promoter (SEQ ID NO: 17) drives the transcription of GUS. A plasmid was also created wherein the rice actin intron was added to the intronless version of the promoter (SEQ ID NO: 16).

Upon cloning of the CVY-CIK1 upstream region (SEQ ID NO: 1) using PCR (example 1), an intron was identified in the 5'UTR of this gene. This was done by doing an alignment of the cDNA sequence for the CVY-CIK1 gene (including some of the 5'UTR) with the sequence upstream of the start codon for this gene identified through Genome Walker experiments using genomic DNA identified 984 bp of sequence not found in the cDNA sequence for the 5'UTR. The ends of this intron region show a high similarity of the consensus splice ends for plant introns described by Lorkovic, et al (*Trends in Plant Sciences* (2000) 5:160-167).

To determine what effect (if any) this intron sequence has on the regulation of the expression of this gene, the intron sequence was removed from the upstream sequence through the use of PCR. In order to retain the entire 5'UTR sequence for this gene even when the intron is removed, a long oligonucleotide was constructed which would anneal to the promoter region directly upstream of the intron, but would contain a tail of bases at the 5'end of the oligo which would add the 54 bp of 5'UTR to the remainder of the promoter region after PCR (this 54 bp initially can be found between the 3'end of the intron sequence and the start ATG for the gene).

The PCR reactions to remove the intron were conducted using the following oligonucleotides:

JA01-22: (in earlier examples)

JA01-25:

(SEQ ID NO: 6)
agccatgg*CTTCCGACAGATGAAGGTTACTGTGAACCTTCAGGTTATTCT CTTCCAACAC*CTTCCAGCGCTGAGCCCGAG (in JA01-25, lower case letters add a NcoI site to the end of the PCR product for cloning, the underlined italic letters will add the region of the 5'UTR between the intron and the start ATG for the gene to the PCR product, and the standard capital letters will anneal to the 3' end of the promoter region just upstream of the intron to produce the main PCR product.)

Before conducting the PCR to remove the intron, the promoter fragment upstream of the intron was cut out of pMON42355 using an EcoR1 digest and gel purified. This was done to prevent any mis-priming of oligo JA01-25 to the region of the 5'UTR between the intron and the coding region. The PCR reaction was set up using as below (using the Roche High Fidelity PCR kit as directed by the manufacturer):

| | |
|---|---|
| DNA (EcoRI digest above) | 1.0 ul |
| 10 mM dNTP mix | 2.0 ul |
| 10 uM JA01-22 | 3.0 ul |
| 10 uM JA01-25 | 3.0 ul |
| 10× reaction buffer | 10.0 ul |
| Enzyme mix | 0.75 ul |
| Water | 80.25 ul |

Cycling Conditions:

| | |
|---|---|
| 1. 94 degrees C. | 2 minutes |
| 2. 94 degrees C. | 15 seconds |
| 3. 65 degrees C. | 30 seconds |
| 4. 72 degrees C. | 1 minute and 30 seconds |
| 5. repeat steps 2-4 for a total of 10 times | |
| 6. 94 degrees C. | 15 seconds |
| 7. 65 degrees C. | 30 seconds |
| 8. 72 degrees C. | 1 minute and 30 seconds, plus an additional 5 seconds each additional cycle |
| 9. repeat steps 6-8 for a total of fifteen times | |
| 10. 72 degrees C. | 7 minutes |
| 11. 4 degrees C. | hold |

The PCR reaction was run on an agarose gel, and the product was purified using the Qiagen gel purification kit as directed by the manufacturer. Clone into pCR-BluntII TOPO from Invitrogen (Zero Blunt TOPO PCR cloning Kit, cat. #K2800-20) as directed by the manufacturer to produce pMON42357 (FIG. 2). The backbone of this plasmid is commercially available through Invitrogen (Carlsbad, Calif.) as Zero Blunt Topo PCR cloning kit (k280020), including descriptions of relevant parts of the plasmid including CCDB lethal.

Figure 4:
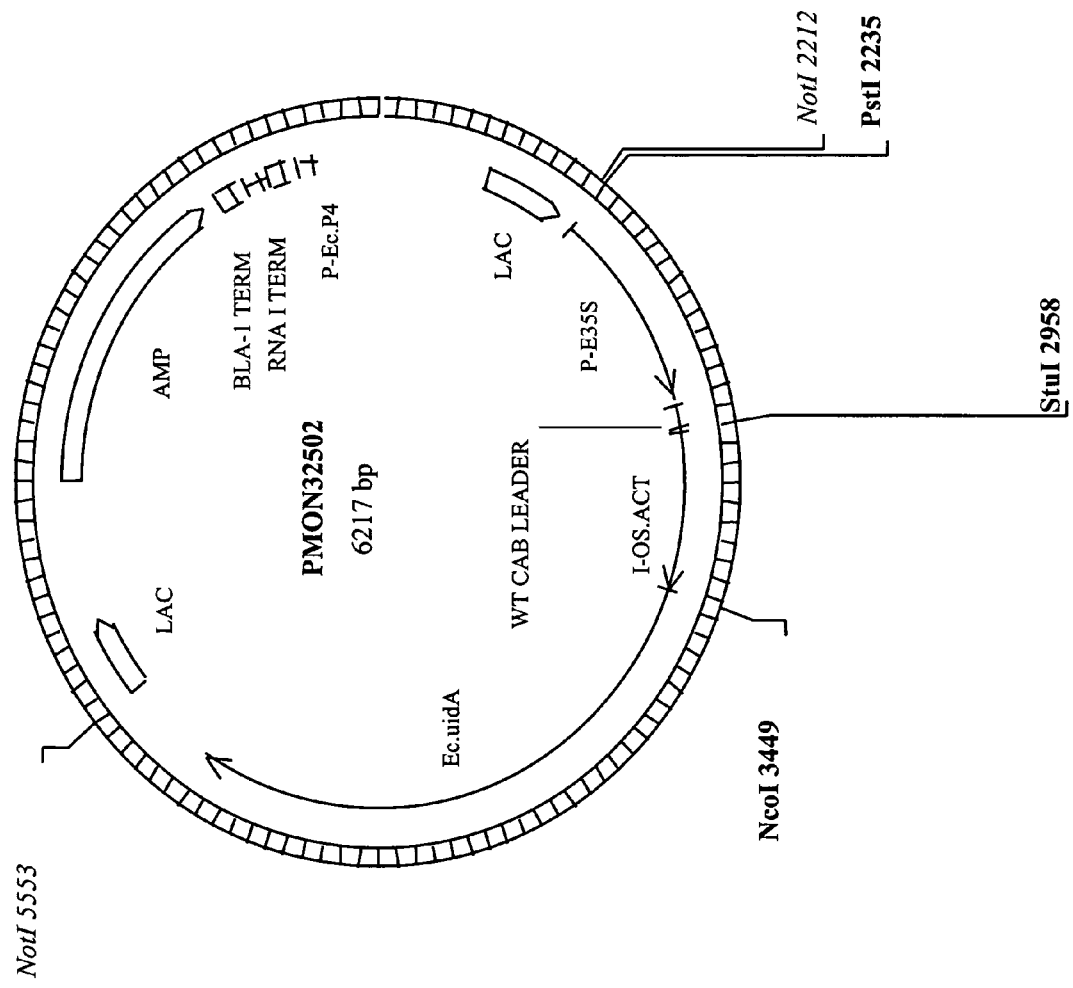
FIG. 4. Shown is a map of plasmid pMON32502.
Figure 5:
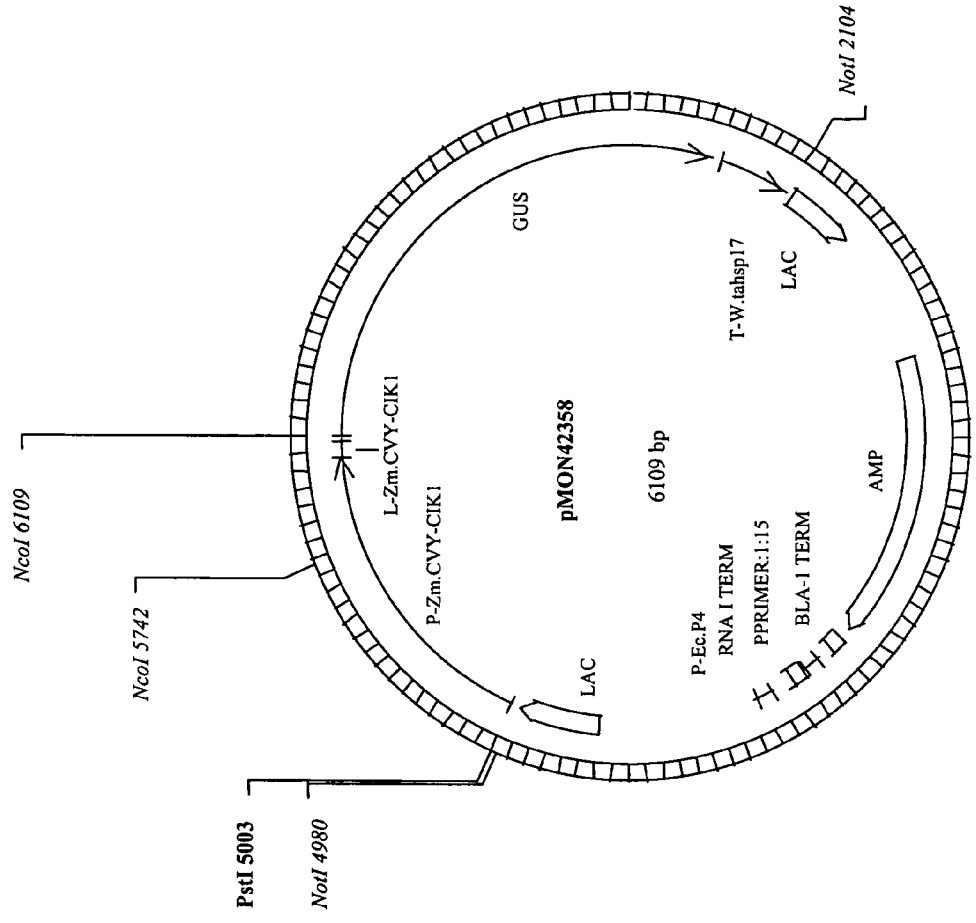
FIG. 5. Shown is a map of plasmid pMON42358.

In order to clone the CVY-CIK1 promoter (SEQ ID NO: 17) (with the endogenous 5'UTR region removed) into a vector in which it was controlling the expression of the GUS reporter gene, digest pMON42357 with PstI and NcoI (a partial digest is required for NcoI since an NcoI site is present within the CVY-CIK1 promoter), gel purify the promoter fragment, and ligate into the backbone of pMON32502 (FIG. 4) which was previously digested with NcoI and PstI to remove the e35S promoter and rice actin introns from this construct. Ligate the CVY-CIK1 promoter (without intron) into the digested pMON32502 backbone using the Roche Rapid DNA ligation kit as directed by the manufacturer to produce pMON42358 (FIG. 5).

After sequencing of the CVY-CIK1 promoter cloned using the PCR reactions above, a base change was detected when compared to the sequence isolated from genomic DNA for the CVY-CIK1 promoter (which included the endogenous intron) in pMON42355. This base change was incorporated by oligo JA01-25 (sequence listed above). This oligonucleotide was initially designed and ordered using the CVY-CIK1 sequence available from the cDNA sequence. When the genomic sequence for this entire promoter was sequenced, the one base pair change was noticed. This was likely due to a sequence error in the cDNA. To make the CVY-CIK1 promoter match the sequence from the genomic DNA, PCR was performed using pMON42358, along with oligos JA01-22 (listed earlier) and JA01-42.

```
                                                          (SEQ ID NO: 7)
JA01-42: agc cat ggC TTC CGA CAG ATG AAG GTT ACT
GTG AAC CTT CAG GCT ATT CTC TTC CAA CAC
```

(in oligo JA01-42, the lower case letters add a NcoI site to the end of the PCR product for cloning purposes. The underlined base pair is the base that is changed in this oligo to correct the sequence of the CVY-CIK1 promoter without an intron to reflect the sequence from the genomic clone, described above.)

The PCR reaction was conducted using the Roche High Fidelity PCR Kit essentially as described by the manufacturer.

| DNA | 1.0 ul |
|---|---|
| 10 mM dNTP mix | 2.0 ul |
| 10 uM JA01-22 | 3.0 ul |
| 10 um JA01-42 | 3.0 ul |
| 10× reaction buffer | 10.0 ul |
| enzyme mix | 0.75 ul |
| water | 80.25 ul |

Cycling Conditions:

| 1. 94 degrees C. | 2 minutes |
|---|---|
| 2. 94 degrees C. | 15 seconds |
| 3. 65 degrees C. | 30 seconds |
| 4. 72 degrees C. | 1 minute and 30 seconds |
| 5. repeat steps 2-4 for a total of 10 times | |
| 6. 94 degrees C. | 15 seconds |
| 7. 65 degrees C. | 30 seconds |
| 8. 72 degrees C. | 1 minute and 30 seconds |
| 9. repeat steps 6-8 for a total of 15 times | |
| 10. 72 degrees C. | 7 minutes |
| 11. 6 degrees C. | hold |

Figure 6:
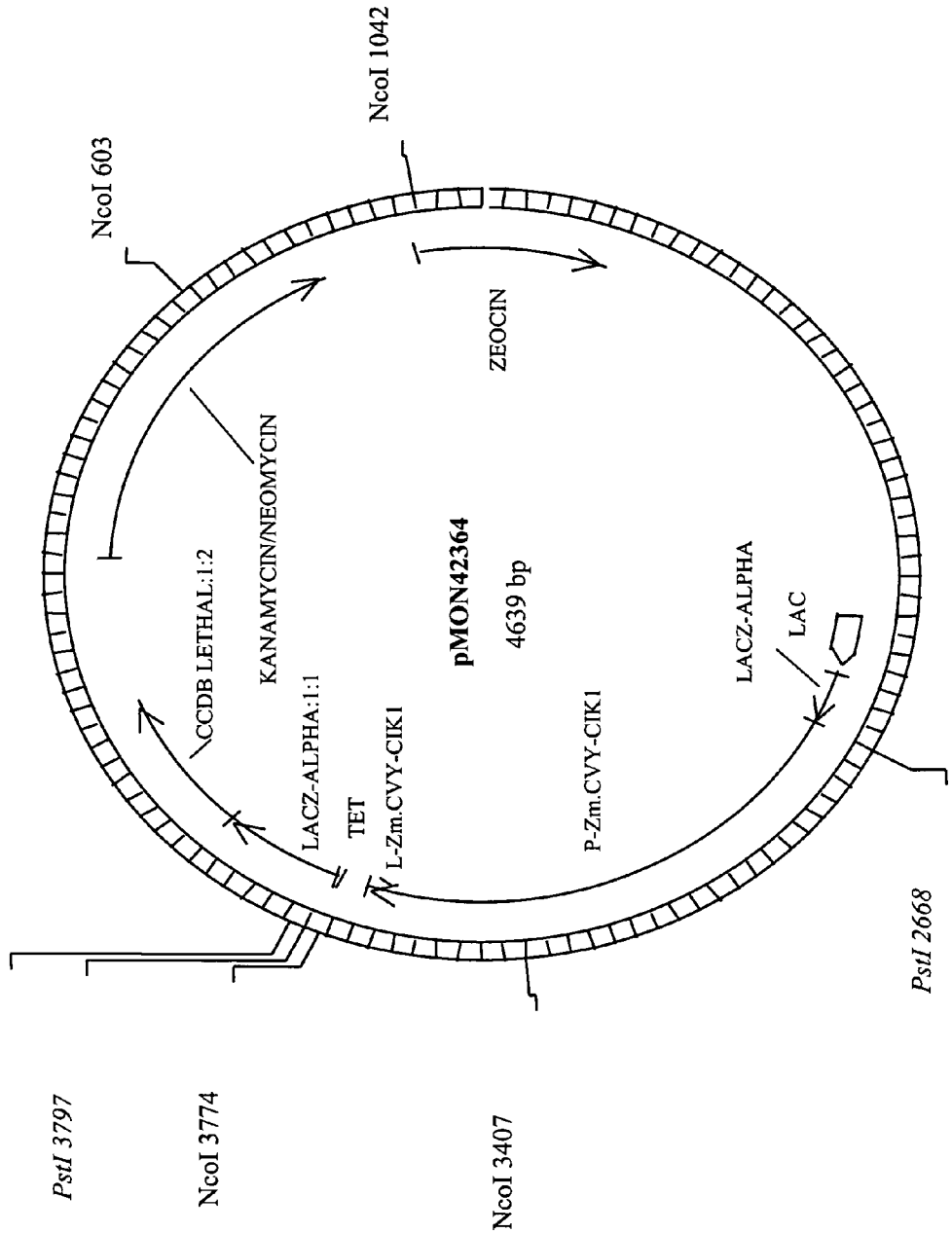
FIG. 6. Shown is a map of plasmid pMON42364.
Figure 7:
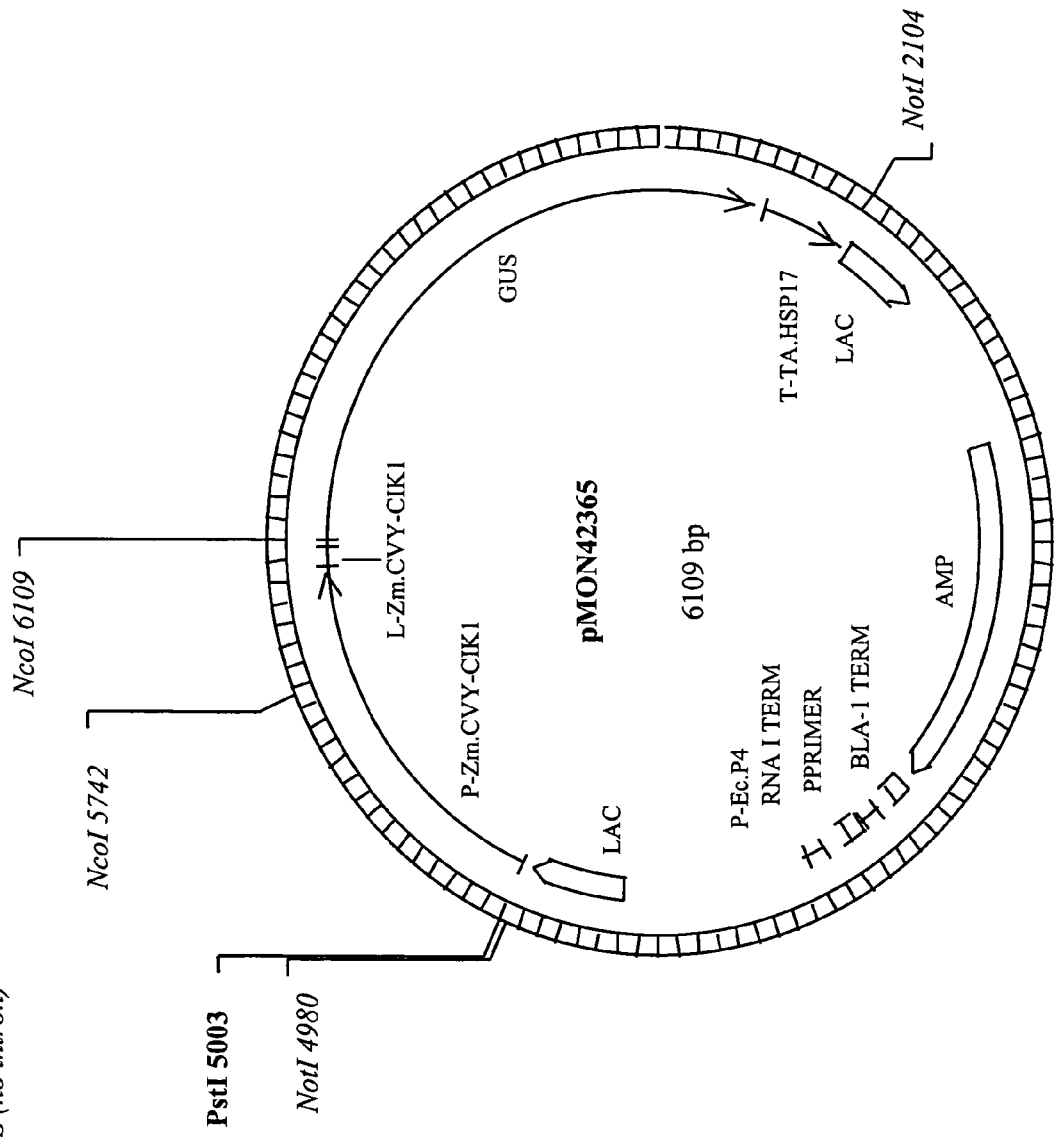
FIG. 7. Shown is a map of plasmid pMON42365.

Gel purify the expected PCR product, and ligate into pCR-BluntII TOPO from Invitrogen (Zero Blunt TOPO PCR cloning Kit, cat. #K2800-20) as directed by the manufacturer to produce pMON42364 (FIG. 6). This corrected CVY-CIK1 sequence was then cut out of pMON42364 by digesting the plasmid with NcoI and PstI and gel purifying the promoter fragment from the rest of the plasmid (a partial digest was necessary with NcoI since it cuts in the interior of the promoter, as well as on the end). This was then ligated into a pMON32502 (FIG. 4) backbone that was also cut with NcoI and PstI as described above to remove the e35S promoter and rice actin intron from this construct. The DNA fragments were ligated using the Roche Rapid DNA ligation kit essentially as described by the manufacturer to produce pMON42365 (FIG. 7).

In order to further compare the effect of an intron on this promoter, a partial clone of the CVY-CIK1 promoter from pMON42364 was placed into a pMON32502 backbone which has been cut with StuI and NcoI to remove only the e35S promoter, but which leaves rice actin intron in the plasmid. In order to do this, use the CVY-CIK1 promoter isolated from pMON42364 via NcoI and PstI digestion, was ligated to pMON32502 backbone digested with PstI and StuI, using the Roche Rapid DNA ligation kit. This reaction should ligated together only the PstI digested end of the 32502 backbone and the PstI digested end of the CVY-CIK1 promoter (FIG. 20). This ligation of the PstI ends inserted the promoter into the backbone in the correct orientation in order to control the expression of the GUS reporter gene. To finish ligating the promoter fragment into the backbone, the partial ligation product was treated with Mung Bean Nuclease (from Invitrogen, cat # 18041-012) as follows:

1. dilute the nuclease to 1 U/ul with 1× reaction buffer supplemented with 0.001% Triton X-100,
2. Mix together:

| Partially ligated DNA | 21 ul |
|---|---|
| 10× nuclease buffer | 5 ul |
| 0.05% Triton X-100 | 1 ul |
| diluted nuclease (1 U/ul) | 1 ul |
| water | 22 ul |

1. Incubate at 30 degrees C. for 20 minutes,
2. Purify the DNA using the PCR purification kit from Qiagen (catalog #28104) as directed by the manufacturer. Elute in 30 ul 10 mM Tris-HCl (from kit)
3. Self-ligate the DNA with the Rapid DNA ligation kit from Roche:

| DNA | 8 ul |
|---|---|
| 5× dilution buffer | 2 ul |
| 2× ligation buffer | 10 ul |
| T4 DNA ligase | 1 ul |

Incubate at room temperature for 15 minutes.

Figure 8:
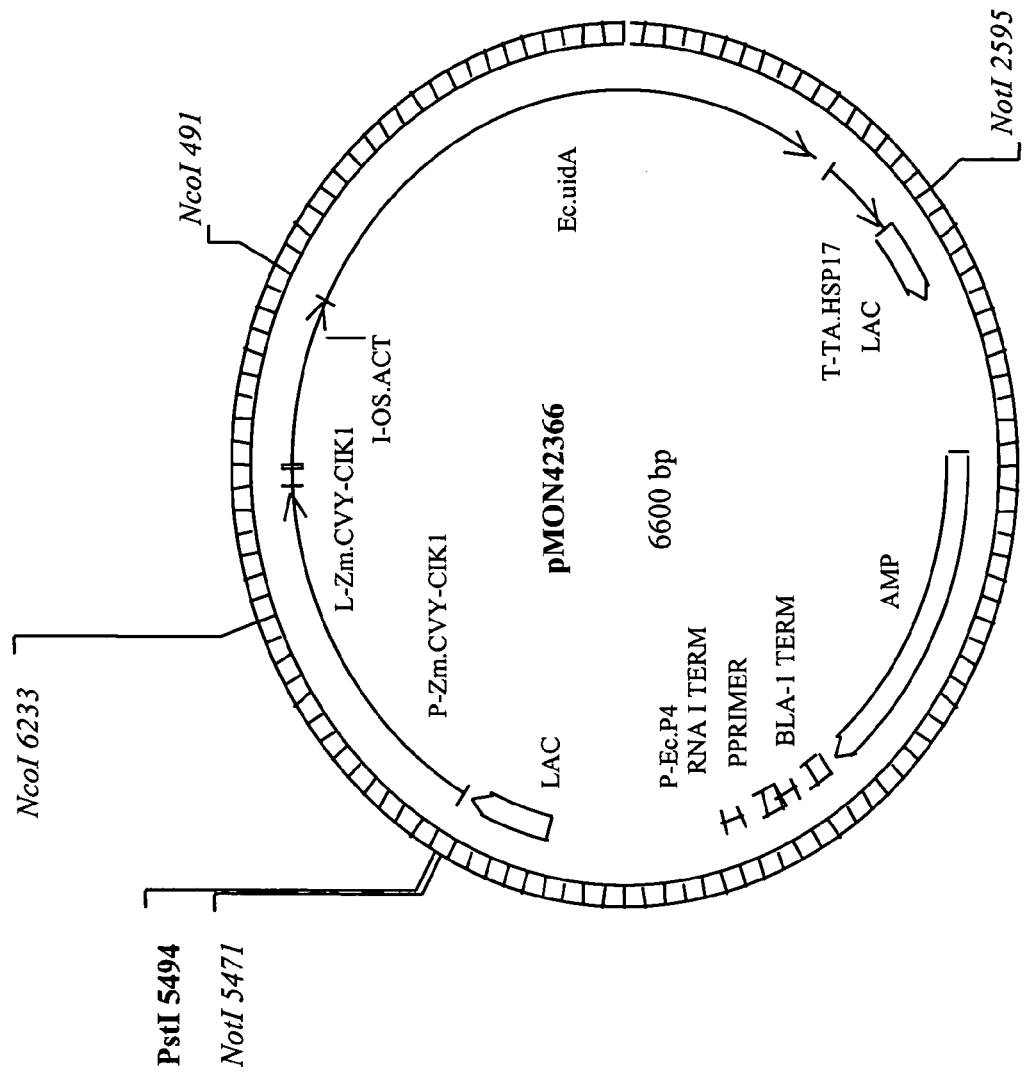
FIG. 8. Shown is a map of plasmid pMON42366.

6. Transformed into DH5α *E. coli* from Invitrogen (max. efficiency, catalog #18258-012) as directed to produce pMON42366 (FIG. 8).

Example 3

Creation of a GUS Reporter Construct Driven by CVY-CIK1 Promoter with Endogenous Intron and 5' UTR (SEQ ID NO: 1)

Figure 9:
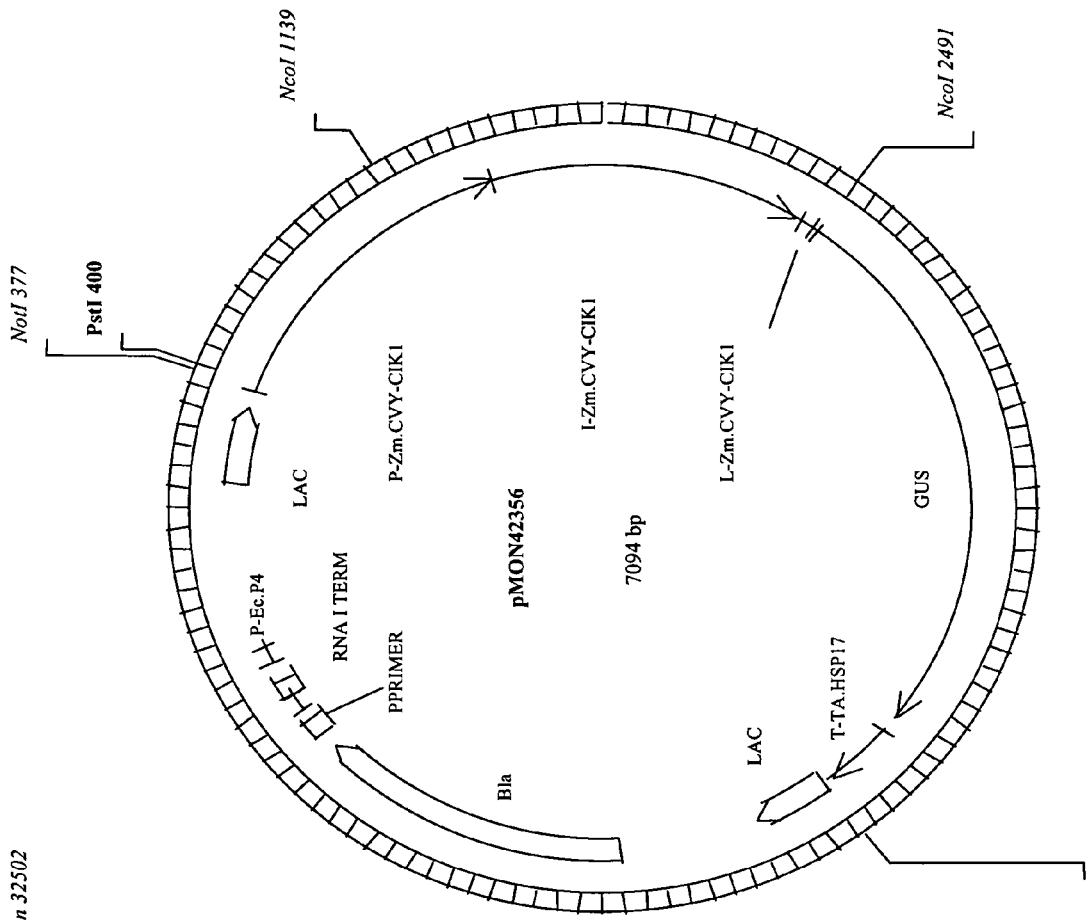
FIG. 9. Shown is a map of plasmid pMON42356.

The CVY-CIK1 promoter fragment (with endogenous intron; SEQ ID NO: 1) in pMON42355 is flanked by restriction sites for NcoI and PstI. The promoter was from pMON42355 using these restriction sites and cloned into a separate vector in which it will be operably liked to the coding region for the GUS reporter gene. However, there is also an NcoI restriction site in the interior of the CVY-CIK1 promoter region, as well as on the end, so a partial digest was performed to avoid cutting on the interior restriction site. The isolated fragment was then ligated into the backbone of pMON32502, which was also cut with NcoI and PstI, in order to remove the e35S promoter and rice actin intron from the construct (which will be replaced by the CVY-CIK1 promoter and intron to make pMON42356 (FIG. 9).

Digestion of pMON42355 to isolate the CVY-CIK1 promoter and intron:

1. Digest pMON42355 DNA with PstI restriction enzyme (Invitrogen, cat #15215-015) and restriction buffer 2 (Invitrogen) at 37 degrees C. for 30 minutes (perform four side-by-side reactions: A, B, C, and D).
2. To each of the four reactions in step one above, add 1 ul of a 1/100 dilution of NcoI (Invitrogen, cat #15421-019). Incubate each at 37 degrees C. Stop reaction A after 30 minutes by adding 1 ul of 0.5M EDTA and heating to 65 degrees C. for 10 minutes. Stop reaction B after 40 minutes, reaction C after 50 minutes, and reaction D after 60 minutes.

3. Run each reaction on an agarose gel, and gel purify the expected approximately 2.1 kb fragment using the Qiagen Gel Purification kit as directed by the manufacturer.

For the pMON32502 digest, remove the e35S promoter and rice actin intron from the construct through digesting with PstI and NcoI as well. Gel purify the approximately 5.0 kb backbone fragment using the Qiagen Gel Purification kit as directed.

To produce pMON42356, ligate the isolated CVY-CIK1 promoter (with intron fragment) isolated above with the pMON32502 backbone fragment using the Roche Rapid DNA ligation kit as directed by the manufacturer.

Figure 10:
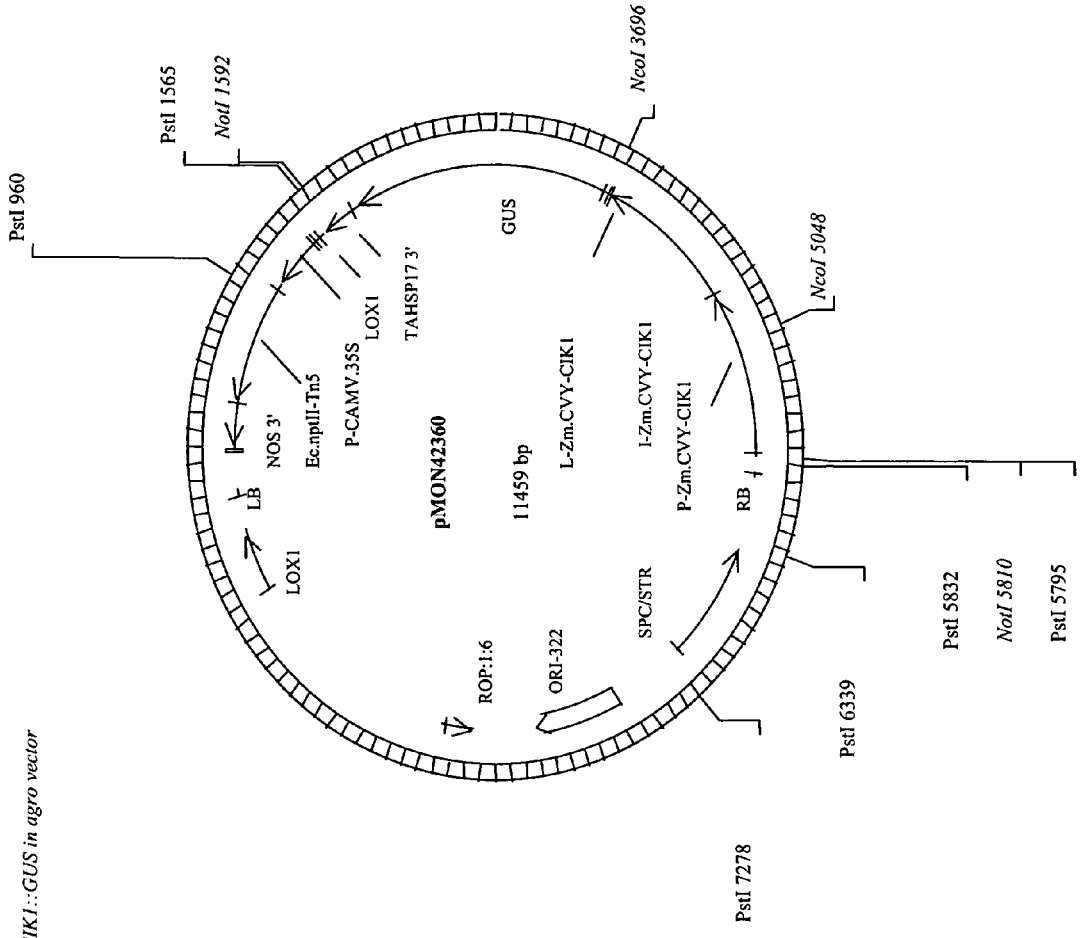
FIG. 10. Shown is a map of plasmid pMON42360.

The CVY-CIK1 (with intron)::GUS cassette in pMON42356 was then transferred into a corn transformation backbone. To do this, isolate the promoter-GUS cassette from pMON42356 by digesting the plasmid with the NotI restriction enzyme and gel purify the fragment as described earlier. Ligate this fragment into the backbone of pMON36176 which has been linearized by digesting with NotI. Before using in the ligation reaction, the linearized pMON36176 backbone was treated with Shrimp Alkaline Phosphatase from Roche (cat #1758250) as directed by the manufacturer to prevent self re-ligation. Ligate using the Roche rapid DNA ligation kit as directed by the manufacturer to produce pMON42360.

pMON42360 (FIG. 10) was then electroporated into *Agrobacterium* cells (ABI strain) to be used for stable corn transformation.

Example 4

A comparison of the expression of the cloned GUS reporter gene from the CVY-CIK1 promoter discussed above was done to the endogenous CVY-CIK1 gene. The expression data are shown in FIG. 13.

To determine if the cloned CVY-CIK1 promoter region (with endogenous 5'UTR intron; SEQ ID NO: 1) is regulated in the same manner as the endogenous CVY-CIK1 promoter, a Northern blot was performed using RNA from corn plants transformed with pMON42360. This construct contains the CVY-CIK1 promoter and intron driving the GUS reporter gene. Transformation could be accomplished by methods known in the art.

Two probes are used to hybridize to two identical Northern blots—one for the endogenous CVY-CIK1 gene (using a probe designed against the CVY_CIK1 3'UTR) and one for the GUS reporter gene (to detect the expression pattern of the cloned promoter fragment).

For this experiment, two leaf fragments were cut from three independent transformed R0 corn plants, as well as a non-transformed C control plant. All of the leaf pieces were floated on several milliliters of 1×MS (dilution of 10×MS media from Sigma, catalog #M-0529) plant tissue culture media in separate wells of several six well tissue culture plates. To check for cold responsiveness of the cloned and endogenous CVY-CIK1 promoters, one of the leaf pieces from each plant was then incubated (on the tissue culture media) for 17 hours in the dark at 13 degrees C. The other leaf piece from each plant was incubated similarly for 17 hours in the dark, but at 30 degrees C. After the incubation period, the edges of the leaf pieces which were initially cut to remove the leaf from the plant were trimmed back again to eliminate the old wound site from the tissue, and the remaining leaf sample was flash frozen in liquid nitrogen, and stored at −80 degrees C. RNA was extracted from these samples as described herein. For Northern blotting, 15 ug of each RNA sample was run on formaldehyde gel as described herein, and blotted onto a nylon membrane. Two identical blots were produced.

To produce a radiolabeled probe for the endogenous CVY-CIK1 gene, the 3'UTR region of the gene was first PCR amplified from a corn EST clone using oligos JA01-35 TGA ACT TTC CAC TGG ACG G (SEQ ID NO: 8) and JA01-36 TGA AGT AAT ACA TCA TCG AAC A (SEQ ID NO: 9). The PCR reaction was performed using Taq DNA polymerase from Roche (cat #1146165) with PCR grade deoxynucleotides from Roche as well (cat #1969064). The reaction was set up as follows:

| | |
|---|---|
| DNA template | 1.0 ul |
| 10 mM dNTP | 1.0 |
| 10 uM oligo JA01-35 | 1.5 |
| 10 um oligo JA01-36 | 1.5 |
| 10× reaction buffer | 5.0 |
| Taq enzyme | 0.5 |
| Water | 39.5 |

Additionally, to make a probe against a portion of the GUS coding region, to check the expression pattern of the transgene, a PCR reaction was completed as above, using pMON42360 as a template and oligos JA00-27 AAC CGT TCT ACT TTA CTG GC (SEQ ID NO: 10) and JA00-30 CAT TGA CGC AGG TGA TCG GA (SEQ ID NO: 11).

The cycling conditions for both of these reactions were as follows:

| | | |
|---|---|---|
| 1. | 94 degrees C. | 2 minutes |
| 2. | 94 degrees C. | 15 seconds |
| 3. | 51 degrees C. | 30 seconds |
| 4. | 72 degrees C. | 1 minute |
| 5. | repeat steps 2-4 for a total of 25 cycles | |
| 6. | 72 degrees C. | 7 minutes |
| 7 | 6 degrees C. | hold |

The PCR products were run out on a 1% agarose gel, and the expected bands were cut out and purified using a Qiagen gel purification kit as directed by the manufacturer.

For radiolabeling of CVY-CIK1 and GUS probes, use the Random Primed DNA Labeling Kit from Roche (cat # 1004760) essentially as directed by the manufacturer. Performed two identical reactions, using the purified CVY-CIK1 3'UTR PCR product and the purified GUS PCR product isolated above. 32P labeled dCTP from Amersham (cat #AA0005) was used in these reactions.

The reaction was incubated at 37 degrees C. for 1 hour and stopped by adding 2.0 ul of 0.2M EDTA. The labeled DNA was purified from the unincorporated radionucleotides using the Sephadex G25 spin columns from Roche (cat #1273949).

For hybridization of probes to the nylon membranes, first, the blots were incubated in pre-hybridization solution at 42 C for one hour in a roller bottle (hybridization/pre-hybridization solution consisted of 50% deionized formamide, 6×SSC, 5×Denhardt's solution, 0.2% SDS and 100 ug/ml salmon sperm DNA). After pre-hybridization, replace the pre-hyb solution with fresh hybridization solution (pre-warmed to 42 C) and add radiolabeled probe to a final concentration of $1\times10^6$ CPM/ml of hybridization solution). The roller bottle was incubated overnight at 42 C. After hybridization, the hybridization solution was discarded, and the blot was washed as follows:

A. one quick rinse at room temperature in 2×SSC, 0.5% SDS, B. twice (for 15 minutes each) in 2×SSC, 0.1% SDS at room temperature, C. twice (for 30 minutes each) in 0.1×SSC, 0.1% SDS at 55 C.

After washing, the blot was wrapped in plastic wrap and exposed to X-ray film (Kodak Biomax MS film from Sigma, cat # Z36,300-6) using an intensifying screen for 53 hours at −80 degrees C. The image of the film was scanned into a computer. The results are shown in FIG. 13.

Example 5

Characterization of the Cold Responsiveness of the CVY-CIK1 Corn Promoter, Using the Naturally Operably Linked Gene To more precisely characterize the cold responsiveness of the CVY-CIK1 gene, prepare RNA for a Northern blot from the following tissues in elite corn inbred lines.

A. A roots and shoots (harvested separately) from seedlings grown for 5 days at 25 degrees C. in the dark. Additionally, similar seedlings were grown for 4 days as above, and transferred to 4 degrees C. temperatures for 24 hours before harvest.

B. C roots and shoots (harvested separately) grown at 25 degrees C. in the dark for 5 days in Metro Mix 200 soil mix (from Hummert's) and shocked at 10 degrees C. for the following amounts of time:
  1. 0 hours
  2. 2 hours
  3. 4 hours
  4. 6 hours
  5. 8 hours
  6. 10 hours C. Callus tissue at three different stages of callus development:
  1. callus growing on 100 mg/L paromomycin media
  2. callus growing on media containing MS media, 6-benzoyladenine, paromomycin, and carbenicillin,
  3. callus growing on media containing MS media without 2,4-D, containing paromomycin and carbenicillin.

D. C. roots and shoots (harvested separately) grown at 25 degrees C. in the dark for 5 days in Metro Mix 200 soil mix and shocked for approximately 22 hours at the following temperatures:
  1. 10 degrees C.
  2. 15 degrees C.
  3. 20 degrees C.
  4. 40 degrees C.

E. C leaf and root tissue from plants grown at 25 degrees C. and 60% relative humidity for 20 days in 12-hour light/dark cycles (light intensity of approx. 550 uE during the light cycles). Also, leaf and root tissue from plants grown in this manner, and shocked at 40 degrees C. for 22 hours before harvest.

F. C leaf tissue from a plant at V18 stage (grown in greenhouse conditions-no cold shock)

G. A leaf tissue from plants grown at 25 degrees C. and 60% relative humidity with approximately 550 uE of light during the light cycles of the 12 hour light/dark cycle for 19 days, then treated with one of the following sets of conditions before harvest:
  1. Shifted to continuous low light conditions (approximately 31 uE) for 2 days at 25 degrees C. and harvested
  2. Shifted to continuous low light conditions (approximately 31 uE) for 2 days at 25 degrees C., then shocked at 13 degrees C. for 22 hours, then harvested.

H. A field was planted with corn. The field was allowed to be watered by natural rainfall until three days prior to phenotype (drought stress and other) measurements. Three days prior to collection apportion of the field was flood irrigated (to runoff) . At the time of measurement temperatures were between 90 and 100 degrees fahrenheit (daily highs) and there had been no measurable rainfall for one week. A leaf tissue from the V12 stage of plants grown in the above irrigated and unirrigated portion of the field were collected. Leaf tissue samples were flash frozen in liquid nitrogen. RNA was produced from each sample.

For the blot, 15 ug of each RNA sample was run in a formaldehyde gel as described in a separate example.

To produce a radiolabeled probe for the endogenous CVY-CIK1 gene, the 3'UTR region of the gene was first PCR amplified from a cDNA clone using oligos JA01-35 TGA ACT TTC CAC TGG ACG G (SEQ ID NO: 8) and JA01-36 TGA AGT AAT ACA TCA TCG AAC A (SEQ ID NO: 9). The PCR reaction was performed using Taq DNA polymerase from Roche (cat #1146165) with PCR grade deoxynucleotides from Roche as well (cat #1969064). The reaction was set up as follows:

| DNA template | 1.0 ul |
| --- | --- |
| 10 mM dNTP | 1.0 |
| 10 uM oligo JA01-35 | 1.5 |
| 10 um oligo JA01-36 | 1.5 |
| 10× reaction buffer | 5.0 |
| Taq enzyme | 0.5 |
| Water | 39.5 |

The cycling conditions for this reaction was as follows:

| 1. | 94 degrees C. | 2 minutes |
| --- | --- | --- |
| 2. | 94 degrees C. | 15 seconds |
| 3. | 51 degrees C. | 30 seconds |
| 4. | 72 degrees C. | 1 minute |
| 5. | repeat steps 2-4 for a total of 25 cycles | |
| 6. | 72 degrees C. | 7 minutes |
| 7. | 6 degrees C. | hold |

The PCR product was run out on a 1% agarose gel, and the expected band was cut out and purified using a Qiagen gel purification kit as directed by the manufacturer.

For radiolabeling of the CVY-CIK1 probe, the Random Primed DNA Labeling Kit from Roche (cat # 1004760) was used essentially as directed by the manufacturer. Use the PCR product described above as a template DNA for the labeling reaction. Use 32P labeled dCTP from Amersham (cat #AA0005) in this reaction.

| Purified DNA | 6.0 ul |
| --- | --- |
| dA, dG, and dT mix | 3.0 |

-continued

| | | |
|---|---|---|
| 32P-dCTP | 5.0 | |
| water | 3.0 | |
| reaction mix | 2.0 | |
| Klenow enzyme | 1.0 | |

The reaction was incubated at 37 degrees C. for 1 hour and then stopped by adding 2.0 ul of 0.2M EDTA. Purify the labeled DNA from the unincorporated radionucleotides using the Sephadex G25 spin columns from Roche (cat #1273949). Hybridize essentially as above.

Figure 11:
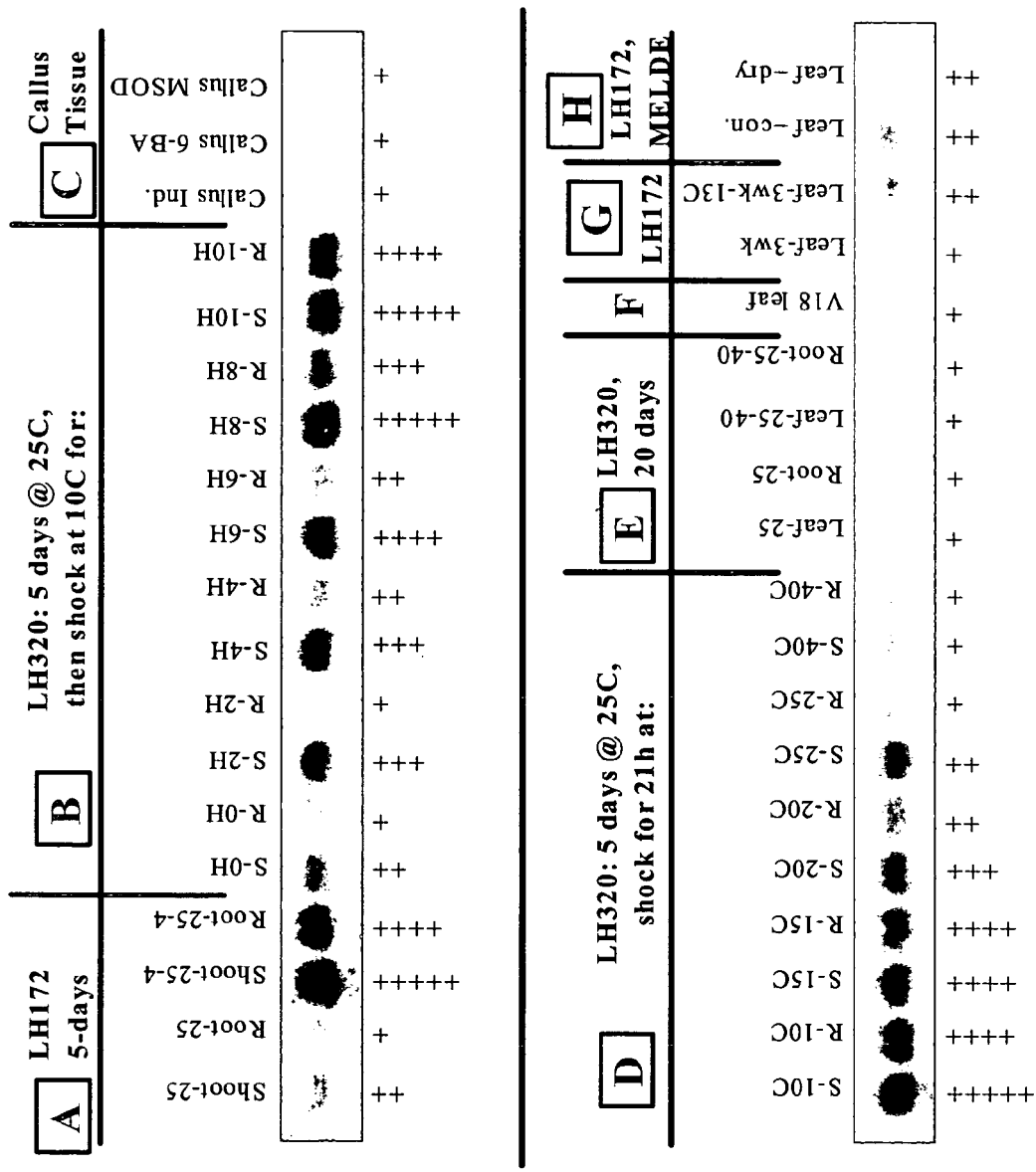
FIG. 11. Northern blot of endogenous CVY-CIK1 gene expression in response to cold. This blot contains RNA from several different treatments of plants, and two different genotypes (15 ug total RNA/lane) as described in the text. The relative band intensity (representing relative strength of expression) of each sample is indicated below each lane. One "+" indicates very low/background levels of expression, while increasing numbers of "+" marks indicate increasing levels of expression.

Relative expression levels are included under each lane of the blot to allow comparison between lanes. These data are shown in FIG. 11.

Example 6

In non-transgenic corn plants the endogenous gene driven by the CVY-CIK1 promoter is transcriptionally up-regulated in cold conditions.

Initial confirmation of the cold responsiveness of the CVY-CIK1 gene was obtained on a Northern blot that contained RNA from LH172 tissue. The RNA on this blot was from tissue that had been treated and harvested as below:

A. A roots and shoots (harvested separately) from seedlings grown for 5 days at 25 degrees C. in the dark in Metro Mix 200. Additionally, similar seedlings were grown for 4 days as above, and transferred to 4 degrees C. temperatures for 24 hours before harvest.

B. A leaf and root tissue from plants grown at 25 degrees C. and 60% relative humidity with approximately 550 uE of light during the light cycles of the 12 hour light/dark cycle for 20 days, then treated in one of the following conditions before harvest:
  i. Shifted to continuous low light conditions (approximately 31 uE) for 2 days at 25 degrees C. and harvested
  ii. Shifted to continuous low light conditions (approximately 31 uE) for 2 days at 25 degrees C., then shocked at 4 degrees C. for 22 hours, then harvested.
  iii. Shifted to continuous low light conditions (approximately 31 uE) for 2 days at 25 degrees C., then shocked at 4 degrees C. for 22 hours, and shifted back to 25 degrees C. for 6 hours before harvest.
  iv. Shifted to continuous low light conditions (approximately 31 uE) for 2 days at 25 degrees C., then shocked at 13 degrees C. for 22 hours, then harvested.
  v. Shifted to continuous low light conditions (approximately 31 uE) for 2 days at 25 degrees C., then shocked at 4 degrees C. for 22 hours, and shifted back to 25 degrees C. for 6 hours before harvest.

The RNA was run and blotted as described in other examples. To produce a probe to hybridize to the blots, the insert from a cDNA clone was amplified using the Faststart Taq Polymerase kit from Roche (cat #2158264) essentially as directed. PCR reaction were set up as follows, using oligos named M13F CCC AGT CAC GAC GTT GTA AAA CG (SEQ ID NO: 12) and M13R AGC GGA TAA CAA TTT CAC ACA GG (SEQ ID NO: 13) to amplify the insert in this vector between the forward and reverse M13 priming sites:

| | | |
|---|---|---|
| Water | 26.6 | ul |
| 10× buffer | 5.0 | |
| GC solution | 10.0 | |
| 10 mM dNTP mix | 1.0 | |
| 10 uM M13F oligo | 3.0 | |
| 10 uM M13R oligo | 3.0 | |
| polymerase | 0.4 | |
| template DNA | 1.0 | |

Use the following cycling conditions:

| | | |
|---|---|---|
| A. | 95 degrees C. | 4 minutes |
| B. | 95 degrees C. | 30 seconds |
| C. | 56 degrees C. | 30 seconds |
| D. | 72 degrees C. | 4 minutes |
| E. | repeat steps B-D for a total of 30 cycles | |
| F. | 72 degrees C. | 7 minutes |
| G. | 4 degrees C. | hold |

15 ul of the PCR product was run on a gel, and the expected size band purified using the Qiagen Gel Purification kit as directed by the manufacturer. This purified DNA was used as the template in a Random Primed Labeling reaction to incorporate 32P labeled dCTP (from Amersham, cat #AA0005) in order to make a radiolabeled probe (Random Primed DNA labeling kit from Roche [cat # 1004760] used essentially as directed by the manufacturer). Hybridization and exposure to film was done essentially as above. This data is shown in FIG. 12.

Example 7

Cloning of the CVY-CIK1 Promoter (with Endogenous Intron) into GUS Transformation Vectors with Selectable Markers for Glyphosate Resistance Vectors for transformation of the CVY-CIK1 promoter (driving the GUS reporter gene) were also constructed in vector backbones that contained selectable markers for glyphosate resistance (using the native bacterial CP4 aroA gene from *Agrobacterium tumefaciens*. For graphic representation of the GUS CVY-CIK1 constructs see FIG. 20.

CVY-CIK1 Promoter with Endogenous Intron (SEQ ID NO: 1):

The CVY-CIK1 (with intron)::GUS cassette in pMON42356 was transferred into a corn transformation backbone with a glyphosate selectable marker. The promoter-GUS cassette from pMON42356 was isolated by digesting the plasmid with the NotI restriction enzyme and the fragment was gel purified using the Qiagen Gel Extraction Kit (cat # 28704). This fragment was ligated into the backbone of pMON53616 which was also digested with NotI to remove the 35S::GOI::HSP17 cassette already in the vector. Before using in the ligation reaction, the linearized pMON53616 backbone was treated with Shrimp Alkaline Phosphatase from Roche (cat #1758250) as directed by the manufacturer to prevent self re-ligation. Ligations were performed using the Roche rapid DNA ligation kit as directed by the manufacturer to produce pMON42377 (FIG. 21).

CVY-CIK1 Promoter (Endogenous Intron Removed) (SEQ ID NO: 17):

The CVY-CIK1 (with endogenous intron removed)::GUS cassette in pMON42365 was transferred into a corn transformation backbone with a glyphosate selectable marker. The promoter-GUS cassette from pMON42365 was isolated by digesting the plasmid with the NotI restriction enzyme and the fragment was gel purified using the Qiagen Gel Extraction Kit (cat # 28704). This fragment was ligated into the backbone of pMON53616 which was also digested with NotI to remove the 35S::GOI::HSP17 cassette already in the vector. Before using in the ligation reaction, the linearized pMON53616 backbone was treated with Shrimp Alkaline Phosphatase from Roche (cat #1758250) as directed by the manufacturer to prevent self re-ligation. Ligations were performed using the Roche rapid DNA ligation kit as directed by the manufacturer to produce pMON42378 (FIG. 22).

CVY-CIK1 Promoter (Endogenous Intron Removed) Combined with the Rice Actin Intron (SEQ ID NO: 16):

The CVY-CIK1 (with endogenous intron removed)::rice actin intron::GUS cassette in pMON42359 was transferred into a corn transformation backbone with a glyphosate selectable marker. The promoter-GUS cassette from pMON42359 was isolated by digesting the plasmid with the NotI restriction enzyme and the fragment was gel purified using the Qiagen Gel Extraction Kit (cat # 28704). This fragment was ligated into the backbone of pMON53616 which was also digested with NotI to remove the 35S::GOI::HSP17 cassette already in the vector. Before using in the ligation reaction, the linearized pMON53616 backbone was treated with Shrimp Alkaline Phosphatase from Roche (cat #1758250) as directed by the manufacturer to prevent self re-ligation. Ligations were performed using the Roche rapid DNA ligation kit as directed by the manufacturer to produce pMON42379 (FIG. 23).

Example 8

Expression of CVY-CIK1 in Hybrid Corn Tissue

All of the experimentation done prior to this example on the CVY-CIK1 cold responsive promoter was done on inbred tissue/RNA. However, it is important to determine if this promoter expresses similarly in hybrid lines as it does in inbred lines. To do this, RNA was isolated from seedlings of two hybrid lines (LH320/LH244 and LH320/HC33) as well as two inbred lines (LH320 and LH244). These seedlings were grown in the dark in soil for four days at 25 degrees C., then half of each line were transferred to a 10 degrees C. shock while the other half remained at 25 degrees C. for an additional 23 hours. Roots and shoots for each were then harvested separately, and RNA was isolated from each tissue set and used to produce a Northern blot. This blot was then hybridized with a DIG-labeled probe made against the 3'UTR region of the CVY-CIK1 gene. The results are included in FIG. 14. The CVY-CIK1 gene appears to be regulated similarly in both inbreds and hybrids—it is cold-responsive in each genotype tested.

Example 9

Evaluation of the CVY-CIK1 Promoter Driving the GUS Reporter Gene in Transgenic R1 Plants Expression in Cold Shocked Seedlings The CVY-CIK1 promoter was submitted for transformation into corn plants in a variety of configurations driving the GUS reporter gene. The first set of plants returned in this effort were transformed with pMON42360 (CVY-CIK1 promoter with an endogenous intron from the 5'UTR of the CVY-CIK1 gene driving the GUS reporter gene). These events were referred to as "YAW" events.

To analyze the cold responsiveness of the cloned promoter region, seeds for several independent events were germinated in moist, rolled paper towels in the dark for three days at 28 degrees C. After the third day, half of the seedlings were transferred to 10 degrees C. overnight (approximately 16 hours) while the other half of the seeds remained at 28 degrees C. as a warm control. After this overnight treatment, the roots and shoots of these plants were harvested separately. Since these events are at the R1 generation, they are still segregating, so each seedling was frozen individually until ELISA analysis identified which were positive and which were negative. The identified positives for each event were then pooled. Total protein was extracted from each pool of samples. Expression of the GUS transgene was analyzed in the warm and cold treated shoot tissue of each event on a Western blot, using a commercial anti-GUS antibody. The results of this shoot Western blot are included in FIG. 15.

Example 10

Analysis of CVY-CIK1 Cold Inducible Promoter in Stable Corn Transformants Using RNA Taqman In order to determine the extent of cold responsiveness of the CVY-CIK1 promoter (with endogenous CIK1 5'UTR intron), plants transformed with pMON42360 were analyzed with and without cold treatment. The transgenics were analyzed at two separate ages, 4 and 10 days. For the 4 day samples, seeds for several independent events were germinated in moist, rolled paper towels in the dark for three days at 28 degrees C. After the third day, half of the seedlings were transferred to 10 degrees C. overnight (approximately 16 hours) while the other half of the seeds remained at 28 degrees C. as a warm control. After this overnight treatment, the roots and shoots of these plants were harvested separately. Since these events are at the R1 generation, they are still segregating, so each seedling was frozen individually until PCR analysis identified which were positive and which were negative. The identified positives for each event were then pooled. For the 10 day samples, plants were grown for 9 days in the greenhouse, then half of the plants were transferred to 10 degrees C. for 21 hours in the dark, while the other half were kept at 25 degrees C. in the dark for the 21 hours. Since these plants are still part of a segregating population, positives were determined through PCR.

Aliquots of tissue for each of these samples were submitted for RNA Taqman analysis using a primer/probe set for the HSP17 terminator (see Table 8). The results for the 4 day samples are included below in FIGS. 16 and 17. The cloned CIK1 promoter appears to be up-regulated in all of the 4 day old samples (root and shoot) in response to cold treatment. In the shoot samples, this up-regulation ranged from 1.5 fold to 25 fold compared to the warm treated sample from the same event. In the root tissues, the up-regulation ranged from a 1.5-11.5 fold increase. Two replicates of each tissue were initially submitted for analysis, and a third was submitted later. The combined data for all of the replicates is described in example 11. The Taqman data indicates that this promoter appears to express more strongly in shoot tissue than in root tissue, which matches the results seen on a Northern blot of the endogenous CVY-CIK1 gene on non-transgenic tissue described in earlier summaries.

In order to determine the level of cold responsiveness of this promoter in older tissues, similar experiments were done on greenhouse grown plants. Several plants per event were grown for 9 days in the greenhouse. After day nine, half of them were transferred to a dark Percival chamber set at 10 degrees C. These plants were also watered with pre-chilled water to rapidly drop the temperature of the soil. The other half of the plants were transferred to a dark Percival set at 25 degrees C. Both of these treatments were for approximately 21 hours. Leaf and root samples were collected after the treatments and submitted for RNA Taqman analysis. The results are included below in FIGS. 18 and 19. In short, three of the four events showed an increase in CIK1 promoter activity in the leaf in response to cold shock, while only one of the events showed a cold response in the root tissue. In leaves, the fold change in expression in response to cold ranged from 0.45× to 12.8×, while in the root, the values ranged from 0.27 to 1.97 fold changes in response to exposure to cold temperatures. Two plants were sampled from each event.

Example 11

Taqman Analysis of Cold Inducible Promoter Candidates

Expression of the endogenous CVY-CIK1 gene was examined via RNA Taqman using RNA isolated from a variety of different tissue types and growth conditions. Expression was analyzed in RNA samples from 70 different tissues (listed below), including a cold time course in LH320, cold shock tissues from other genotypes, and tissues to test the drought response and expression in callus tissues. The cold time course involved germinating LH320 corn seedlings for four days in the dark at 25 degrees Celsius, and then transferring the seedlings to 10 degrees for 0, 2, 4, 6, 8, 10, and 21 hours. Also included were samples that were cold shocked at 10 degrees for 4 and 7 days to assay long-term cold induction. Primers for each gene were analyzed by BLAST to ensure specificity to the gene of interest and minimize the possibility of cross hybridization to closely related paralogs.

RNA Used for Taqman

Seeds from a variety of different corn genotypes (inbred and hybrid) were grown to various stages for RNA extraction. These are listed in Table 1. Seeds were germinated in Metro Mix 200 soil in three inch peat pots (from Hummerts International). Each pot contained osmocoat slow release fertilizer (19% total nitrogen, 6% available phosphate, 12% potash). Tissues were harvested in liquid nitrogen, and RNA was extracted.

Taqman analysis was conducted using an ABI Prism® 7900 Sequence Detection System (Product # 4331406) and the standard protocols supplied by the manufacturer (Applied Biosystems; Foster City, Calif.). Quantitative RNA measurements are relative to a standardized control, and therefore unitless. A primer/probe set for 18S rRNA was used in each reaction as a control.

TABLE 1

| Genotype | Age/stage | Tissue Type | Treatment |
|---|---|---|---|
| LH320 | 5 days old | Root | in dark, 5 days@25 C. |
| LH320 | 5 days old | shoot | in dark, 5 days@25 C. |
| LH320 | 5 days old | Root | in dark, 4 days@25 C.; shock 2 hours@10 C. |
| LH320 | 5 days old | shoot | in dark, 4 days@25 C.; shock 2 hours@10 C. |
| LH320 | 5 days old | Root | in dark, 4 days@25 C.; shock 4 hours@10 C. |
| LH320 | 5 days old | shoot | in dark, 4 days@25 C.; shock 4 hours@10 C. |
| LH320 | 5 days old | Root | in dark, 4 days@25 C.; shock 6 hours@10 C. |
| LH320 | 5 days old | shoot | in dark, 4 days@25 C.; shock 6 hours@10 C. |
| LH320 | 5 days old | Root | in dark, 4 days@25 C.; shock 8 hours@10 C. |
| LH320 | 5 days old | shoot | in dark, 4 days@25 C.; shock 8 hours@10 C. |
| LH320 | 5 days old | Root | in dark, 4 days@25 C.; shock 10 hours@10 C. |
| LH320 | 5 days old | shoot | in dark, 4 days@25 C.; shock 10 hours@10 C. |
| LH320 | 5 days old | Root | in dark, 4 days@25 C., shock for 21 hours@10 C. |
| LH320 | 5 days old | shoot | in dark, 4 days@25 C., shock for 21 hours@10 C. |
| LH320 | 5 days old | Root | in dark, 4 days@25 C., shock for 21 hours@15 C. |
| LH320 | 5 days old | shoot | in dark, 4 days@25 C., shock for 21 hours@15 C. |
| LH320 | 5 days old | Root | in dark, 4 days@25 C., shock for 21 hours@20 C. |
| LH320 | 5 days old | shoot | in dark, 4 days@25 C., shock for 21 hours@20 C. |
| LH320 | 5 days old | Root | in dark, 4 days@25 C., shock for 21 hours@40 C. |
| LH320 | 5 days old | shoot | in dark, 4 days@25 C., shock for 21 hours@40 C. |
| LH320 | 20 days old | Leaf | grow in GC, 20 days@25 C. (12 hour light/dark) |
| LH320 | 20 days old | Root | grow in GC, 20 days@25 C. (12 hour light/dark) |
| LH320 | 20 days old | Leaf | grow in GC, 20 days@25 C. (12 hour light/dark), shock 24 hours at 40 C. |
| LH320 | 20 days old | Root | grow in GC, 20 days@25 C. (12 hour light/dark), shock 24 hours at 40 C. |
| LH320 | V18 plant | Leaf | pool of V18 leaf tissue from 5 LH320 plants grown in GH |
| LH320 | callus induction | callus | tissue from 1 g of callus growing on callus induction media |
| LH320 | callus 6-BA | callus | tissue from 1 g of callus growing on 6-benzyladenine media |
| LH320 | callus MSOD | callus | tissue from 1 g of callus growing on plant regeneration media |
| LH172 | 5 days old | Root | in dark, 4 days@25 C. |
| LH172 | 5 days old | shoot | in dark, 4 days@25 C. |
| LH172 | 5 days old | Root | in dark, 4 days@25 C., shock for 24 hours@4 C. |
| LH172 | 5 days old | shoot | in dark, 4 days@25 C., shock for 24 hours@4 C. |
| LH172 | 21 days old | Leaf | grow in GC, 21 days@25 C. |
| LH172 | 21 days old | Root | grow in GC, 21 days@25 C. |
| LH172 | 21 days old | Leaf | grow in GC, 21 days@25 C., shock for 21 hours@4 C. |
| LH172 | 21 days old | Root | grow in GC, 21 days@25 C., shock for 21 hours@4 C. |
| LH172 | 21 days old | Leaf | grow in GC, 21 days@25 C., shock for 21 hours@4 C., return to 25 C. for 6 hours |
| LH172 | 21 days old | Root | grow in GC, 21 days@25 C., shock for 21 hours@4 C., return to 25 C. for 6 hours |
| LH172 | 21 days old | Leaf | grow in GC, 21 days@25 C., shock for 21 hours@13 C. |

TABLE 1-continued

| Genotype | Age/stage | Tissue Type | Treatment |
|---|---|---|---|
| LH172 | 21 days old | Root | grow in GC, 21 days@25 C., shock for 21 hours@13 C. |
| LH172 | 21 days old | Leaf | grow in GC, 21 days@25 C., shock for 21 hours@13 C., return to 25 C. for 6 hours |
| LH172 | 21 days old | Root | grow in GC, 21 days@25 C., shock for 21 hours@13 C., return to 25 C. for 6 hours |
| LH59 | V7 | Leaf | V7 leaf collected 1 day after watering |
| LH59 | V7 | Leaf | V7 leaf collected 8 days after watering (moderate drought) |
| LH244 | 5 days old | Root | in dark, 5 days@25 C. |
| LH244 | 5 days old | shoot | in dark, 5 days@25 C. |
| LH244 | 5 days old | Root | in dark, 5 days@25 C., shock for 22 hours@10 C. |
| LH244 | 5 days old | shoot | in dark, 5 days@25 C., shock for 22 hours@10 C. |
| Wigor | 5 days old | Root | in dark, 5 days@25 C. |
| Wigor | 5 days old | shoot | in dark, 5 days@25 C. |
| Wigor | 5 days old | Root | in dark, 5 days@25 C., shock for 22 hours@10 C. |
| Wigor | 5 days old | shoot | in dark, 5 days@25 C., shock for 22 hours@10 C. |
| LH195 | 5 days old | Root | in dark, 5 days@25 C. |
| LH195 | 5 days old | shoot | in dark, 5 days@25 C. |
| LH195 | 5 days old | Root | in dark, 5 days@25 C., shock for 22 hours@10 C. |
| LH195 | 5 days old | shoot | in dark, 5 days@25 C., shock for 22 hours@10 C. |
| LH320xHC33 | 5 days old | Root | in dark, 5 days@25 C. |
| LH320xHC33 | 5 days old | shoot | in dark, 5 days@25 C. |
| LH320xHC33 | 5 days old | Root | in dark, 5 days@25 C., shock for 22 hours@10 C. |
| LH320xHC33 | 5 days old | shoot | in dark, 5 days@25 C., shock for 22 hours@10 C. |
| LH320xLH244 | 5 days old | Root | in dark, 5 days@25 C. |
| LH320xLH244 | 5 days old | shoot | in dark, 5 days@25 C. |
| LH320xLH244 | 5 days old | Root | in dark, 5 days@25 C., shock for 22 hours@10 C. |
| LH320xLH244 | 5 days old | shoot | in dark, 5 days@25 C., shock for 22 hours@10 C. |
| LH320 | 4 days old | Root | in dark, 4 days@25 C. |
| LH320 | 4 days old | shoot | in dark, 4 days@25 C. |
| LH320 | 7 days old | Root | in dark, 3 days@25 C., shock for 4 days@13 C. |
| LH320 | 7 days old | shoot | in dark, 3 days@25 C., shock for 4 days@13 C. |
| LH320 | 10 days old | Root | in dark, 3 days@25 C., shock for 7 days@13 C. |
| LH320 | 10 days old | shoot | in dark, 3 days@25 C., shock for 7 days@13 C. |

Treatment of RNA with DNAse Prior to Use in Taqman Assays

Before it was used for Taqman, the RNA produced above needed to be treated with DNAse to remove any possibly contaminating amounts of genomic DNA that may remain. To do this, the DNA-free kit from Ambion (cat #1906) was used essentially as described by the manufacturer. Approximately 15 ug of RNA for each DNAse reaction. After DNAse treatment, ethanol precipitate the RNA:
1. Add 2.5 volumes of 100% ethanol, and 0.1 volume of nuclease free 5M Ammonium Acetate (Ambion cat # 9070G).
2. Incubate at −20 C for 30 minutes.
3. Centrifuge at top speed for 15 minutes at 4 C
4. Wash pellet in 75% EtOH, spin at 4 C for 5 minutes.
5. Air-dry pellet briefly, resuspend in 30 ul of nuclease free water (Ambion Cat #9938).
6. Quantitate RNA on spectrophotometer.

After ethanol precipitation, the absence of DNA contamination was confirmed by performing standard PCR on the RNA prep using oligos and conditions for an endogenous corn gene, alongside of a control reaction using genomic DNA as the template.

Real-Time TaqMan RT-PCR

Real-time TaqMan expression assays of cold inducible promoters were carried out on an ABI 7900HT Sequence Detection System (Applied Biosystems, Foster City, Calif.). The pairs of forward and reverse primers and TaqMan probes for the target genes were designed using Primer Express software (version 2.0.0, Applied Biosystems). BLAST (Basic Local Alignment Tool, NCBI) sequence comparison of the primer and probe sequences to the entire Monsanto corn Unigene sequence collection was done to ensure specificity to the target gene and avoid possible cross hybridization to highly similar, but not identical sequences. Primers/probes that matched 100% to genes other than the target gene were not used. The TaqMan probes for target genes contained FAM reporter at the 5' end and TAMRA quencher at the 3' end were synthesized by Integrated DNA Technology (Coralville, Iowa). Ribosomal 18S RNA was chosen to be endogenous control in the multiplex reaction contained VIC reporter at the 5' end and TAMRA quencher at the 3' end. 18S VIC probe was synthesized by Applied Biosystems (Foster city, CA) (primers described in Table 2 and 7). Each primer/probe sets was validated by standard curve analysis by TaqMan runs using serial diluted total RNA or EST clone DNA contained the specific amplicom sequences.

For the RT-PCR reaction, the TaqMan One-Step RT-PCR Master Mix Reagents Kit (Applied Biosystems) was used: 300 nM forward primer, 300 nM reverse primer and 200 nM TaqMan FAM probe for target genes, and 50 nM forward primer, 50 nM reverse primer and 50 nM TaqMan VIC probe for endogenous control 18S. 40 ng each of DNA-free total RNA samples were added to the reaction with a total volume of 10 ul. Amplification and signal detection were performed using the ABI 7900HT Sequence Detection System (Applied Biosystems) with the following profile: 1 cycle at 50° C. for 30 min, 1 cycle at 95° C. for 10 min, and 40 cycles each at 95° C. for 15 sec and 56° C. for 1 min.

Samples were deemed positive at any given cycle when the value of the emitted fluorescence was greater than the threshold value calculated by the instrument's software (SDS 2.0). The threshold cycle (Ct) is defined as the cycle at which PCR amplification reaches the threshold value. The relative expression of each mRNA was calculated by the $\Delta\Delta Ct$ method relative to endogenous control 18S. Data are expressed as a ratio of target mRNA to 18S. Studies were conducted in duplicate and data are shown as mean values.

These are the Taqman primer/probe sets used to examine the expression pattern of the endogenous CVY-CIK1 gene.

TABLE 2

| Gene ID | Oligo Function | Oligo ID and Position | Oligo Sequence |
|---|---|---|---|
| CVY-CIK1 | Forward primer | CVY-CIK1-825F | TATCTGGTCTTGCGGAGTAATCC (SEQ ID NO: 19) |
| | Reverse primer | CVY-CIK1-907R | TGTATAGGGCGATGATGTTGTCA (SEQ ID NO: 20) |
| | TaqMan probe | CVY-CIK1-850T | TTTGTTCTTCTTGCTGGATATTTACCTTTCGAGG (SEQ ID NO: 21) |

Taqman Results

The results of the endogenous CVY-CIK1 taqman are included below (Table 3). The results are expressed as relative levels of transcription from sample to sample (each sample was run with two replicates).

TABLE 3

CVY-CIK1 Relative Expression in Cold Treated Samples

| Sample | Genotype, Age/stage, Tissue Type, Treatment | AVG Rel Exp | SD exp |
|---|---|---|---|
| 1 | LH320, 5 days old, root, in dark, 5 days@25 C. | 2.088 | 0.295 |
| 2 | LH320, 5 days old, shoot, in dark, 5 days@25 C. | 3.899 | 0.211 |
| 3 | LH320, 5 days old, root, in dark, 4 days@25 C.; shock 2 hours@10 C. | 1.759 | 0.014 |
| 4 | LH320, 5 days old, shoot, in dark, 4 days@25 C.; shock 2 hours@10 C. | 6.412 | 0.026 |
| 5 | LH320, 5 days old, root, in dark, 4 days@25 C.; shock 4 hours@10 C. | 2.825 | 0.343 |
| 6 | LH320, 5 days old, shoot, in dark, 4 days@25 C.; shock 4 hours@10 C. | 8.779 | 0.526 |
| 7 | LH320, 5 days old, root, in dark, 4 days@25 C.; shock 6 hours@10 C. | 3.720 | 0.222 |
| 8 | LH320, 5 days old, shoot, in dark, 4 days@25 C.; shock 6 hours@10 C. | 12.724 | 1.142 |
| 9 | LH320, 5 days old, root, in dark, 4 days@25 C.; shock 8 hours@10 C. | 3.642 | 0.225 |
| 10 | LH320, 5 days old, shoot, in dark, 4 days@25 C.; shock 8 hours@10 C. | 8.204 | 0.513 |
| 11 | LH320, 5 days old, root, in dark, 4 days@25 C.; shock 10 hours@10 C. | 5.545 | 0.641 |
| 12 | LH320, 5 days old, shoot, in dark, 4 days@25 C.; shock 10 hours@10 C. | 10.850 | 0.886 |
| 13 | LH320, 5 days old, root, in dark, 4 days@25 C., shock for 21 hours@10 C. | 9.345 | 0.006 |
| 14 | LH320, 5 days old, shoot, in dark, 4 days@25 C., shock for 21 hours@10 C. | 16.763 | 3.808 |
| 15 | LH320, 5 days old, root, in dark, 4 days@25 C., shock for 21 hours@15 C. | 4.640 | 0.908 |
| 16 | LH320, 5 days old, shoot, in dark, 4 days@25 C., shock for 21 hours@15 C. | 8.126 | 2.278 |
| 17 | LH320, 5 days old, root, in dark, 4 days@25 C., shock for 21 hours@20 C. | 3.250 | 0.895 |
| 18 | LH320, 5 days old, shoot, in dark, 4 days@25 C., shock for 21 hours@20 C. | 6.781 | 1.212 |
| 19 | LH320, 5 days old, root, in dark, 4 days@25 C., shock for 21 hours@40 C. | 2.118 | 0.355 |
| 20 | LH320, 5 days old, shoot, in dark, 4 days@25 C., shock for 21 hours@40 C. | 3.280 | 0.200 |
| 21 | LH320, 20 days old, leaf, grow in GC, 20 days@25 C. (12 hour light/dark) | 4.276 | 1.059 |
| 22 | LH320, 20 days old, root, grow in GC, 20 days@25 C. (12 hour light/dark) | 1.183 | 0.165 |
| 23 | LH320, 20 days old, leaf, grow in GC, 20 days@25 C. (12 hour light/dark), shock 1 day at 40 C. | 3.241 | 0.329 |
| 24 | LH320, 20 days old, root, grow in GC, 20 days@25 C. (12 hour light/dark), shock 1 day at 40 C. | 1.118 | 0.239 |
| 25 | LH320, V18 plant, leaf, pool of V18 leaf tissue from 5 LH320 plants grown in GH | 3.950 | 0.021 |
| 26 | LH320, callus induction, callus, tissue from 1 g of callus growing on callus induction media | 1.352 | 0.035 |
| 27 | LH320, callus 6-BA, callus, tissue from 1 g of callus growing on 6-benzyladenine media | 1.383 | 0.085 |
| 28 | LH320, callus MSOD, callus, tissue from 1 g of callus growing on plant regeneration media | 1.944 | 0.108 |
| 29 | LH172, 5 days old, root, in dark, 4 days@25 C. | 1.831 | 0.166 |
| 30 | LH172, 5 days old, shoot, in dark, 4 days@25 C. | 4.920 | 0.087 |
| 31 | LH172, 5 days old, root, in dark, 4 days@25 C., shock for 24 hours@4 C. | 10.342 | 3.193 |
| 32 | LH172, 5 days old, shoot, in dark, 4 days@25 C., shock for 24 hours@4 C. | 25.394 | 1.644 |
| 33 | LH172, 21 days old, leaf, grow in GC, 21 days@25 C. | 2.107 | 0.075 |
| 34 | LH172, 21 days old, root, grow in GC, 21 days@25 C. | 0.042 | 0.001 |
| 35 | LH172, 21 days old, leaf, grow in GC, 21 days@25 C., shock for 21 hours@4 C. | 11.477 | 1.581 |
| 36 | LH172, 21 days old, root, grow in GC, 21 days@25 C., shock for 21 hours@4 C. | 0.008 | 0.001 |
| 37 | LH172, 21 days old, leaf, grow in GC, 21 days@25 C., shock for 21 hrs@4 C., return to 25 C. for 6 hrs | 0.371 | 0.091 |
| 38 | LH172, 21 days old, root, grow in GC, 21 days@25 C., shock for 21 hrs@4 C., return to 25 C. for 6 hrs | 0.009 | 0.001 |
| 39 | LH172, 21 days old, leaf, grow in GC, 21 days@25 C., shock for 21 hours@13 C. | 3.909 | 0.010 |
| 40 | LH172, 21 days old, root, grow in GC, 21 days@25 C., shock for 21 hours@13 C. | 0.005 | 0.000 |
| 41 | LH172, 21 days old, leaf, grow in GC, 21 days@25 C., shock for 21 hrs@13 C., return to 25 C. for 6 hrs | 0.923 | 0.111 |
| 42 | LH172, 21 days old, root, grow in GC, 21 days@25 C., shock for 21 hrs@13 C., return to 25 C. for 6 hrs | 0.004 | 0.000 |
| 43 | LH59, V7, leaf, V7 leaf collected 1 day after watering | 5.048 | 0.905 |

TABLE 3-continued

CVY-CIK1 Relative Expression in Cold Treated Samples

| Sample | Genotype, Age/stage, Tissue Type, Treatment | AVG Rel Exp | SD exp |
|---|---|---|---|
| 44 | LH59, V7, leaf, V7 leaf collected 8 days after watering (moderate drought) | 2.585 | 0.185 |
| 45 | LH244, 5 days old, root, in dark, 5 days@25 C. | 1.305 | 0.101 |
| 46 | LH244, 5 days old, shoot, in dark, 5 days@25 C. | 3.192 | 0.279 |
| 47 | LH244, 5 days old, root, in dark, 5 days@25 C., shock for 22 hours@10 C. | 4.803 | 0.726 |
| 48 | LH244, 5 days old, shoot, in dark, 5 days@25 C., shock for 22 hours@10 C. | 10.245 | 1.077 |
| 49 | Wigor, 5 days old, root, in dark, 5 days@25 C. | 0.878 | 0.025 |
| 50 | Wigor, 5 days old, shoot, in dark, 5 days@25 C. | 4.154 | 0.019 |
| 51 | Wigor, 5 days old, root, in dark, 5 days@25 C., shock for 22 hours@10 C. | 3.686 | 0.524 |
| 52 | Wigor, 5 days old, shoot, in dark, 5 days@25 C., shock for 22 hours@10 C. | 8.603 | 0.847 |
| 53 | LH195, 5 days old, root, in dark, 5 days@25 C. | 1.107 | 0.153 |
| 54 | LH195, 5 days old, shoot, in dark, 5 days@25 C. | 4.038 | 0.150 |
| 55 | LH195, 5 days old, root, in dark, 5 days@25 C., shock for 22 hours@10 C. | 2.713 | 0.084 |
| 56 | LH195, 5 days old, shoot, in dark, 5 days@25 C., shock for 22 hours@10 C. | 9.898 | 2.173 |
| 57 | LH320xHC33, 5 days old, root, in dark, 5 days@25 C. | 1.851 | 0.017 |
| 58 | LH320xHC33, 5 days old, shoot, in dark, 5 days@25 C. | 3.408 | 0.184 |
| 59 | LH320xHC33, 5 days old, root, in dark, 5 days@25 C., shock for 22 hours@10 C. | 6.932 | 0.484 |
| 60 | LH320xHC33, 5 days old, shoot, in dark, 5 days@25 C., shock for 22 hours@10 C. | 7.712 | 0.070 |
| 61 | LH320xLH244, 5 days old, root, in dark, 5 days@25 C. | 1.326 | 0.206 |
| 62 | LH320xLH244, 5 days old, shoot, in dark, 5 days@25 C. | 4.033 | 0.530 |
| 63 | LH320xLH244, 5 days old, root, in dark, 5 days@25 C., shock for 22 hours@10 C. | 3.981 | 0.535 |
| 64 | LH320xLH244, 5 days old, shoot, in dark, 5 days@25 C., shock for 22 hours@10 C. | 14.105 | 2.802 |
| 65 | LH320, 4 days old, root, in dark, 4 days@25 C. | 3.037 | 0.034 |
| 66 | LH320, 4 days old, shoot, in dark, 4 days@25 C. | 4.475 | 1.413 |
| 67 | LH320, 7 days old, root, in dark, 3 days@25 C., shock for 4 days@13 C. | 3.860 | 0.598 |
| 68 | LH320, 7 days old, shoot, in dark, 3 days@25 C., shock for 4 days@13 C. | 4.087 | 0.005 |
| 69 | LH320, 10 days old, root, in dark, 3 days@25 C., shock for 7 days@13 C. | 2.273 | 0.087 |
| 70 | LH320, 10 days old, shoot, in dark, 3 days@25 C., shock for 7 days@13 C. | 3.209 | 1.261 |

Samples 34, 36, 38, 40, and 42 above (LH172 root tissue) appear to indicate little to no expression in this data set. Subsequent experiments using the same RNA preps with probes for different genes of interest produced similar results with these samples, suggesting contaminated or degraded RNA in these preps. Other experiments (using separate RNA preps) have shown that CVY-CIK1 is indeed inducible by cold temperatures in three week old root tissue.

These results indicate that the endogenous CVY-CIK1 promoter generally shows a significant response to cold temperatures in a variety of tissue types, while displaying only moderate levels of background expression in non-cold treated plants. Expression during tissue culture ("callus" tissues) was also relatively low, suggesting that this promoter does not express highly during this stage. This may be helpful when attempting to produce transgenic plants using transgenes that may be potentially lethal during transformation/tissue culture. In addition, the endogenous CVY-CIK1 promoter also appears to express in a similarly cold-responsive fashion in both inbred and hybrid tissues of a variety of different corn genotypes.

Example 12

Evaluation of pCVY-CIK1::iCVY-CIK1::GUS Hybrid Events in Field Conditions

In order to examine how the cloned CVY-CIK1 promoter (with endogenous intron) performs under field conditions, hybrid seed was made for field experiments. Inbred pMON42360 transgenics (in a LH320 background) were crossed to LH244 tester plants, using the transgenic plants as the male. The resulting hybrid seed was used in a field experiment in Jerseyville, Ill. in the summer of 2003 to examine expression of the cloned promoter under ordinary field conditions. The seeds were planted in a non-irrigated plot on May 30, 2003. Two selections of LH244/ZM_S57073 and LH244/ZM_S56638, along with one selection of LH244/ZM_S57075 were tested, along with a non-transgenic LH244/LH320 control. Samples from 3-5 plants/selection were collected at a number of different developmental stages (approximately V3, V8, VT/R1, R2, and R5)(developmental stages as defined in "How a Corn Plant Develops", Special Report #48, [1997], Iowa State University).

The following tissues were sampled at each stage:

TABLE 4

| V3 Tissues | V8 Tissues | VT/R1 Tissues | R2 Tissues | R5 Tissues |
|---|---|---|---|---|
| V2 leaf Internode below V2 leaf | V6 leaf Internode below V6 leaf | ear leaf internode below ear leaf unfertilized ear (cob) Tassel pollen/anther Silk | ear leaf internode below ear leaf 14 day after pollination seed | 35 day after pollination seed |

Sampling Dates:

V3 samples: Jun. 23, 2003

V8 samples: Jul. 14, 2003

VT/R1 samples (also approximate pollination date): Jul. 31, 2003

R2 samples: Aug. 11, 2003

R5 samples: Sep. 3, 2003

The samples were frozen directly into dry ice upon harvest, and stored at −80 C until RNA Taqman analysis. The V3 and V8 samples were collected in the mornings the day of collection, while the other samples were collected later in the day.

Weather data was downloaded from the NOAA website (National Oceanic and Atmospheric Administration—a U.S. government agency) from the Jerseyville 2SW weather station (station index #11-4489-6). Weather data from the days directly preceding the tissue harvest dates is included in Table 5A.

Table 5A probe set for the HSP17 terminator (along with a primer/probe set for 18S mRNA as a control). The results are summarized below. In general, the lab grown events for both LH244/ZM_S57075 and LH244/ZM_S56638 both showed cold induction of the CVY-CIK1:GUS cassette in root and shoot tissues above the expression measured in the warm control tissues. For the field grown samples, the younger tissues (V3 and V8 stages) appeared to show relatively higher expression of CVY-CIK1::GUS than was measured in the

TABLE 5A

| Year | Month | Day | Max Temp (F.) | Min Temp (F.) | Temp at 8 am (F.) | Precip (in) | Comments |
|---|---|---|---|---|---|---|---|
| June weather 7 days before collection of V3 tissue | | | | | | | |
| 2003 | 6 | 17 | 84 | 61 | 67 | 0 | |
| 2003 | 6 | 18 | 88 | 63 | 65 | 0 | |
| 2003 | 6 | 19 | 86 | 65 | 69 | 0 | |
| 2003 | 6 | 20 | 79 | 49 | 54 | 0.06 | |
| 2003 | 6 | 21 | 79 | 52 | 58 | 0 | |
| 2003 | 6 | 22 | 80 | 56 | 62 | 0 | |
| 2003 | 6 | 23 | 84 | 62 | 66 | 0 | Harvest V3 samples |
| July weather 7 days before collection of V8 samples | | | | | | | |
| 2003 | 7 | 9 | 91 | 70 | 72 | 0 | |
| 2003 | 7 | 10 | 91 | 64 | 67 | 1.4 | |
| 2003 | 7 | 11 | 84 | 64 | 67 | 0 | |
| 2003 | 7 | 12 | 84 | 63 | 66 | 0 | |
| 2003 | 7 | 13 | 83 | 58 | 61 | 0 | |
| 2003 | 7 | 14 | 83 | 57 | 65 | 0 | Harvest V8 samples |
| July weather 7 days before collection of Vt/R1 samples | | | | | | | |
| 2003 | 7 | 26 | 84 | 61 | 67 | 0 | |
| 2003 | 7 | 27 | 89 | 67 | 73 | 0 | |
| 2003 | 7 | 28 | 93 | 69 | 71 | 0.31 | |
| 2003 | 7 | 29 | 79 | 62 | 67 | 0.08 | |
| 2003 | 7 | 30 | 81 | 56 | 59 | 0 | |
| 2003 | 7 | 31 | 85 | 60 | 63 | 0 | Harvest VT/R1 samples |
| August weather 10 days before collection of R2 samples | | | | | | | |
| 2003 | 8 | 3 | 86 | 56 | 63 | 1.56 | Damaging hailstorm overnight |
| 2003 | 8 | 4 | 85 | 61 | 66 | 0 | |
| 2003 | 8 | 5 | 84 | 60 | 64 | 0 | |
| 2003 | 8 | 6 | 84 | 63 | 68 | 0.15 | |
| 2003 | 8 | 7 | 83 | 64 | 68 | 0 | |
| 2003 | 8 | 8 | 86 | 64 | 66 | 0 | |
| 2003 | 8 | 9 | 83 | 63 | 64 | 0 | |
| 2003 | 8 | 10 | 82 | 59 | 61 | 0 | |
| 2003 | 8 | 11 | 85 | 56 | 63 | 0 | Harvest R2 samples |
| Weather 7 days before collection of R5 samples | | | | | | | |
| 2003 | 8 | 29 | 93 | 71 | 75 | 0 | |
| 2003 | 8 | 30 | 79 | 68 | 68 | 0 | |
| 2003 | 8 | 31 | 85 | 64 | 65 | 0.16 | |
| 2003 | 9 | 1 | 80 | 65 | 67 | 1.62 | |
| 2003 | 9 | 2 | 72 | 62 | 64 | 0.62 | |
| 2003 | 9 | 3 | 75 | 57 | 59 | 0 | Harvest R5 samples |

To compare expression levels in the field with observed cold enhanced expression of CVY-CIK1-GUS in the lab, hybrid seed for two events (LH244/ZM_S57075 and LH244/ZM_S56638) were germinated in the lab in rolled germination paper in the dark for 4 days at 27 C (seed for LH244/ZM_S57073 was not available for this cold shock assay). On the fourth day, half of the seedlings were harvested in liquid nitrogen (roots and shoots separately) and the other half were transferred to a 10 C shock for approximately 20 hours before harvesting.

For analysis, both the field samples and the cold and warm treated lab grown tissues were ground into a fine powder under liquid nitrogen. These samples were then used for RNA taqman analysis (with three replicates each) using a primer/ older tissues (VT/R1, R2, and R5). Since the tissues for the V3 and V8 stages were harvested in the morning (around 9-10 am) while the VT/R1, R2, and R5 samples were harvested later in the day (1-3 pm), this relatively higher level of expression in the V3 and V8 tissues may be due to the cooler morning temperatures, possibly leading to higher expression of the cloned CVY-CIK1 promoter than in the warmer afternoon samples for the VT/R1, R2, and R5 samples. The morning temperatures listed above would be closer to the daily lows during harvest of the V3 and V8 samples, and the afternoon sampling of the VT/R1, R2, and R5 samples would be closer to the daily high temperatures. Alternatively, this promoter may just express a little more strongly in relatively younger plants than in older ones. Overall expression in later stage tissues appears to be relatively low. The weather data listed above suggests that these plants did not encounter a significant drought stress during the growing season (weather data from NOAA). However, a damaging hailstorm was recorded on Aug. 3, 2003.

The tissues used for RNA extraction (approximately 100 mg fresh weight each) were placed in 96 well format boxes (1.1 ml micro tubes, VWR, Cat# 20901-027) with one 5/32 inch bead (Abco cat #STN 302) in each well. To each sample, add 0.25 ml of a 1:1 solution of chilled nucleic acid purification lysis solution (ABI, Cat#. 4305895) and Phosphate Buffered Saline (Life Technologies, Cat # 12394-011). For any root or seedling samples, 6% N-laurorlsarcosine (Sigma Chemical) and 2% Polyvinylpyrrolidine (Sigma Chemical) was also added. The samples were tightly capped and homogenized by shaking at 1100 rpm twice for 120 seconds each. Centrifuge samples in a Jouan tabletop centrifuge at 2000 RPM for 2 minutes.

To isolate RNA from the above lysis mixture, 50 ul of each lysed sample was transferred to a stack of filter plates before spinning. A GFC plate (Whatman #7700-01101) was stacked on top of a GFF plate (Whatman #7700-2110), which was stacked onto a collection plate (Whatman #7701-1100). After applying 50 ul of the extract to the top (GFC) plate in this stack, the plates were spun at 200 rpm in a Jouan tabletop centrifuge for 2 minutes. The GFC plate was discarded, the RNA was captured in the GFF filter, and the DNA was captured in the collection plate. To wash and elute the RNA, 60 ul of ABI RNA wash buffer 1 (ABI #4305891) was added to the GFF plate, and the plates were spun in a tabletop centrifuge at 2000 RPM for 2 minutes. The eluate was discarded. 60 ul of ABI RNA wash 2 (ABI cat #4305890) was added to each well, the plates were spun, and the eluate discarded. The step with wash buffer 2 was then repeated. To elute, 50 ul of RNA elution buffer (ABI # 4305893) was added to each well and spun.

A similar experiment was conducted in greenhouse conditions using inbred pCVY-CIK1::iCVY-CIK1::GUS transgenic plant material. In this experiment, inbred plants from a number of transgenic events were grown to maturity under standard greenhouse conditions, and tissues were sampled at the VT/R1 stage, R2, and R5 stages. Expression in tissues from these growth stages was examined via RNA Taqman (using the HSP17 terminator primer/probe set as described above) for the following tissues: unfertilized ear/cob, leaf, internode, root, ~14DAP seed, ~35DAP seed, tassel, and pollen. RNA from these tissues was used in RNA Taqman experiments along with RNA from 4 day old cold shocked seedlings as a control. The results were similar to the field grown hybrid samples described above, in that expression of CVY-CIK1::GUS in mature, warm grown tissues was generally lower than the expression found in the cold treated samples.

Table 5B
Results for Field Grown Samples:

TABLE 5B

| Selection | Dev Stage | Tissue | Pedigree | Avg Exp. | Std Dev |
|---|---|---|---|---|---|
| Warm | VE- | Root, tip | LH244/(ZM_S57075) | 5685.4 | 737.2 |
| Cold | VE- | Root, tip | LH244/(ZM_S57075) | 9941.5 | 502.1 |
| Warm | VE- | shoot | LH244/(ZM_S57075) | 2105.4 | 48.4 |
| Cold | VE- | shoot | LH244/(ZM_S57075) | 7625.3 | 643.7 |
| 1 | V3- | V2 leaf | LH244/(ZM_S57075) | 2506.0 | 488.8 |
| 1 | V3- | internode | LH244/(ZM_S57075) | 4959.8 | 1456.9 |

TABLE 5B-continued

| Selection | Dev Stage | Tissue | Pedigree | Avg Exp. | Std Dev |
|---|---|---|---|---|---|
| 1 | V8- | V6 leaf | LH244/(ZM_S57075) | 1089.4 | 220.1 |
| 1 | V8- | internode | LH244/(ZM_S57075) | 1904.1 | 275.8 |
| 1 | VT- | anther | LH244/(ZM_S57075) | 113.4 | 28.1 |
| 1 | VT- | unfertilized ear/cob | LH244/(ZM_S57075) | 1009.5 | 233.2 |
| 1 | VT- | silk | LH244/(ZM_S57075) | 431.7 | 36.8 |
| 1 | VT- | ear leaf | LH244/(ZM_S57075) | 1002.1 | 153.2 |
| 1 | VT- | internode | LH244/(ZM_S57075) | 1003.1 | 35.2 |
| 1 | VT- | tassel | LH244/(ZM_S57075) | 536.7 | 46.0 |
| 1 | R2- | ear leaf | LH244/(ZM_S57075) | 1288.8 | 131.6 |
| 1 | R2- | seed, 14 DAP | LH244/(ZM_S57075) | 341.9 | 81.0 |
| 1 | R2- | internode | LH244/(ZM_S57075) | 714.1 | 43.4 |
| 1 | R5- | seed, 35 DAP | LH244/(ZM_S57075) | 624.4 | 152.1 |
| 1 | V3- | V2 leaf | LH244/(ZM_S57073) | 1638.9 | 157.0 |
| 2 | V3- | V2 leaf | LH244/(ZM_S57073) | 1819.6 | 196.6 |
| 1 | V3- | internode | LH244/(ZM_S57073) | 2193.2 | 246.8 |
| 2 | V3- | internode | LH244/(ZM_S57073) | 1591.4 | 148.2 |
| 1 | V8- | V6 leaf | LH244/(ZM_S57073) | 653.8 | 39.1 |
| 2 | V8- | V6 leaf | LH244/(ZM_S57073) | 763.1 | 172.1 |
| 1 | V8- | internode | LH244/(ZM_S57073) | 902.0 | 133.2 |
| 2 | V8- | internode | LH244/(ZM_S57073) | 765.0 | 101.5 |
| 1 | VT- | anther | LH244/(ZM_S57073) | 130.9 | 134.5 |
| 2 | VT- | anther | LH244/(ZM_S57073) | 19.8 | 6.7 |
| 1 | VT- | unfertilized ear/cob | LH244/(ZM_S57073) | 299.7 | 26.9 |
| 2 | VT- | unfertilized ear/cob | LH244/(ZM_S57073) | 205.3 | 21.1 |
| 1 | VT- | silk | LH244/(ZM_S57073) | 99.3 | 35.2 |
| 2 | VT- | silk | LH244/(ZM_S57073) | 116.8 | 2.9 |
| 1 | VT- | ear leaf | LH244/(ZM_S57073) | 375.2 | 96.4 |
| 2 | VT- | ear leaf | LH244/(ZM_S57073) | 207.5 | 52.7 |
| 1 | VT- | internode | LH244/(ZM_S57073) | 374.1 | 33.6 |
| 2 | VT- | internode | LH244/(ZM_S57073) | 231.6 | 36.6 |
| 1 | VT- | tassel | LH244/(ZM_S57073) | 123.7 | 22.6 |
| 2 | VT- | tassel | LH244/(ZM_S57073) | 93.8 | 9.7 |
| 1 | R2- | ear leaf | LH244/(ZM_S57073) | 645.8 | 118.3 |
| 2 | R2- | ear leaf | LH244/(ZM_S57073) | 593.3 | 62.4 |
| 1 | R2- | seed, 14 DAP | LH244/(ZM_S57073) | 136.6 | 30.5 |
| 2 | R2- | seed, 14 DAP | LH244/(ZM_S57073) | 137.3 | 28.3 |
| 1 | R2- | internode | LH244/(ZM_S57073) | 305.2 | 9.5 |
| 2 | R2- | internode | LH244/(ZM_S57073) | 315.3 | 46.4 |
| 1 | R5- | seed, 35 DAP | LH244/(ZM_S57073) | 106.1 | 66.1 |
| 2 | R5- | seed, 35 DAP | LH244/(ZM_S57073) | 64.3 | 29.1 |
| warm | VE- | Root, tip | LH244/(ZM_S56638) | 648.7 | 40.2 |
| cold | VE- | Root, tip | LH244/(ZM_S56638) | 1236.4 | 118.1 |
| warm | VE- | shoot | LH244/(ZM_S56638) | 468.0 | 121.6 |
| cold | VE- | shoot | LH244/(ZM_S56638) | 998.4 | 51.7 |
| 1 | V3- | V2 leaf | LH244/(ZM_S56638) | 725.3 | 178.0 |
| 2 | V3- | V2 leaf | LH244/(ZM_S56638) | 3417.6 | 281.2 |
| 1 | V3- | internode | LH244/(ZM_S56638) | 1123.4 | 51.8 |
| 2 | V3 | internode | LH244/(ZM_S56638) | 3182.3 | 360.2 |
| 1 | V8- | V6 leaf | LH244/(ZM_S56638) | 682.8 | 181.1 |
| 2 | V8- | V6 leaf | LH244/(ZM_S56638) | 2079.5 | 314.4 |
| 1 | V8- | internode | LH244/(ZM_S56638) | 456.1 | 60.7 |
| 2 | V8- | internode | LH244/(ZM_S56638) | 2067.0 | 154.5 |
| 1 | VT- | anther | LH244/(ZM_S56638) | 84.2 | 43.5 |
| 2 | VT- | anther | LH244/(ZM_S56638) | 63.6 | 6.4 |
| 1 | VT- | unfertilized ear/cob | LH244/(ZM_S56638) | 334.8 | 81.4 |
| 2 | VT- | unfertilized ear/cob | LH244/(ZM_S56638) | 485.9 | 174.5 |
| 1 | VT- | silk | LH244/(ZM_S56638) | 252.1 | 12.4 |
| 2 | VT- | silk | LH244/(ZM_S56638) | 412.0 | 53.8 |
| 1 | VT- | ear leaf | LH244/(ZM_S56638) | 294.7 | 20.6 |
| 2 | VT- | ear leaf | LH244/(ZM_S56638) | 327.6 | 39.5 |

TABLE 5B-continued

| Selection | Dev Stage | Tissue | Pedigree | Avg Exp. | Std Dev |
|---|---|---|---|---|---|
| 1 | VT- | internode | LH244/(ZM_S56638) | 455.1 | 82.7 |
| 2 | VT- | internode | LH244/(ZM_S56638) | 490.0 | 128.6 |
| 1 | VT- | tassel | LH244/(ZM_S56638) | 110.5 | 26.7 |
| 2 | VT- | tassel | LH244/(ZM_S56638) | 275.2 | 33.4 |
| 1 | R2- | ear leaf | LH244/(ZM_S56638) | 325.1 | 46.7 |
| 2 | R2- | ear leaf | LH244/(ZM_S56638) | 1378.4 | 172.2 |
| 1 | R2- | seed, 14 DAP | LH244/(ZM_S56638) | 109.5 | 30.1 |
| 2 | R2- | seed, 14 DAP | LH244/(ZM_S56638) | 425.0 | 167.8 |
| 1 | R2- | internode | LH244/(ZM_S56638) | 198.5 | 75.4 |
| 2 | R2- | internode | LH244/(ZM_S56638) | 689.6 | 193.5 |
| 1 | R5- | seed, 35 DAP | LH244/(ZM_S56638) | 50.1 | 17.8 |
| 2 | R5- | seed, 35 DAP | LH244/(ZM_S56638) | 555.3 | 259.6 |
| 1 | V3 | V2 leaf | LH244/LH320 | 25.6 | 3.8 |
| 1 | V3 | internode | LH244/LH320 | 7.4 | 2.7 |
| 1 | V8 | V6 leaf | LH244/LH320 | 25.8 | 11.8 |
| 1 | V8 | internode | LH244/LH320 | 22.2 | 13.2 |
| 1 | VT | anther | LH244/LH320 | 3.3 | 2.5 |
| 1 | VT | unfertilized ear/cob | LH244/LH320 | 8.4 | 5.3 |
| 1 | VT | silk | LH244/LH320 | 3.7 | 2.2 |
| 1 | VT | ear leaf | LH244/LH320 | 20.9 | 5.9 |
| 1 | VT | internode | LH244/LH320 | 61.7 | 44.0 |
| 1 | VT | tassel | LH244/LH320 | 4.3 | 3.2 |
| 1 | R2 | ear leaf | LH244/LH320 | 25.0 | 7.5 |

TABLE 5B-continued

| Selection | Dev Stage | Tissue | Pedigree | Avg Exp. | Std Dev |
|---|---|---|---|---|---|
| 1 | R2 | seed, 14 DAP | LH244/LH320 | 17.6 | 8.1 |
| 1 | R2 | internode | LH244/LH320 | 21.4 | 4.6 |
| 1 | R5 | seed, 35 DAP | LH244/LH320 | 7.2 | 1.1 |

Example 13

Expression of Cloned pCVY-CIK1::GUS in 4 Day Old and 10 Day Old Seedlings with and without Cold Shock The data in this example includes the data initially described in example 9. The data described here includes an additional replicate of the RNA Taqman analysis for these samples.

To examine the expression of the cloned CVY-CIK1 promoter, R1 transgenic seed transformed with pMON42360 (pCVY-CIK1 with endogenous intron driving expression of the GUS reporter gene) were germinated on rolled germination paper for three days at 28 C. On day three, half of the seedlings were transferred to 10 C for a cold treatment lasting approximately 20 hours, while the other half of the seedlings remained in the warm temperatures as a warm control. Since these seeds were still segregating for the transgene, GOI positive plants were identified via NPTII ELISA. The tissue from the positive plants were pooled and ground into a fine powder under liquid nitrogen. Expression of the transgenic promoter was measured via RNA Taqman using the primer/probe set for the HSP17 terminator, which was used in the pCVY-CIK1::GUS::hsp17 terminator transgenic cassette. Seeds from six separate transgenic LH320-based corn events were examined (the events were named ZM_S56638, ZM_S57073, ZM_S57075, ZM_S57228, ZM_S57234, and ZM_S57341). Each sample was tested in triplicate, although a few reactions failed, leaving only two reps for some datapoints. The expression results are expressed as an average of the replicates. The values indicate relative expression as compared to a non-transformed control. T-test values were calculated in Microsoft Excel using two-tailed analysis.

TABLE 6

Taqman values in 4 day old seedlings

| Shoot warm | Shoot cold | Fold Change Shoot cold/warm | T-test shoot cold/warm | Root warm | Root cold | Fold Change Root cold/warm | T-test root cold/warm |
|---|---|---|---|---|---|---|---|
| 183.1 | 3773.9 | 20.6 | 0.2813 | 44.7 | 301.3 | 6.7 | 0.0003 |
| 346.8 | 607.4 | 1.8 | 0.0820 | 345.6 | 467.1 | 1.4 | 0.7123 |
| 527.5 | 3378.2 | 6.4 | 0.0260 | 244.6 | 2754.4 | 11.3 | 0.0004 |
| 640.6 | 3773.9 | 5.9 | 0.0905 | 362.3 | 1941.9 | 5.4 | 0.0680 |
| 382.3 | 1296.0 | 3.4 | 0.0928 | 359.8 | 892.8 | 2.5 | 0.1530 |
| 190.8 | 1490.0 | 7.8 | 0.3385 | 98.7 | 179.2 | 1.8 | 0.0802 |

In order to determine the level of cold responsiveness of this promoter in older tissues, cold shock experiments were completed on greenhouse grown plants with three replicate of the data (except for event ZM_S57341, which only contains data from two replicates). Several plants per event were grown for 9 days in the greenhouse. After day nine, half of them were transferred to a dark Percival chamber set at 10 degrees C. These plants were also watered with pre-chilled water to rapidly drop the temperature of the soil. The other half of the plants were transferred to a dark Percival set at 25 degrees C. Both of these treatments were for approximately 21 hours. Leaf and root samples were collected after the treatments and submitted for RNA Taqman analysis. The results are included below in Table 6. In short, three of the four events showed a significant (P<0.1) increase in CIK1 promoter activity in the leaf in response to cold shock, while only one of the events showed a significant (P<0.1) cold response in the root tissue. In leaves, the fold change in expression in response to cold ranged from 0.4× to 15.5×, while in the root, the values ranged from 0.3 to 2.2 fold changes in response to exposure to cold temperatures. For the instances where the expression appears to have declined in the cold treated samples, the data is not significantly different by T-test.

The values indicate relative expression as compared to a non-transformed control. T-test values were calculated in Microsoft Excel using two-tailed analysis. Primers are shown in Table 8 and experimental results in Table 7.

In order to evaluate the expression of the CVY-CIK1 promoter under long term cold treatment, non-transformed LH320 seeds were grown in rolled, wet germination paper in the dark for 3 days at 27 C. After this initial 3 days in warm temperatures, the rolls were then transferred to 10 C in the dark for 1-10 days, with seedlings from one roll (20 kernels per roll) harvested each day for 10 days. Root and shoot tissue was harvested separately each day in liquid nitrogen. Each tissue set was ground to a fine powder under liquid nitrogen and used for RNA Taqman analysis to determine the expression levels of the endogenous CVY-CIK1 gene. Warm control plants were grown for 4 and 5 days at 27 C before being harvested in liquid nitrogen. Expression was measured via RNA taqman using the primer/probe set for the endogenous

TABLE 7

RNA Taqman values in ten day old seedlings

| Event | Leaf warm | leaf cold | fold change leaf cold/warm | T-test leaf cold/warm | root warm | root cold | fold change root cold/warm | T-test root cold/warm |
|---|---|---|---|---|---|---|---|---|
| ZM__S56638 | 105.1 | 497.5 | 4.7 | 0.009 | 1058.8 | 300.6 | 0.3 | 0.391 |
| ZM__S57075 | 683.1 | 3228.7 | 4.7 | 0.005 | 1594.9 | 914.7 | 0.6 | 0.458 |
| ZM__S57341 | 2682.8 | 1197.3 | 0.4 | 0.699 | 455.3 | 350.6 | 0.8 | 0.282 |
| ZM__S58344 | 555.7 | 8620.4 | 15.5 | 0.077 | 775.6 | 1721.9 | 2.2 | 0.001 |

| Standard Deviations Event | Leaf warm | leaf cold | root warm | root cold |
|---|---|---|---|---|
| ZM__S56638 | 85.3 | 72.9 | 1115.2 | 182.0 |
| ZM__S57075 | 274.2 | 478.7 | 953.6 | 544.8 |
| ZM__S57341 | 2301.6 | 597.5 | 4.1 | 45.5 |
| ZM__S58344 | 269.3 | 3464.7 | 397.7 | 424.2 |

Example 14

Expression of Endogenous CVY-CIK1 During Extended Cold Treatments Taqman Primers and Probes The probes for CVY-CIK1 were each labeled with the FAM reporter at the 5' end, and the TAMRA quencher at the 3' end. The 18S rRNA probe was used as a control in each reaction, and was labeled with the VIC reporter at the 5' end and the TAMRA quencher at the 3' end.

TABLE 8

| Gene ID | Oligo Function | Oligo ID and Position | Oligo Sequence |
|---|---|---|---|
| CVY-CIK1 | Forward primer | CVY-CIK1-825F | TATCTGGTCTTGCGGAGTAATCC (SEQ ID NO: 19) |
| | Reverse primer | CVY-CIK1-907R | TGTATAGGGCGATGATGTTGTCA (SEQ ID NO: 20) |
| | TaqMan probe | CVY-CIK1-850T | TTTGTTCTTCTTGCTGGATATTTA CCTTTCGAGG (SEQ ID NO: 21) |
| HSP-17 terminator | Forward primer | | AATTCTGCATGCGTTTGGAC (SEQ ID NO: 22) |
| | Reverse primer | | AAGAACTCGCACACACATCAA (SEQ ID NO: 23) |
| | TaqMan probe | | TATGCTCATTCAGGTTGGAGCCA ATTT (SEQ ID NO: 24) |
| 18S rRNA | Forward primer | | CGTCCCTGCCCTTTGTACAC (SEQ ID NO: 25) |
| | Reverse primer | | CGAACACTTCACCGGATCATT (SEQ ID NO: 26) |
| | TaqMan probe | | CCGCCCGTCGCTCCTACCGAT (SEQ ID NO: 27) |

CVY-CIK1 gene. As a control, a primer/probe set for 18S mRNA was also used for each sample to normalize from well to well.

Most of the results below are an average value from three replicates per sample, although some are from only two reps. Data are shown in Table 9.

TABLE 9

| Growth conditions | Tissue Type | Average Relative Taqman value | Standard deviation |
| --- | --- | --- | --- |
| 4 d@27 C. | Root | 782.8 | 174.9 |
| 5 d@27 C. | Root | 396.3 | 48.0 |
| 3 d@27 C., 1 d@10 C. | Root | 3747.6 | 1952.5 |
| 3 d@27 C., 2 d@10 C. | Root | 2991.8 | 392.9 |
| 3 d@27 C., 3 d@10 C. | Root | 2925.9 | 914.1 |
| 3 d@27 C., 4 d@10 C. | Root | 2299.6 | 1042.0 |
| 3 d@27 C., 5 d@10 C. | Root | 3114.2 | 1349.5 |
| 3 d@27 C., 6 d@10 C. | Root | 1655.0 | 185.7 |
| 3 d@27 C., 7 d@10 C. | Root | 1597.0 | 447.4 |
| 3 d@27 C., 8 d@10 C. | Root | 1614.3 | 359.0 |
| 3 d@27 C., 9 d@10 C. | Root | 826.2 | 82.7 |
| 3 d@27 C., 10 d@10 C. | Root | 576.5 | 290.6 |
| 4 d@27 C. | Shoot | 757.5 | 274.8 |
| 5 d@27 C. | Shoot | 1002.2 | 272.7 |
| 3 d@27 C., 1 d@10 C. | Shoot | 1478.0 | 52.8 |
| 3 d@27 C., 2 d@10 C. | Shoot | 1695.8 | 514.7 |
| 3 d@27 C., 3 d@10 C. | Shoot | 1879.2 | 358.5 |
| 3 d@27 C., 4 d@10 C. | Shoot | 930.7 | 586.5 |
| 3 d@27 C., 5 d@10 C. | Shoot | 911.1 | 495.0 |
| 3 d@27 C., 6 d@10 C. | Shoot | 1327.0 | 76.8 |
| 3 d@27 C., 7 d@10 C. | Shoot | 1081.9 | 86.6 |
| 3 d@27 C., 8 d@10 C. | Shoot | 1056.9 | 192.2 |
| 3 d@27 C., 9 d@10 C. | Shoot | 2626.2 | 1869.8 |
| 3 d@27 C., 10 d@10 C. | Shoot | 1312.8 | 297.1 |

Example 15

Identification of Novel Conserved Sequences in the CVY-CIK1 Promoter

In an attempt to identify potential novel regulatory sites in the CVY-CIK1 promoter region that may be important for stress responsive regulation, the promoter sequence for the CVY-CIK1 promoter was compared with the promoter regions for several other known stress responsive genes from the literature. The genes used in this comparison were:

1. pCVY-CIK1 (with endogenous intron) (from maize)
2. cor15a (Genbank Accession #U01377) (*Arabidopsis*)
3. rd29a (D13044) (*Arabidopsis*)
4. mlip15 (D26563) (maize)
5. wcs120 (AF031235) (wheat)
6. blt4.9 (U63993) (barley)
7. blt101.1 (AJ310994) (barley)
8. bn115 (U14665) (*brassica*)

This analysis was performed using the MEME analysis software (Bailey, T. L., and Elkan, C., [1994]. Fitting a mixture model by expectation maximization to discover motifs in biopolymers. Proceedings of the Second International Conference on Intelligent Systems for Molecular Biology, 28-36, AAAI Press, Menlo Park, Calif.). The analysis was run using two different groups, once using all of the promoters listed above, and a second time using only the promoters from the monocots (maize, wheat, and barley). The results are listed below. Each result is listed with a name on the top of each grouping (for example, "A1.O25"). The sites for each identified motif are listed by which promoter they were identified in, the first base pair of the motif in the specified promoter (numbering from 5' to 3'), the p-value for the match, and the actual sequence of the motif found in each promoter. Within each result, the motifs are sorted by p-value. A consensus sequence for the motif is listed in the first line of each grouping.

The motifs listed below are from the comparison of all eight promoters listed above (the motif names which start with "A1" are from the comparison of all eight promoters) (Table 10).

TABLE 10

Results using all 8 promoters

| Sequence | Start | P-value | Site |
|---|---|---|---|
| A1.O25 consensus | | | GTCCATCTGACCAGCGC Seq ID NO: 28 |
| wcs120 | 825 | 1.86E-09 | GTCCATCTGACCAGCCC Seq ID NO: 29 |
| blt4.9 | 1333 | 5.58E-08 | GCCTGTTTGACCAGCGC Seq ID NO: 30 |
| mlip15 | 1439 | 5.58E-08 | GTCCGTCCGAGGAGCAC Seq ID NO: 31 |
| CVY-CIK1 | 1398 | 9.10E-08 | GCGCATCTGTACAGCGC Seq ID NO: 32 |
| blt101.1 | 729 | 2.40E-06 | GCTCATCGGACAAGAAC Seq ID NO: 33 |
| rd29a | 215 | 3.18E-06 | TTCCATTTGACTAGTGT Seq ID NO: 34 |
| cor15a | 742 | 4.16E-06 | TTCTTTCTGAAAACCAC Seq ID NO: 35 |
| bn115 | 555 | 2.22E-05 | TTGCACCCGGTGACCGT Seq ID NO: 36 |
| A1.Z25 consensus | | | AGCTGAGCGTGATCAGCAGCCGCCGCTC Seq ID NO: 37 |
| mlip15 | 1515 | 4.53E-16 | AGCTGAGCGTGCTCCGTATCCGCCGCTC Seq ID NO: 38 |

TABLE 10-continued Results using all 8 promoters

| Sequence | Start | P-value | Site | |
|---|---|---|---|---|
| CVY-CIK1 | 432 | 7.28E-16 | AGGTGGGTGTGATCAGCAGCCGCTTCTC | Seq ID NO: 39 |
| A1.T1 consensus | | | CCGCGGGCTCGGACGAGGACGGTGACATCCGCCGCCGAGC | SEQ ID NO: 40 |
| wcs120 | 220 | 2.06E-18 | CCGCGTCGTCGGACGGGCACGGTGAGATGCGGCGTCGGGC | Seq ID NO: 41 |
| wcs120 | 164 | 2.31E-16 | CCGCGGTGTCGGACGGGGACGGTGAGATGCGGTGTCGAAC | Seq ID NO: 42 |
| wcs120 | 950 | 2.28E-12 | CCGCGGCCGCCATGGCGGCCGGGAGCATGCGACGTCGGGC | Seq ID NO: 43 |
| CVY-CIK1 | 985 | 7.66E-12 | CCCCCAGCTCGGACGGAGCTCCTCGCAGCAGCCGCCGATC | Seq ID NO: 44 |
| CVY-CIK1 | 885 | 1.36E-10 | TAGCGCCACCCCACCACCCTCGTCTCTCCCCCGTCGAGC | Seq ID NO: 45 |
| wcs120 | 97 | 1.48E-10 | CCGTGGCGGGGGACGACAACGCGGTCAGTCGCGGCAGAGG | Seq ID NO: 46 |
| blt101.1 | 1222 | 1.74E-10 | CCGCGTGCAGGCCCGGGGACACGTACACCACCTCCACATC | SEQ ID NO: 47 |
| mlip15 | 796 | 1.89E-10 | TAACGAGCTGGCTCGAGCTTCCTAACGAGCCGAGCCGAGC | Seq ID NO: 48 |
| mlip15 | 871 | 6.07E-10 | GAGCTGGCTCGTTATAGTAACGAGTCATAACGAGCCGAGC | Seq ID NO: 49 |
| CVY-CIK1 | 1043 | 1.02E-09 | GCGCTGGAAGGTGAGAGCTCAGTGCCTCGTCCCGCCCGCC | Seq ID NO: 50 |
| mlip15 | 1519 | 1.35E-09 | GAGCGTGCTCCGTATCCGCCGCTCCCACTCCTTCTCCGTC | Seq ID NO: 51 |
| blt4.9 | 1249 | 1.67E-09 | GCGCGCTATCGTCATCGCCCCTCCATCGCCGGAGTCGGGC | Seq ID NO: 52 |
| CVY-CIK1 | 417 | 6.67E-09 | CCGTCGTCAGTCACCAGGTGGGTGTGATCAGCAGCCGCTT | Seq ID NO: 53 |
| A1.Z6 consensus | | | GCCGGTCCCGTGGCCGTGGC | Seq Id NO: 54 |
| CVY-CIK1 | 823 | 4.55E-10 | GCGGGGTCCCTGTCCCTGGC | Seq ID NO: 55 |
| mlip15 | 1065 | 9.94E-13 | GGCGGTCCCGTGGCCGTGGC | Seq ID NO: 56 |
| wcs120 | 90 | 1.55E-10 | GCCGGATCCGTGGCGGGGGA | Seq ID NO: 57 |
| bn115 | 414 | 9.35E-10 | GCCGGTCCTGATGGCTTGGC | Seq ID NO: 58 |
| A1.T24 consensus | | | GCAGCACAGTCGTG | Seq ID NO: 59 |
| blt4.9 | 1302 | 1.53E-09 | GCAGCACAGTCGTG | Seq ID NO: 60 |
| CVY-CIK1 | 1387 | 4.05E-08 | GCAGTACAGACGCG | Seq ID NO: 61 |
| blt4.9 | 319 | 6.94E-08 | GCGGTACAGTCCTG | Seq ID NO: 62 |
| blt101.1 | 577 | 1.47E-07 | CCATCACAGCCGTG | Seq ID NO: 63 |
| A1.Z23 consensus | | | CCATCCACCCCTAGGGAACT | Seq ID NO: 64 |
| CVY-CIK1 | 744 | 1.42E-10 | CCATGCAGCCCTTGGGGCCT | Seq ID NO: 65 |
| wcs120 | 8 | 2.40E-10 | GCATCCACGCGTTGGGAGCT | Seq ID NO: 66 |
| blt4.9 | 1971 | 6.22E-10 | CCATACACCCCTACGGAACT | Seq ID NO: 67 |
| mlip15 | 1664 | 3.14E-09 | GAATCCATCTCTAGGGCTCT | Seq ID NO: 68 |
| A1.O5 consensus | | | GCTGGCCGACGTACACAAGCTT | Seq ID NO: 69 |
| blt4.9 | 549 | 4.15E-12 | GTTGGCCTACGTACACAAGCTT | Seq ID NO: 70 |
| cor15a | 538 | 2.94E-09 | GTTGGCCGACATACATTTGTTT | Seq ID NO: 71 |
| blt101.1 | 1234 | 1.59E-08 | CCGGGGACACGTACACCACCTC | Seq ID NO: 72 |
| bn115 | 977 | 3.03E-08 | GTTGGCCGACGTATACTTTTGT | Seq ID NO: 73 |

TABLE 10-continued

Results using all 8 promoters

| Sequence | Start | P-value | Site | |
|---|---|---|---|---|
| CVY-CIK1 | 38 | 5.48E-08 | GTTGGCGCACGTAATAATCCTT | Seq ID NO: 74 |
| mlip15 | 1176 | 6.43E-08 | CCCGGGAGACGTTCGAAACCTT | Seq ID NO: 75 |
| wcs120 | 392 | 1.02E-07 | GCGGGTATACGTACGTCGGCCT | Seq ID NO: 76 |
| rd29a | 649 | 1.43E-06 | TCAAGCCGACACAGACACGCGT | Seq ID NO: 77 |
| A1.T14 consensus | | | GGCCATACACCCCTA | Seq ID NO: 78 |
| CVY-CIK1 | 742 | 3.26E-09 | GGCCATGCAGCCCTT | Seq ID NO: 79 |
| wcs120 | 750 | 4.24E-08 | GGCCCGGCCCCCCTA | Seq ID NO: 80 |
| blt4.9 | 1969 | 5.48E-08 | GCCCATACACCCCTA | Seq ID NO: 81 |
| wcs120 | 454 | 9.00E-08 | GGCCATTCTGCCCTT | Seq ID NO: 82 |
| blt4.9 | 1763 | 2.45E-07 | GCCCCGACACCGCTA | Seq ID NO: 83 |
| CVY-CIK1 | 337 | 2.87E-07 | GGTCCTCCTGCCCTT | Seq ID NO: 84 |
| A1.Z24 consensus | | | CTCGCTATTGTGACGGGTCAGATCGAGC | Seq ID NO: 85 |
| CVY-CIK1 | 8 | 2.93E-14 | CTCGCTCGGGTGTCGGGTCAGATCGATC | Seq ID NO: 86 |
| mlip15 | 878 | 3.40E-12 | CTCGTTATAGTAACGAGTCATAACGAGC | Seq ID NO: 87 |
| blt101.1 | 455 | 6.43E-12 | CTCCCCACTGTTTGGGATCAGTTCGCGC | Seq ID NO: 88 |
| blt4.9 | 825 | 2.01E-11 | ATAGTTTTTTTGAGGGGTCAATGCGACC | Seq ID NO: 89 |
| A1.T15 consensus | | | GGGTCAAAACGATCCATTTGGAAGAC | Seq ID NO: 90 |
| CVY-CIK1 | 22 | 3.41E-13 | GGGTCAGATCGATCCAGTTGGCGCAC | Seq ID NO: 91 |
| blt4.9 | 1386 | 3.98E-12 | GGATCAGAAGGATCCAATTCGAAGAC | Seq ID NO: 92 |
| blt4.9 | 839 | 4.85E-12 | GGGTCAATGCGACCAATTTGGAAGCC | Seq ID NO: 93 |
| CVY-CIK1 | 301 | 5.75E-11 | GGGTCCACCGGATTTATTGGCAGTAC | Seq ID NO: 94 |
| A1.T10 consensus | | | TTCGACCTGCATGC | Seq ID NO: 95 |
| wcs120 | 38 | 1.97E-08 | GTCGACCTGCAGGC | Seq ID NO: 96 |
| blt4.9 | 13 | 1.97E-08 | GTCGACCTGCAGGC | Seq ID NO: 97 |
| CVY-CIK1 | 499 | 4.35E-08 | TTCCACCTGCATGC | Seq ID NO: 98 |
| blt101.1 | 678 | 3.35E-07 | TGCCACATGCATGG | Seq ID NO: 99 |
| CVY-CIK1 | 1213 | 5.15E-07 | TCCGAGCTGCAAGG | Seq ID NO: 100 |
| blt101.1 | 649 | 8.14E-07 | TGCGACATGCATAG | Seq ID NO: 101 |
| mlip15 | 1317 | 8.57E-07 | TTCGATCTGCGAGC | Seq ID NO: 102 |
| A1.T13 consensus | | | GTCAGCAGGCACCAGCCCATC | Seq ID NO: 103 |
| wcs120 | 855 | 6.08E-11 | GTCGGCACTCACCTGCCCATC | Seq ID NO: 104 |
| wcs120 | 765 | 6.66E-11 | GTCAGCAGCCACCTGCCGACC | Seq ID NO: 105 |
| mlip15 | 977 | 6.66E-11 | GTCAGCGGGCCCCACCTCATC | Seq ID NO: 106 |
| CVY-CIK1 | 850 | 4.15E-10 | GCCCACAGGCCACAGCGCATC | Seq ID NO: 107 |

TABLE 10-continued

Results using all 8 promoters

| Sequence | Start | P-value | Site | |
|---|---|---|---|---|
| A1.T28 consensus | | | CATCAAAAGGAGTACACGTGAAATAAGGAGAACGACCCGAAACTCGG | Seq ID NO: 108 |
| bn115 | 1007 | 1.07E-18 | CAACAAAGGTGGTACACGTGAAGTAACGATAACGACCCACAACTCCG | Seq ID NO: 109 |
| cor15a | 756 | 1.30E-17 | CACAAATATGATTACACGTGGCCTGAAAAGAACGAACAGAAACTCGG | Seq ID NO: 110 |
| CVY-CIK1 | 171 | 1.42E-17 | GATCATTCTGAGCATTTGCAGAAAAAGGAGAACGTCCCGAAATCCTG | Seq ID NO: 111 |
| blt101.1 | 876 | 1.06E-16 | GATTAAAAGGGGTATCTGAGACTCAAGGAAGAAGTCCCTATGGGAGG | Seq ID NO: 112 |
| A1.T7 consensus | | | GAAAAGGTGAATTGACAGGACACTGCAGG | Seq ID NO: 113 |
| CVY-CIK1 | 708 | 5.69E-14 | GAGAAGGTGTATTCACAGTACAGTGCAGG | Seq ID NO: 114 |
| rd29a | 125 | 6.01E-13 | GAAAAGGTGAATTAAGAGGAGAGAGGAGG | Seq ID NO: 115 |
| mlip15 | 316 | 6.01E-13 | GAGGAGGACGAGTGGGAGGGCACTTCTGG | Seq ID NO: 116 |
| CVY-CIK1 | 370 | 1.96E-12 | GCAGACGTGCACAGACAGGGCACCACCGG | Seq ID NO: 117 |
| A1.T18 consensus | | | ACGAATTCAGGATCTGGTTGTATCGA | Seq ID NO: 118 |
| CVY-CIK1 | 1122 | 1.64E-13 | ACGAATTCTGCATCTGGTTCTTTCGA | Seq ID NO: 119 |
| blt4.9 | 261 | 1.64E-13 | AAGAATTCAGGATCTGGTTGCATTGA | Seq ID NO: 120 |
| blt4.9 | 201 | 3.11E-13 | ACGATTTGAGGATCTCGATGTGCCGA | Seq ID NO: 121 |
| A1.T11 consensus | | | TCTTGGAGCCGGTCCCTCTG | Seq ID NO: 122 |
| CVY-CIK1 | 1494 | 9.71E-12 | TCTTGGTGCCGCTGCCTCTG | Seq ID NO: 123 |
| mlip15 | 1367 | 4.64E-11 | TCTTGCAGCCGGCCCCTCTG | Seq ID NO: 124 |
| CVY-CIK1 | 815 | 8.13E-10 | TTTTGGTGGCGGGGTCCCTG | Seq ID NO: 125 |
| bn115 | 407 | 9.35E-10 | TCTTTGAGCCGGTCCTGATG | Seq ID NO: 126 |
| A1.T40 consensus | | | GTTGGAAGAGAATA | Seq ID NO: 127 |
| CVY-CIK1 | 2040 | 3.97E-09 | GTTGGAAGAGAATA | Seq ID NO: 128 |
| blt101.1 | 59 | 9.85E-09 | GTTTGAAGAGAATA | Seq ID NO: 129 |
| A1.T16 consensus | | | TCGGGCCGTTCACG | Seq ID NO: 130 |
| wcs120 | 205 | 1.26E-09 | TCGGGCCGTTCACG | Seq ID NO: 131 |
| wcs120 | 149 | 1.26E-09 | TCGGGCCGTTCACG | Seq ID NO: 132 |
| CVY-CIK1 | 243 | 2.40E-08 | TCAGTCCGTGCAGG | Seq ID NO: 133 |
| A1.Z34 consensus | | | GGAGACACACCGC | Seq ID NO: 134 |
| CVY-CIK1 | 152 | 4.54E-09 | GGCGACACACCGC | Seq ID NO: 135 |
| blt4.9 | 1471 | 2.54E-08 | GGAGACACACCTC | Seq ID NO: 136 |
| A1.Z12 consensus | | | GTTGGCCGACATACA | Seq ID NO: 137 |
| cor15a | 538 | 1.76E-09 | GTTGGCCGACATACA | Seq ID NO: 138 |
| blt4.9 | 549 | 1.76E-09 | GTTGGCCTACGTACA | Seq ID NO: 139 |
| bn115 | 977 | 5.99E-09 | GTTGGCCGACGTATA | Seq ID NO: 140 |

TABLE 10-continued

Results using all 8 promoters

| Sequence | Start | P-value | Site | |
|---|---|---|---|---|
| CVY-CIK1 | 122 | 3.87E-08 | GCTGTCCTACACACA | Seq ID NO: 141 |
| A1.Z37 consensus | | | GGTGGTTGGAGTGTG | Seq ID NO: 142 |
| blt4.9 | 380 | 5.88E-10 | GGTGGTTGGTGTGTG | Seq ID NO: 143 |
| CVY-CIK1 | 217 | 2.97E-09 | GGTGGTTGTATTGTG | Seq ID NO: 144 |
| A1.T40 consensus | | | GTTGGAAGAGAATA | Seq ID NO: 145 |
| CVY-CIK1 | 2040 | 3.97E-09 | GTTGGAAGAGAATA | Seq ID NO: 146 |
| blt101.1 | 59 | 9.85E-09 | GTTTGAAGAGAATA | Seq ID NO: 147 |

Additionally, the MEME analysis was performed using only the monocot promoters listed above. The motifs identified using only the monocot promoters have names that begin with "MC". These results are listed below (Table 11).

TABLE 11

Results using only monocot promoters

| Sequence | Start | P-value | Site | |
|---|---|---|---|---|
| MC.O11 | | | | |
| consensus | | | AGCAGCCACCGGCCAAC | Seq ID NO: 148 |
| wcs120 | 768 | 5.54E-10 | AGCAGCCACCTGCCGAC | Seq ID NO: 149 |
| mlip15 | 1169 | 2.51E-08 | AGCCGCCCCCGGGAGAC | Seq ID NO: 150 |
| blt101.1 | 744 | 7.81E-08 | ACACGCCACCAGCAAAC | Seq ID NO: 151 |
| CVY-CIK1 | 1011 | 8.32E-08 | AGCAGCCGCCGATCAAC | Seq ID NO: 152 |
| blt4.9 | 1607 | 2.63E-07 | AGAGCCCTCCTGCCAGC | Seq ID NO: 153 |
| MC.O21 | | | | |
| consensus | | | TGGCCATTCAGCCCT | Seq ID NO: 154 |
| CVY-CIK1 | 741 | 2.84E-09 | TGGCCATGCAGCCCT | Seq ID NO: 155 |
| wcs120 | 453 | 2.80E-08 | TGGCCATTCTGCCCT | Seq ID NO: 156 |
| blt101.1 | 275 | 3.66E-07 | TCACTATTCAGCGCT | Seq ID NO: 157 |
| mlip15 | 930 | 3.92E-07 | TCGATATCCACCCCT | Seq ID NO: 158 |
| blt4.9 | 1968 | 4.75E-07 | AGCCCATACACCCCT | Seq ID NO: 159 |
| MC.T19 | | | | |
| consensus | | | AGCGCGCACACCGTCG | Seq ID NO: 160 |
| wcs120 | 884 | 7.93E-10 | AGCGCGCACGTCGTGG | Seq ID NO: 161 |
| CVY-CIK1 | 407 | 1.46E-09 | AGGGCGCACACCGTCG | Seq ID NO: 162 |
| MC.O23 | | | | |
| consensus | | | ACCGAGGCGAGTCGAGGCAGC | Seq ID NO: 163 |
| blt4.9 | 1232 | 6.50E-10 | ACTGAAGCGAGTCGAGGGCGC | Seq ID NO: 164 |
| mlip15 | 819 | 9.36E-10 | AACGAGCCGAGCCGAGCCAGC | Seq ID NO: 165 |
| wcs120 | 114 | 3.18E-09 | AACGCGGTCAGTCGCGGCAGA | Seq ID NO: 166 |

TABLE 11-continued

Results using only monocot promoters

| Sequence | Start | P-value | Site | |
|---|---|---|---|---|
| CVY-CIK1 | 147 | 6.67E-09 | ACCGAGGCGACACACCGCAGC | Seq ID NO: 167 |
| blt101.1 | 1197 | 2.21E-07 | GCTACGTGGAGTGCAGGTGGC | Seq ID NO: 168 |

MC.T10

| Sequence | Start | P-value | Site | |
|---|---|---|---|---|
| consensus | | | CCCCGAGCTCCGACGAAGCTCATCG | Seq ID NO: 169 |
| CVY-CIK1 | 985 | 1.17E-12 | CCCCCAGCTCGGACGGAGCTCCTCG | Seq ID NO: 170 |
| mlip15 | 1499 | 2.36E-12 | CGCCGTGCTCCGATGAAGCTGAGCG | Seq ID NO: 171 |
| CVY-CIK1 | 1212 | 2.92E-12 | CTCCGAGCTGCAAGGCCGCTCGTCG | Seq ID NO: 172 |

MC.Z36

| Sequence | Start | P-value | Site | |
|---|---|---|---|---|
| consensus | | | GCCCCATGGGACTAGGG | Seq ID NO: 173 |
| CVY-CIK1 | 287 | 2.16E-10 | GCTCGCTGGGAGTAGGG | Seq ID NO: 174 |
| blt4.9 | 1643 | 1.81E-09 | GCCCCATGGTCCTAGGG | Seq ID NO: 175 |

MC.T13

| Sequence | Start | P-value | Site | |
|---|---|---|---|---|
| consensus | | | AGACGAAACCCTCCTCGCCGTCCAATCC | Seq ID NO: 176 |
| CVY-CIK1 | 72 | 7.38E-13 | AGTCGAACCCTCCTCCCCGTCCAATCC | Seq ID NO: 177 |
| CVY-CIK1 | 927 | 5.10E-11 | ACAACACACCCTCCTCGTCCTCCAATCC | Seq ID NO: 178 |
| wcs120 | 854 | 8.96E-10 | AGTCGGCACTCACCTGCCCATCCACTCA | Seq ID NO: 179 |
| mlip15 | 1094 | 1.33E-09 | AGAATATGCCGTCCCAGCCCACCATCCC | Seq ID NO: 180 |
| blt4.9 | 1603 | 1.80E-09 | AAACAGAGCCCTCCTGCCAGCCCTTGCC | Seq ID NO: 181 |
| mlip15 | 939 | 4.37E-09 | ACCCCTAGCTGTCACCGTCGCCCAGTCC | Seq ID NO: 182 |
| blt4.9 | 317 | 9.75E-09 | AGGCGGTACAGTCCTGGCCAATATGACC | Seq ID NO: 183 |

MC.T34

| Sequence | Start | P-value | Site | |
|---|---|---|---|---|
| consensus | | | AAAGGGCCGCGCGA | Seq ID NO: 184 |
| blt101.1 | 640 | 8.37E-09 | AAAGGGCCGTGCGA | Seq ID NO: 185 |
| CVY-CIK1 | 766 | 1.51E-08 | AAAGGGTCGCGTGA | Seq ID NO: 186 |

MC.T38

| Sequence | Start | P-value | Site | |
|---|---|---|---|---|
| consensus | | | TCTTGCAGCCGCCCCCTCTG | Seq ID NO: 187 |
| CVY-CIK1 | 1494 | 1.14E-11 | TCTTGGTGCCGCTGCCTCTG | Seq ID NO: 188 |
| mlip15 | 1367 | 1.64E-11 | TCTTGCAGCCGGCCCCTCTG | Seq ID NO: 189 |

MC.Z27

| Sequence | Start | P-value | Site | |
|---|---|---|---|---|
| consensus | | | GAAAGAATTCAGCATCTGGTT | Seq ID NO: 190 |
| CVY-CIK1 | 1120 | 2.11E-12 | GCACGAATTCTGCATCTGGTT | Seq ID NO: 191 |
| blt4.9 | 259 | 2.11E-12 | GAAAGAATTCAGGATCTGGTT | Seq ID NO: 192 |

MC.T28

| Sequence | Start | P-value | Site | |
|---|---|---|---|---|
| consensus | | | TTCCCGGACAAGGGG | Seq ID NO: 193 |
| wcs120 | 690 | 8.12E-09 | TTCCCGGACAAGGAG | Seq ID NO: 194 |

TABLE 11-continued

Results using only monocot promoters

| Sequence | Start | P-value | Site | | |
|---|---|---|---|---|---|
| CVY-CIK1 | 1155 | 1.32E-08 | TTCCCGGACCGTGGG | Seq ID NO: | 195 |
| wcs120 | 354 | 3.07E-08 | TTCCCGTACACGGGC | Seq ID NO: | 196 |
| MC.Z24 | | | | | |
| consensus | | | ATGGCCATACAGCCC | Seq ID NO: | 197 |
| CVY-CIK1 | 740 | 7.66E-10 | ATGGCCATGCAGCCC | Seq ID NO: | 198 |
| wcs120 | 452 | 1.17E-08 | ATGGCCATTCTGCCC | Seq ID NO: | 199 |
| blt4.9 | 1967 | 4.16E-08 | AAGCCCATACACCCC | Seq ID NO: | 200 |
| MC.Z4 | | | | | |
| consensus | | | TTCGACCTGCAGGC | Seq ID NO: | 201 |
| wcs120 | 38 | 9.60E-09 | GTCGACCTGCAGGC | Seq ID NO: | 202 |
| blt4.9 | 13 | 9.60E-09 | GTCGACCTGCAGGC | Seq ID NO: | 203 |
| CVY-CIK1 | 499 | 2.39E-08 | TTCCACCTGCATGC | Seq ID NO: | 204 |
| mlip15 | 1317 | 4.68E-07 | TTCGATCTGCGAGC | Seq ID NO: | 205 |
| blt101.1 | 678 | 7.44E-07 | TGCCACATGCATGG | Seq ID NO: | 206 |
| MC.Z25 | | | | | |
| consensus | | | AGCAGCACAGACGCG | Seq ID NO: | 207 |
| CVY-CIK1 | 1386 | 3.83E-09 | AGCAGTACAGACGCG | Seq ID NO: | 208 |
| blt4.9 | 1301 | 3.83E-09 | AGCAGCACAGTCGTG | Seq ID NO: | 209 |
| MC.O26 | | | | | |
| consensus | | | CCATTCTCGTCCCC | Seq ID NO: | 210 |
| mlip15 | 1007 | 2.13E-08 | CCATTCTCGTCCTC | Seq ID NO: | 211 |
| CVY-CIK1 | 935 | 7.40E-08 | CCCTCCTCGTCCTC | Seq ID NO: | 212 |
| blt101.1 | 834 | 7.99E-07 | CCCTTTTAGTCCCA | Seq ID NO: | 213 |
| wcs120 | 210 | 9.56E-07 | CCGTTCACGTCCGC | Seq ID NO: | 214 |
| blt4.9 | 595 | 1.24E-06 | CCATCTTAATCCCC | Seq ID NO: | 215 |

Example 16

Analysis of the pCVY-CIK1 (with Endogenous Intron) Sequence for Known Transcription Factor Binding Sites In an effort to more fully understand the regulation of expression of the CVY-CIK1 promoter, and which transcription factors may be important in controlling its regulation in response to cold and other environmental and developmental regulation cues, sequence analysis was performed to identify potential binding sites for known transcription factors in the CVY-CIK1 promoter region. This analysis was completed using the PATCH search program (version 1.9, part of the TRANSFAC database distributed by Biobase).

The program settings were:
1. Sites for plant factors
2. Minimum site length: 5 bp
3. Maximum number of mismatches: 1
4. Mismatch penalty: 100
5. lower score boundary: 87.5.

The analysis was run using the sequence for the CVY-CIK1 promoter sequence, including the endogenous 5'UTR intron and 5'UTR sequence, since these regions may contain important sequence elements as well. Listed below are the search results.

The TRANSFAC database describes the column headings.

The results of the query are included below (Table 12). The position numbering is based on the 5'-most base of the CVY-CIK1 promoter being designated as base #1. The "position" numbers listed below indicate the position of the 5'most base of the binding site in the CVY-CIK1 promoter. A number of the sites listed have been described in the literature as important for stress-regulated expression (for example, the CBF binding sites).

TABLE 12

| Identifier | Position | Mismatches | Score | Binding Factor | Sequence - Seq ID NO |
|---|---|---|---|---|---|
| RAPE$NAPA_01 | 506 (-) | 0 | 100 | ABI3, FUS3 | CATGCA |
| RAPE$NAPA_01 | 508 (+) | 0 | 100 | ABI3, FUS3 | CATGCA |
| RAPE$NAPA_01 | 602 (-) | 0 | 100 | ABI3, FUS3 | CATGCA |
| RAPE$NAPA_01 | 745 (+) | 0 | 100 | ABI3, FUS3 | CATGCA |
| MAIZE$ADH11F_01 | 159 (+) | 0 | 100 | ABI4 | CACCGC |
| AS$ABI4_38 | 1784 (+) | 1 | 88.89 | ABI4 | GGTGCTCTTT - 216 |
| AS$ABI4_03 | 1956 (-) | 1 | 88.89 | ABI4 | ACCGCCCCC - 217 |
| AS$ABI4_26 | 300 (-) | 1 | 88.89 | ABI4 | GGTGCACCCT - 218 |
| AS$ABI4_31 | 384 (-) | 1 | 88.89 | ABI4 | GGTGCCTTGT - 219 |
| AS$ABI4_23 | 384 (-) | 1 | 88.89 | ABI4 | GGTGCTCTGT - 220 |
| AS$ABI4_40 | 387 (-) | 1 | 88.89 | ABI4 | GGTGCTGCCC - 221 |
| AS$ABI4_39 | 387 (-) | 1 | 88.89 | ABI4 | GGTGCTGCCC - 222 |
| AS$ABI4_20 | 388 (+) | 1 | 87.5 | ABI4 | GGCGCCACC - 223 |
| MAIZE$ADH11F_01 | 875 (+) | 0 | 100 | ABI4 | CACCGC |
| AS$ABI4_49 | 885 (-) | 1 | 88.89 | ABI4 | GGTGGGGCTA - 224 |
| AS$ABI4_14 | 886 (+) | 1 | 88.89 | ABI4 | AGCGCCGCCC - 225 |
| AS$ABI4_11 | 886 (+) | 1 | 88.89 | ABI4 | ACCGCCACCC - 226 |
| AS$ABI4_20 | 886 (+) | 1 | 87.5 | ABI4 | GGCGCCACC |
| AS$ABI4_51 | 886 (+) | 1 | 88.89 | ABI4 | GGCGCCACCC - 227 |
| MESAT$PRP2_02 | 130 (-) | 0 | 100 | Alfin1 | GTGTGT |
| MESAT$PRP2_02 | 132 (-) | 0 | 100 | Alfin1 | GTGTGT |
| MESAT$PRP2_02 | 1322 (+) | 0 | 100 | Alfin1 | GTGTGT |
| MESAT$PRP2_02 | 134 (-) | 0 | 100 | Alfin1 | GTGTGT |
| MESAT$PRP2_02 | 156 (-) | 0 | 100 | Alfin1 | GTGTGT |
| MESAT$PRP2_02 | 1565 (+) | 0 | 100 | Alfin1 | GTGTGT |
| MESAT$PRP2_02 | 1814 (+) | 0 | 100 | Alfin1 | GTGTGT |
| AS$ALFIN1_01 | 282 (-) | 1 | 87.5 | Alfin1 | GAGCGGTGG |
| MESAT$PRP2_04 | 872 (-) | 1 | 87.5 | Alfin1 | GCGGTGCTG |
| AS$ALFIN1_01 | 874 (-) | 1 | 87.5 | Alfin1 | GAGCGGTGG |
| MESAT$PRP2_02 | 930 (-) | 0 | 100 | Alfin1 | GTGTGT |
| AT$COR78_01 | 144 (+) | 0 | 100 | ANT, CBF1, CBF2, CBF3 | CCGAC |
| AT$COR78_01 | 1822 (+) | 0 | 100 | ANT, CBF1, CBF2, CBF3 | CCGAC |
| AT$COR78_01 | 1829 (+) | 0 | 100 | ANT, CBF1, CBF2, CBF3 | CCGAC |
| AT$COR78_01 | 19 (-) | 0 | 100 | ANT, CBF1, CBF2, CBF3 | CCGAC |
| AT$COR78_01 | 2082 (-) | 0 | 100 | ANT, CBF1, CBF2, CBF3 | CCGAC |
| AT$COR15A_01 | 144 (+) | 0 | 100 | ANT, CBF1, CBF2, CBF3, TSI1 | CCGAC |
| AT$COR15A_01 | 1822 (+) | 0 | 100 | ANT, CBF1, CBF2, CBF3, TSI1 | CCGAC |
| AT$COR15A_01 | 1829 (+) | 0 | 100 | ANT, CBF1, CBF2, CBF3, TSI1 | CCGAC |
| AT$COR15A_01 | 19 (-) | 0 | 100 | ANT, CBF1, CBF2, CBF3, TSI1 | CCGAC |

TABLE 12-continued

| Identifier | Position | Mismatches | Score | Binding Factor | Sequence - Seq ID NO |
|---|---|---|---|---|---|
| AT$COR15A_01 | 2082 (−) | 0 | 100 | ANT, CBF1, CBF2, CBF3, TSI1 | CCGAC |
| PEA$IAA45_07 | 1568 (−) | 0 | 100 | ARF1 | GAGACA |
| PEA$IAA45_07 | 1717 (−) | 0 | 100 | ARF1 | GAGACA |
| AS$ARF1_03 | 902 (+) | 1 | 90 | ARF1 | CCTCGTGTCTC - 228 |
| AS$ARF1_05 | 1568 (+) | 0 | 100 | ARF1, ARF4, ARF5, ARF6, ARF7, ARF8 | TGTCTC |
| AS$ARF1_05 | 1717 (+) | 0 | 100 | ARF1, ARF4, ARF5, ARF6, ARF7, ARF8 | TGTCTC |
| AS$ARF1_01 | 1568 (−) | 0 | 100 | ARF1, ARF5 | GAGACA |
| AS$ARF1_01 | 1568 (+) | 0 | 100 | ARF1, ARF5 | TGTCTC |
| AS$ARF1_01 | 1717 (−) | 0 | 100 | ARF1, ARF5 | GAGACA |
| AS$ARF1_01 | 1717 (+) | 0 | 100 | ARF1, ARF5 | TGTCTC |
| AS$ARR_01 | 211 (−) | 0 | 100 | ARR1, ARR2 | AGGATT |
| AS$ARR_01 | 53 (−) | 0 | 100 | ARR1, ARR2 | AGGATT |
| CAMV$35SR_01 | 421 (−) | 0 | 100 | ASF-1, NAC1, OBF4, OBF5, SARP, TGA1, TGA10, TGA1a, TGA1b, TGA2, TGA2.1, TGA2.2, TGA3, TGA6, ZAP1 | TGACG |
| TDNA$NOS_01 | 1038 (−) | 0 | 100 | ASF-1, OBF3.1, TGA1a, TGA1b | TGAGC |
| TDNA$NOS_01 | 1059 (−) | 0 | 100 | ASF-1, OBF3.1, TGA1a, TGA1b | TGAGC |
| TDNA$NOS_01 | 179 (+) | 0 | 100 | ASF-1, OBF3.1, TGA1a, TGA1b | TGAGC |
| TDNA$NOS_01 | 237 (−) | 0 | 100 | ASF-1, OBF3.1, TGA1a, TGA1b | TGAGC |
| TDNA$NOS_01 | 421 (+) | 0 | 100 | ASF-1, OBF3.1, TGA1a, TGA1b | CGTCAG |
| ARHIZ$ROLB_01 | 1522 (+) | 0 | 100 | BBF1 | ACTTTA |
| MAIZE$BZ1_02 | 620 (−) | 0 | 100 | C1 (long form), MYB2 | TAACTG |
| PV$PHASL_02 | 431 (−) | 0 | 100 | CAN | CACCTG |
| PV$PHASL_02 | 502 (+) | 0 | 100 | CAN | CACCTG |
| AT$RD29B_01 | 144 (+) | 0 | 100 | CBF1 | CCGAC |
| AT$RD29B_01 | 1822 (+) | 0 | 100 | CBF1 | CCGAC |
| AT$RD29B_01 | 1829 (+) | 0 | 100 | CBF1 | CCGAC |
| AT$RD29B_01 | 19 (−) | 0 | 100 | CBF1 | CCGAC |
| AT$RD29B_01 | 2082 (−) | 0 | 100 | CBF1 | CCGAC |
| AT$COR15B_01 | 144 (+) | 0 | 100 | CBF1, CBF2, CBF3 | CCGAC |
| AT$COR15B_01 | 1822 (+) | 0 | 100 | CBF1, CBF2, CBF3 | CCGAC |
| AT$COR15B_01 | 1829 (+) | 0 | 100 | CBF1, CBF2, CBF3 | CCGAC |
| AT$COR15B_01 | 19 (−) | 0 | 100 | CBF1, CBF2, CBF3 | CCGAC |
| AT$COR15B_01 | 2082 (−) | 0 | 100 | CBF1, CBF2, CBF3 | CCGAC |
| AT$RD29A_01 | 144 (+) | 0 | 100 | CBF1, DREB1A, DREB2A | CCGAC |
| AT$RD29A_01 | 1822 (+) | 0 | 100 | CBF1, DREB1A, DREB2A | CCGAC |
| AT$RD29A_01 | 1829 (+) | 0 | 100 | CBF1, DREB1A, DREB2A | CCGAC |
| AT$RD29A_01 | 19 (−) | 0 | 100 | CBF1, DREB1A, DREB2A | CCGAC |
| AT$RD29A_01 | 2082 (−) | 0 | 100 | CBF1, DREB1A, DREB2A | CCGAC |

TABLE 12-continued

| Identifier | Position | Mismatches | Score | Binding Factor | Sequence - Seq ID NO |
|---|---|---|---|---|---|
| RAPE$BN115_01 | 144 (+) | 0 | 100 | CBF17, CBF5 | CCGAC |
| RAPE$BN115_02 | 144 (+) | 0 | 100 | CBF17, CBF5 | CCGAC |
| RAPE$BN115_01 | 1822 (+) | 0 | 100 | CBF17, CBF5 | CCGAC |
| RAPE$BN115_02 | 1822 (+) | 0 | 100 | CBF17, CBF5 | CCGAC |
| RAPE$BN115_02 | 1829 (+) | 0 | 100 | CBF17, CBF5 | CCGAC |
| RAPE$BN115_01 | 1829 (+) | 0 | 100 | CBF17, CBF5 | CCGAC |
| RAPE$BN115_01 | 19 (−) | 0 | 100 | CBF17, CBF5 | CCGAC |
| RAPE$BN115_02 | 19 (−) | 0 | 100 | CBF17, CBF5 | CCGAC |
| RAPE$BN115_02 | 2082 (−) | 0 | 100 | CBF17, CBF5 | CCGAC |
| RAPE$BN115_01 | 2082 (−) | 0 | 100 | CBF17, CBF5 | CCGAC |
| PEA$PRA2_01 | 2031 (−) | 0 | 100 | DF1 | TACACT |
| PEA$PRA2_01 | 726 (+) | 0 | 100 | DF1 | TACAGT |
| POT$KST1_01 | 1790 (−) | 0 | 100 | DOF1 | AAAAG |
| POT$KST1_01 | 1808 (+) | 0 | 100 | DOF1 | AAAAG |
| POT$KST1_01 | 1908 (−) | 0 | 100 | DOF1 | AAAAG |
| POT$KST1_01 | 193 (+) | 0 | 100 | DOF1 | AAAAG |
| POT$KST1_01 | 1937 (−) | 0 | 100 | DOF1 | AAAAG |
| POT$KST1_01 | 57 (−) | 0 | 100 | DOF1 | AAAAG |
| POT$KST1_01 | 765 (+) | 0 | 100 | DOF1 | AAAAG |
| POT$KST1_01 | 814 (−) | 0 | 100 | DOF1 | AAAAG |
| MAIZE$PEPC_03 | 1635 (+) | 1 | 88.89 | Dof2, MNB1a | TCACTTTTT |
| MAIZE$PEPC_04 | 1787 (−) | 1 | 88.89 | Dof2, MNB1a | AAAAAGGAGC - 229 |
| MAIZE$PEPC_04 | 192 (+) | 1 | 88.89 | Dof2, MNB1a | AAAAAGGAGC - 229 |
| MAIZE$PEPC_05 | 1933 (−) | 1 | 88.89 | Dof2, MNB1a | AAAAAGAAGC - 230 |
| MAIZE$PEPC_05 | 353 (−) | 1 | 88.89 | Dof2, MNB1a | AAAAAGAAGC - 230 |
| MAIZE$PEPC_02 | 578 (−) | 1 | 88.89 | Dof2, MNB1a | ATACTTTTC |
| DAUCE$DC3_02 | 14 (−) | 0 | 100 | DPBF-1, DPBF-2 | CACCCG |
| DAUCE$DC3_03 | 1461 (−) | 0 | 100 | DPBF-1, DPBF-2 | CACTTG |
| DAUCE$DC3_03 | 540 (−) | 0 | 100 | DPBF-1, DPBF-2 | CACTTG |
| DAUCE$DC3_04 | 773 (−) | 0 | 100 | DPBF-1, DPBF-2 | CACGCG |
| NT$PRB1B_01 | 1014 (−) | 0 | 100 | EBP | GGCGGCT |
| AS$mEMBP_04 | 1062 (−) | 0 | 100 | EmBP-1a | CACTG |
| AS$mEMBP_15 | 1563 (−) | 0 | 100 | EmBP-1a | CACGT |
| AS$mEMBP_04 | 167 (−) | 0 | 100 | EmBP-1a | CACTG |
| AS$mEMBP_04 | 2022 (+) | 0 | 100 | EmBP-1a | CACTG |
| AS$mEMBP_15 | 374 (−) | 0 | 100 | EmBP-1a | CACGT |
| AS$mEMBP_15 | 45 (+) | 0 | 100 | EmBP-1a | CACGT |
| AS$mEMBP_04 | 488 (−) | 0 | 100 | EmBP-1a | CACTG |
| AS$mEMBP_04 | 574 (−) | 0 | 100 | EmBP-1a | CACTG |

TABLE 12-continued

| Identifier | Position | Mismatches | Score | Binding Factor | Sequence - Seq ID NO |
|---|---|---|---|---|---|
| AS$mEMBP_15 | 599 (−) | 0 | 100 | EmBP-1a | CACGT |
| AS$mEMBP_04 | 728 (−) | 0 | 100 | EmBP-1a | CACTG |
| AS$GCCBOX_01 | 1015 (+) | 0 | 100 | ERF2, ERF3, ERF4 | GCCGCC |
| WHEAT$LMWG1D1_03 | 1994 (−) | 1 | 87.5 | ESBF I | TGTAAAAGT |
| AS$GAMYB_15 | 1348 (+) | 1 | 87.5 | GAMYB | TCAACGCCG |
| AS$GAMYB_11 | 142 (+) | 0 | 100 | GAMYB | AACCGAC |
| AS$GAMYB_08 | 142 (+) | 0 | 100 | GAMYB | AACCGAC |
| AS$GAMYB_08 | 1820 (+) | 0 | 100 | GAMYB | AACCGAC |
| AS$GAMYB_11 | 1820 (+) | 0 | 100 | GAMYB | AACCGAC |
| AS$GAMYB_02 | 217 (−) | 0 | 100 | GAMYB | AACCACC |
| BAR$GLB1_01 | 275 (+) | 0 | 100 | GAMYB | CAACAACC |
| CARO$TDC_08 | 1562 (+) | 0 | 100 | GBF1, GBF2 | AACGTG |
| MAIZE$ADH11S_06 | 1080 (+) | 0 | 100 | GCBP-1, Sp1 | GCCCC |
| MAIZE$ADH11S_06 | 1184 (−) | 0 | 100 | GCBP-1, Sp1 | GCCCC |
| MAIZE$ADH11S_06 | 757 (−) | 0 | 100 | GCBP-1, Sp1 | GCCCC |
| NT$PR1A_03 | 1245 (−) | 0 | 100 | GT-1 | GAAAAA |
| NT$PR1A_04 | 1711 (+) | 0 | 100 | GT-1 | ATTTAC |
| NT$PR1A_03 | 1794 (−) | 0 | 100 | GT-1 | GAAAAA |
| NT$PRIA_03 | 1903 (+) | 0 | 100 | GT-1 | TTTTCC |
| NT$PRIA_03 | 191 (+) | 0 | 100 | GT-1 | GAAAAA |
| NT$PRIA_03 | 1910 (−) | 0 | 100 | GT-1 | GAAAAA |
| NT$PRIA_03 | 578 (+) | 0 | 100 | GT-1 | GAAAAA |
| NT$PRIA_03 | 58 (+) | 0 | 100 | GT-1 | TTTTCC |
| AS$HAHB4_05 | 1432 (+) | 1 | 87.5 | HAHB-4 | TAATGATTG |
| AS$HAHB4_19 | 1432 (+) | 1 | 87.5 | HAHB-4 | TAATGATTG |
| AS$HAHB4_24 | 1432 (+) | 1 | 87.5 | HAHB-4 | TAATGATTG |
| AS$HAHB4_11 | 1432 (+) | 1 | 87.5 | HAHB-4 | TAATGATTG |
| AS$HAHB4_22 | 1432 (+) | 1 | 87.5 | HAHB-4 | TAATGATTG |
| AS$HAHB4_21 | 1432 (+) | 1 | 87.5 | HAHB-4 | TAATGATTG |
| AS$HAHB4_01 | 1606 (−) | 1 | 87.5 | HAHB-4 | TAATGATTC |
| AS$HAHB4_12 | 1647 (−) | 1 | 87.5 | HAHB-4 | AAATGATTG |
| AS$HAHB4_03 | 170 (−) | 1 | 87.5 | HAHB-4 | TAATGATCA |
| AS$HAHB4_17 | 1707 (−) | 1 | 87.5 | HAHB-4 | TAATTATTA |
| AS$HAHB4_15 | 1707 (+) | 1 | 87.5 | HAHB-4 | TAATAATTA |
| AS$HAHB4_06 | 588 (−) | 1 | 87.5 | HAHB-4 | TAATAATAA |
| AS$HAHB4_10 | 591 (−) | 1 | 87.5 | HAHB-4 | TAATGATAC |
| AS$HAHB4_23 | 591 (−) | 1 | 87.5 | HAHB-4 | TAATGATAC |
| AS$HAHB4_06 | 591 (−) | 1 | 87.5 | HAHB-4 | TAATAATAA |

TABLE 12-continued

| Identifier | Position | Mismatches | Score | Binding Factor | Sequence - Seq ID NO |
|---|---|---|---|---|---|
| CAMV$35SR_02 | 372 (-) | 0 | 100 | HBP-1 | ACGTCT |
| CAMV$35SR_02 | 372 (+) | 0 | 100 | HBP-1 | AGACGT |
| AS$HVH21_20 | 422 (-) | 0 | 100 | KNOX3 | TGACTGAC |
| PV$PAL2_06 | 1047 (-) | 1 | 87.5 | LBM1 | CACCTACCA |
| PV$PAL2_06 | 1575 (+) | 1 | 87.5 | LBM1 | CACCTACCA |
| MAIZE$PEPC_01 | 345 (+) | 0 | 100 | MNB1b, MNF1 | TGCCCTT |
| NT$PR1A_02 | 620 (-) | 0 | 100 | MYB1 | TAACTG |
| RICE$GLUB1_02 | 808 (+) | 1 | 87.5 | MYB5 | AACAAACTA |
| RICE$GLUB1_03 | 808 (+) | 0 | 100 | MYB5 | AACAAAC |
| AS$MYBAS1_21 | 1819 (+) | 0 | 100 | MYBAS1 | TAACCG |
| NT$NTC12_02 | 1852 (-) | 0 | 100 | NTH15 | TATGTGAC |
| AT$GST6_02 | 373 (+) | 0 | 100 | OBF4 | GACGTG |
| AS$BZIPGCB_01 | 776 (-) | 1 | 88.89 | Opaque-2 | GCCACGTCAC |
| RICE$EM_02 | 1563 (+) | 0 | 100 | OSBZ8 | ACGTG |
| RICE$EM_02 | 374 (+) | 0 | 100 | OSBZ8 | ACGTG |
| RICE$EM_02 | 45 (-) | 0 | 100 | OSBZ8 | ACGTG |
| RICE$EM_02 | 599 (+) | 0 | 100 | OSBZ8 | ACGTG |
| RICE$EM_01 | 1563 (+) | 0 | 100 | OSBZ8, TRAB1 | ACGTG |
| RICE$EM_01 | 374 (+) | 0 | 100 | OSBZ8, TRAB1 | ACGTG |
| RICE$RAB16A_03 | 45 (-) | 0 | 100 | OSBZ8, TRAB1 | TACGTG |
| RICE$EM_01 | 45 (-) | 0 | 100 | OSBZ8 TRAB1 | ACGTG |
| RICE$RAB16A_03 | 598 (+) | 0 | 100 | OSBZ8, TRAB1 | TACGTG |
| RICE$EM_01 | 599 (+) | 0 | 100 | OSBZ8, TRAB1 | ACGTG |
| WHEAT$CATHB_03 | 1808 (+) | 0 | 100 | PBF | AAAAGG |
| WHEAT$CATHB_03 | 1907 (-) | 0 | 100 | PBF | AAAAGG |
| WHEAT$CATHB_03 | 193 (+) | 0 | 100 | PBF | AAAAGG |
| WHEAT$CATHB_03 | 56 (-) | 0 | 100 | PBF | AAAAGG |
| BAR$AMY32B_05 | 56 (+) | 0 | 100 | PBF | CCTTTTC |
| BAR$AMY32B_05 | 764 (-) | 0 | 100 | PBF | CCTTTTC |
| WHEAT$CATHB_03 | 765 (+) | 0 | 100 | PBF | AAAAGG |
| AS$PF1_02 | 1245 (+) | 0 | 100 | PF1 | TTTTT |
| AS$PF1_01 | 1245 (+) | 0 | 100 | PF1 | TTTTT |
| AS$PF1_01 | 1638 (+) | 0 | 100 | PF1 | TTTTT |
| AS$PF1_02 | 1638 (+) | 0 | 100 | PF1 | TTTTT |
| AS$PF1_01 | 1639 (+) | 0 | 100 | PF1 | TTTTT |
| AS$PF1_02 | 1639 (+) | 0 | 100 | PF1 | TTTTT |
| AS$PF1_02 | 1640 (+) | 0 | 100 | PF1 | TTTTT |
| AS$PF1_01 | 1640 (+) | 0 | 100 | PF1 | TTTTT |
| AS$PF1_02 | 1641 (+) | 0 | 100 | PF1 | TTTTT |

TABLE 12-continued

| Identifier | Position | Mismatches | Score | Binding Factor | Sequence - Seq ID NO |
|---|---|---|---|---|---|
| AS$PF1_01 | 1641 (+) | 0 | 100 | PF1 | TTTTT |
| AS$PF1_01 | 1642 (+) | 0 | 100 | PF1 | TTTTT |
| AS$PF1_02 | 1642 (+) | 0 | 100 | PF1 | TTTTT |
| AS$PF1_01 | 1672 (+) | 0 | 100 | PF1 | TTTTT |
| AS$PF1_02 | 1672 (+) | 0 | 100 | PF1 | TTTTT |
| AS$PF1_02 | 1699 (+) | 0 | 100 | PF1 | TTTTT |
| AS$PF1_01 | 1699 (+) | 0 | 100 | PF1 | TTTTT |
| AS$PF1_01 | 1700 (+) | 0 | 100 | PF1 | TTTTT |
| AS$PF1_02 | 1700 (+) | 0 | 100 | PF1 | TTTTT |
| AS$PF1_01 | 1701 (+) | 0 | 100 | PF1 | TTTTT |
| AS$PF1_02 | 1701 (+) | 0 | 100 | PF1 | TTTTT |
| AS$PF1_01 | 1702 (+) | 0 | 100 | PF1 | TTTTT |
| AS$PF1_02 | 1702 (+) | 0 | 100 | PF1 | TTTTT |
| AS$PF1_01 | 1703 (+) | 0 | 100 | PF1 | TTTTT |
| AS$PF1_02 | 1703 (+) | 0 | 100 | PF1 | TTTTT |
| AS$PF1_0 | 1791 (+) | 0 | 100 | PF1 | TTTTT |
| AS$PF1_02 | 1791 (+) | 0 | 100 | PF1 | TTTTT |
| AS$PF1_02 | 1792 (+) | 0 | 100 | PF1 | TTTTT |
| AS$PF1_01 | 1792 (+) | 0 | 100 | PF1 | TTTTT |
| AS$PF1_01 | 1793 (+) | 0 | 100 | PF1 | TTTTT |
| AS$PF1_02 | 1793 (+) | 0 | 100 | PF1 | TTTTT |
| AS$PF1_02 | 1794 (+) | 0 | 100 | PF1 | TTTTT |
| AS$PF1_01 | 1794 (+) | 0 | 100 | PF1 | TTTTT |
| AS$PF1_02 | 1909 (+) | 0 | 100 | PF1 | TTTTT |
| AS$PF1_01 | 1909 (+) | 0 | 100 | PF1 | TTTTT |
| AS$PF1_02 | 1910 (+) | 0 | 100 | PF1 | TTTTT |
| AS$PF1_01 | 1910 (+) | 0 | 100 | PF1 | TTTTT |
| AS$PF1_01 | 192 (-) | 0 | 100 | PF1 | TTTTT |
| AS$PF1_02 | 192 (-) | 0 | 100 | PF1 | TTTTT |
| AS$PF1_01 | 1938 (+) | 0 | 100 | PF1 | TTTTT |
| AS$PF1_02 | 1938 (+) | 0 | 100 | PF1 | TTTTT |
| AS$PF1_01 | 1939 (+) | 0 | 100 | PF1 | TTTTT |
| AS$PF1_02 | 1939 (+) | 0 | 100 | PF1 | TTTTT |
| AS$PF1_02 | 1940 (+) | 0 | 100 | PF1 | TTTTT |
| AS$PF1_01 | 1940 (+) | 0 | 100 | PF1 | TTTTT |
| AS$PF1_01 | 1941 (+) | 0 | 100 | PF1 | TTTTT |
| AS$PF1_02 | 1941 (+) | 0 | 100 | PF1 | TTTTT |
| AS$PF1_01 | 1942 (+) | 0 | 100 | PF1 | TTTTT |

TABLE 12-continued

| Identifier | Position | Mismatches | Score | Binding Factor | Sequence - Seq ID NO |
|---|---|---|---|---|---|
| AS$PF1_02 | 1942 (+) | 0 | 100 | PF1 | TTTTT |
| AS$PF1_02 | 1943 (+) | 0 | 100 | PF1 | TTTTT |
| AS$PF1_01 | 1943 (+) | 0 | 100 | PF1 | TTTTT |
| AS$PE1_01 | 358 (+) | 0 | 100 | PF1 | TTTTT |
| AS$PF1_02 | 358 (+) | 0 | 100 | PF1 | TTTTT |
| AS$PF1_02 | 359 (+) | 0 | 100 | PF1 | TTTTT |
| AS$PF1_01 | 359 (+) | 0 | 100 | PF1 | TTTTT |
| AS$PF1_02 | 558 (+) | 0 | 100 | PF1 | TTTTT |
| AS$PF1_01 | 558 (+) | 0 | 100 | PF1 | TTTTT |
| AS$PF1_02 | 579 (-) | 0 | 100 | PF1 | TTTTT |
| AS$PF1_01 | 579 (-) | 0 | 100 | PF1 | TTTTT |
| AS$PF1_02 | 580 (-) | 0 | 100 | PF1 | TTTTT |
| AS$PF1_01 | 580 (-) | 0 | 100 | PF1 | TTTTT |
| AS$GCCBOX_02 | 1015 (+) | 0 | 100 | Pti4 | GCCGCC |
| AS$RITA1_14 | 776 (-) | 1 | 88.89 | RITA-1 | GCCACGTCAC - 231 |
| PV$PHSB_01 | 777 (-) | 1 | 87.5 | ROM1, ROM2 | GCCACCTCA |
| PV$DLEC2_03 | 777 (-) | 1 | 87.5 | ROM1, ROM2 | GCCACCTCA |
| PV$DLEC2_02 | 777 (-) | 1 | 87.5 | ROM1, ROM2 | GCCACCTCA |
| PV$DLEC2_01 | 777 (-) | 1 | 87.5 | ROM1, ROM2 | GCCACGTCA |
| PV$DLEC2_03 | 889 (+) | 1 | 87.5 | ROM1, ROM2 | GCCACCTCA |
| PV$DLEC2_02 | 889 (+) | 1 | 87.5 | ROM1, ROM2 | GCCACCTCA |
| PV$PHSB_01 | 889 (+) | 1 | 87.5 | ROM1, ROM2 | GCCACCTCA |
| SOYBN$BCGA_05 | 1428 (-) | 0 | 100 | SEF3 | AACCCA |
| SOYBN$BCGA_05 | 279 (+) | 0 | 100 | SEF3 | AACCCA |
| SOYBN$BCGA_04 | 1636 (+) | 1 | 87.5 | SEF4 | CATTTTTGT |
| WHEAT$LMWG1D1_02 | 1334 (+) | 0 | 100 | SPA | GTGTGAC |
| AD$MLP_16 | 559 (-) | 0 | 100 | TBP, TBP-1, TRF | TATAAAA |
| AS$TIZZ_01 | 1769 (-) | 0 | 100 | TIZZ | TTGAC |
| AS$TIZZ_01 | 520 (+) | 0 | 100 | TIZZ | TTGAC |
| WHEAT$EM_02 | 1560 (-) | 1 | 87.5 | Vp1 | ACACGTGCC |
| MAIZE$C1_04 | 506 (+) | 0 | 100 | Vp1 | TGCATG |
| MAIZE$C1_04 | 508 (-) | 0 | 100 | Vp1 | TGCATG |
| MAIZE$C1_04 | 602 (+) | 0 | 100 | Vp1 | TGCATG |
| MAIZE$C1_04 | 745 (-) | 0 | 100 | Vp1 | TGCATG |
| AS$VSF1_01 | 2010 (+) | 1 | 87.5 | VSF-1 | CAACGGTTG |
| PARS$WRKY1_01 | 1768 (-) | 0 | 100 | WRKY1 | TTTGACT |
| PARS$WRKY1_02 | 1768 (-) | 0 | 100 | WRKY1 | TTTGACT |
| PARS$WRKY1_02 | 519 (+) | 0 | 100 | WRKY1 | TTTGACT |
| PARS$WRKY1_01 | 519 (+) | 0 | 100 | WRKY1 | TTTGACT |

TABLE 12-continued

| Identifier | Position | Mismatches | Score | Binding Factor | Sequence - Seq ID NO |
|---|---|---|---|---|---|
| AS$WRKY_01 | 1769 (-) | 0 | 100 | WRKY1, WRKY2 | TTGAC |
| AS$WRKY_02 | 1769 (-) | 0 | 100 | WRKY1, WRKY2 | TTGAC |
| AS$WRKY_03 | 1769 (-) | 0 | 100 | WRKY1, WRKY2 | TTGAC |
| AS$WRKY_04 | 1769 (-) | 0 | 100 | WRKY1, WRKY2 | TTGAC |
| AS$WRKY_03 | 520 (+) | 0 | 100 | WRKY1, WRKY2 | TTGAC |
| AS$WRKY_04 | 520 (+) | 0 | 100 | WRKY1, WRKY2 | TTGAC |
| AS$WRKY_01 | 520 (+) | 0 | 100 | WRKY1, WRKY2 | TTGAC |
| AS$WRKY_02 | 520 (+) | 0 | 100 | WRKY1, WRKY2 | TTGAC |
| NT$CHN50_01 | 1337 (-) | 0 | 100 | WRKY1, WRKY3, WRKY4 | GGTCA |
| NT$CHN50_01 | 1455 (+) | 0 | 100 | WRKY1, WRKY3, WRKY4 | GGTCA |
| NT$CHN50_01 | 1633 (+) | 0 | 100 | WRKY1, WRKY3, WRKY4 | GGTCA |
| NT$CHN50_01 | 1768 (+) | 0 | 100 | WRKY1, WRXY3, WRKY4 | AGTCA |
| NT$CHN50_01 | 1851 (+) | 0 | 100 | WRKY1, WRKY3, WRKY4 | GGTCA |
| NT$CHN50_01 | 23 (+) | 0 | 100 | WRKY1, WRKY3, WRKY4 | GGTCA |
| NT$CHN50_01 | 256 (+) | 0 | 100 | WRKY1, WRKY3, WRKY4 | GGTCA |
| NT$CHN50_01 | 425 (+) | 0 | 100 | WRKY1, WRKY3, WRKY4 | AGTCA |
| NT$CHN50_01 | 521 (-) | 0 | 100 | WRKY1, WRKY3, WRKY4 | AGTCA |
| AT$WRKY18_01 | 1768 (+) | 0 | 100 | WRKY18 | AGTCAA |
| AT$RLK4_01 | 1769 (-) | 0 | 100 | WRKY18 | TTGAC |
| AT$RLK4_02 | 1769 (-) | 0 | 100 | WRKY18 | TTGAC |
| AT$NPR1_01 | 1769 (+) | 0 | 100 | WRKY18 | GTCAA |
| AT$WRKY18_01 | 520 (-) | 0 | 100 | WRKY18 | AGTCAA |
| AT$NPR1_01 | 520 (-) | 0 | 100 | WRKY18 | GTCAA |
| AT$RLK4_01 | 520 (+) | 0 | 100 | WRKY18 | TTGAC |
| AT$RLK4_02 | 520 (+) | 0 | 100 | WRKY18 | TTGAC |
| AS$TWRKY_01 | 1769 (-) | 0 | 100 | WRKY3, WRKY4 | TTGAC |
| AS$TWRXY_01 | 520 (+) | 0 | 100 | WRKY3, WRKY4 | TTGAC |
| AS$WZF1_01 | 240 (+) | 0 | 100 | WZF1 | CACTC |
| WHEAT$H3_03 | 240 (+) | 0 | 100 | WZF1 | CACTC |
| WHEAT$H3_02 | 240 (+) | 0 | 100 | WZF1 | CACTC |

Example 17

Cloning of the CVY-CIK1 Promoter (P-Zm.CVY-CIK1) with Actin 1 Intron into GUS Transformation Vector The CVY-CIK1 promoter fragment plus native leader and actin 1 intron in pMON42366 along with the coding region of GUS reporter gene is flanked by restriction sites NotI and EcoRI. pMON42366 was digested with NotI-EcoRI and the isolated fragment(promoter+leader+actin 1 intron+GUS coding region was then ligated into the backbone of pMON77951, which was also cut with NotI and EcoRI, in order to remove the I-Zm.DnaK and GUS coding region from the construct (which will be replaced by the CVY-CIK1 promoter, leader, actin 1 intron with GUS to make pMON84015.

Digestion of pMON42366 to Isolate the CVY-CIK1 Promoter, Leader, Actin 1 Intron with GUS Coding Region:
1. Digest pMON42366 DNA and pMON77951 DNA with NotI restriction enzyme (New England Biolabs #R0189L) and EcoRI (New England Biolabs #R0101S) in restriction buffer 3 (New England Biolabs) with BSA (New England Biolabs) at 37 C for 60 minutes.

2. Run each reaction on an agarose gel, and gel purify the expected approx. 3478 bp fragment from pMON42366 and the 4452 bp backbone from pMON77951 using the Qiagen Gel Purification kit as directed by the manufacturer.

To produce pMON84015, the isolated CVY-CIK1 promoter, leader, actin 1 intron fragment with GUS was ligated with the pMON77951 backbone fragment using T4 DNA Ligase (#EL0014, MBI Fermentas). pMON84015 was the transformation vector used for corn transformation by gene gun.

Example 18

Cloning of the CVY-CIK1 (P-Zm.CVY-CIK1) Promoter without Intron into a GUS Transformation Vector The CVY-CIK1 promoter fragment without intron in pMON42365 along with the coding region of GUS reporter gene is flanked by restriction sites NotI and EcoRI. pMON42365 was digested with NotI-EcoRI and the isolated fragment(promoter+leader+GUS coding region was then ligated into the backbone of pMON77951, which was also cut with NotI and EcoRI, in order to remove the I-Zm.DnaK and GUS coding region from the construct (which will be replaced by the CVY-CIK1 promoter, leader and GUS to make pMON84018.

Digestion of pMON42365 to Isolate the CVY-CIK1 Promoter, Leader with GUS Coding Region:
1. Digest pMON42365 DNA and pMON77951 DNA with NotI restriction enzyme (New England Biolabs #R0189L) and EcoRI (New England Biolabs #R0101S) in restriction buffer 3 (New England Biolabs) with BSA (New England Biolabs) at 37 C for 60 minutes.
2. Run each reaction on an agarose gel, and gel purify the expected 2987 bp fragment from pMON42365 and the 4452 bp backbone from pMON77951 using the Qiagen Gel Purification kit as directed by the manufacturer.

To produce pMON84018, the isolated CVY-CIK1 promoter, leader, with GUS was ligated with the pMON77951 backbone fragment using T4 DNA Ligase (#EL0014, MBI Fermentas). pMON84018 was the transformation vector used for corn transformation by gene gun.

Example 19

Cloning of the CVY-CIK1 (P-Zm.CVY-CIK1) Promoter without Intron into GUS Transformation Vector The CVY-CIK1 promoter fragment without intron in pMON42365 along with the coding region of GUS reporter gene is flanked by restriction sites NotI and EcoRI. pMON42365 was digested with NotI-EcoRI and the isolated fragment(promoter+leader+GUS coding region was then ligated into the backbone of pMON77951, which was also cut with NotI and EcoRI, in order to remove the I-Zm.DnaK and GUS coding region from the construct (which will be replaced by the CVY-CIK1 promoter, leader and GUS to make pMON84018.

Digestion of pMON42365 to Isolate the CVY-CIK1 Promoter, Leader with GUS Coding Region:
1. Digest pMON42365 DNA and pMON77951 DNA with NotI restriction enzyme (New England Biolabs #R0189L) and EcoRI (New England Biolabs #R0101S) in restriction buffer 3 (New England Biolabs) with BSA (New England Biolabs) at 37 C for 60 minutes.
2. Run each reaction on an agarose gel, and gel purify the expected 2987 bp fragment from pMON42365 and the 4452 bp backbone from pMON77951 using the Qiagen Gel Purification kit as directed by the manufacturer.

To produce pMON84018 (FIG. 24), the isolated CVY-CIK1 promoter, leader, with GUS was ligated with the pMON77951 backbone fragment using T4 DNA Ligase (#EL0014, MBI Fermentas). pMON84018 was the transformation vector used for corn transformation by gene gun.

Example 20

R0 generation transgenic plants were subjected to cold stress. Plants were at V4 to V5 stage. Leaf samples were collected before and after stress for quantitative GUS analysis Treatments: a. unstressed
b. cold (10 degree celcius for 24 h in presence of 800 micro mole/mt2/sec GUS Activity: One μg of total protein was taken in 25 ul of phosphate buffer and to that 25 ul of 2 mM MUG was added and incubated at 37° C. for 1 h. The reaction was stopped by 0.2 M sodium carbonate buffer. Later the activity was measured using fluoromax and expressed as pmole/μg of protein/h. Results are shown in Table 13.

TABLE 13

| | | GUS activity: pmole/μg total protein/h | |
| --- | --- | --- | --- |
| | Events (pedigree No.) | Before stress | After cold stress |
| 1 | ZM_B17773 | <0.1 | 28.38 |
| 2 | ZM_B17775 | 44.90 | 844.84 |
| 3 | ZM_B17781 | 22.73 | 689.84 |
| 4 | ZM_B17783 | <0.1 | <0.1 |
| 5 | ZM_B17786 | 52.94 | 3611.60 |
| 6 | ZM_B17788 | 268.60 | 4095.22 |
| 7 | ZM_B17792 | 6.07 | 3196.21 |
| 8 | ZM_B17794 | 48.79 | 1234.84 |
| 9 | ZM_B17796 | 28.93 | 79.46 |
| 10 | ZM_B17798 | 47.37 | 1748.90 |
| 11 | ZM_B17800 | <0.1 | 47.50 |
| 12 | ZM_B17804 | <0.1 | <0.1 |
| 13 | ZM_B17806 | <0.1 | 101.38 |
| 14 | ZM_B17808 | 55.36 | 3582.06 |
| 15 | ZM_B17816 | <0.1 | <0.1 |
| 16 | ZM_B17825 | 50.35 | 10.02 |
| 17 | ZM_B17827 | <0.1 | <0.1 |
| 18 | ZM_B17830 | <0.1 | <0.1 |
| 19 | ZM_B17832 | 117.48 | 1397.38 |
| 20 | ZM_B17834 | <0.1 | <0.1 |
| 21 | ZM_B17837 | 129.49 | 640.93 |
| 22 | ZM_B17839 | 496.53 | 3242.86 |
| 23 | ZM_B17842 | 110.10 | 6796.83 |
| 24 | ZM_B17846 | <0.1 | 4731.18 |
| 25 | ZM_B17849 | 39.59 | 161.26 |
| 26 | ZM_B17854 | <0.1 | <0.1 |
| 27 | ZM_B17856 | 205.98 | 737.71 |
| 28 | ZM_B17862 | <0.1 | 1161.20 |
| 29 | ZM_B17864 | 158.15 | 276.91 |
| 30 | ZM_B17866 | <0.1 | 942.42 |
| 31 | ZM_B17868 | 1876.32 | 2619.45 |
| 32 | ZM_B17872 | 865.34 | 1402.68 |
| 33 | ZM_B17874 | 21.38 | 832.38 |
| 34 | ZM_B17876 | 15.73 | 1087.16 |
| 35 | ZM_B17880 | 5.70 | 242.61 |
| 36 | ZM_B17882 | <0.1 | <0.1 |
| 37 | ZM_B17886 | 7.55 | 446.61 |
| 38 | ZM_B17888 | 288.11 | 1573.04 |
| 39 | ZM_B17890 | <0.1 | 44.43 |
| 40 | ZM_B17892 | 1045.72 | 2477.10 |
| 41 | ZM_B17894 | 950.06 | 3332.84 |
| 42 | ZM_B17896 | 27.24 | 132.86 |
| 43 | ZM_B17898 | <0.1 | 119.99 |

TABLE 13-continued

| | GUS activity: pmole/µg total protein/h | |
|---|---|---|
| Events (pedigree No.) | Before stress | After cold stress |
| 44 ZM_B17900 | 1280.78 | 5245.11 |
| 45 ZM_B17902 | 1715.94 | 1977.84 |
| 46 ZM_B17904 | 4.48 | 70.78 |

Example 21

Homologous promoters, such as the promoter driving the homologous gene in rice can also be tested for cold induction. Similar experiments to those done in corn above could be done in corn with the rice promoter driving a reporter such as GUS. It would also be possible to test the same promoters for cold, and other stress induction, in corn, wheat, soybean, *Arabidopsis*, and many other plants.

What is claimed is:

1. An isolated nucleic acid sequence that is capable of initiating transcription in a plant cell, said nucleic acid sequence selected from the group consisting of: (a) a nucleic acid sequence comprising SEQ ID NO: 1, and (b) a nucleic acid sequence at least 98% identical to SEQ ID NO: 1.

2. The isolated nucleic acid sequence of claim 1 wherein said nucleic acid sequence comprises SEQ ID NO: 1.

3. A recombinant DNA molecule comprising a promoter, and a polynucleotide operably linked to said promoter, wherein said promoter comprises the isolated nucleic acid sequence of claim 1.

4. A transgenic plant, seed or other propagule of said plant having stably incorporated in its genome the recombinant DNA molecule of claim 3.

5. The transgenic plant, seed or other propagule of claim 4 wherein said plant, seed or other propagule is a monocotyledonous species.

6. The transgenic plant, seed or other propagule of claim 5 wherein said monocotyledonous species is corn.

7. The transgenic plant of claim 4 wherein said plant is a dicot.

8. The transgenic plant of claim 4 wherein said plant is selected from the group consisting of wheat, maize, rye, rice, oat, barley, turfgrass, sorghum, millet, sugarcane, tobacco, tomato, potato, soybean, cotton, canola, alfalfa, sunflower, strawberry, and cotton.

9. The transgenic plant of claim 4 wherein said polynucleotide in said recombinant DNA molecule confers enhanced cold tolerance to said transgenic plant as compared to a plant of the same species lacking said recombinant DNA molecule.

10. The transgenic plant of claim 4, wherein said polynucleotide in said recombinant DNA molecule confers disease resistance to said transgenic plant as compared to a plant of the same species lacking said recombinant DNA molecule.

11. The transgenic plant of claim 4, wherein said polynucleotide in said recombinant DNA molecule confers enhanced abiotic stress tolerance to said transgenic plant as compared to a plant of the same species lacking said recombinant DNA molecule.

12. The transgenic plant of claim 4, wherein said polynucleotide in said recombinant DNA molecule confers enhanced salt tolerance to said transgenic plant as compared to a plant of the same species lacking said recombinant DNA molecule.

13. The transgenic plant of claim 4, wherein said polynucleotide in said recombinant DNA molecule confers enhanced cold germination to said transgenic plant as compared to a plant of the same species lacking said recombinant DNA molecule.

14. The transgenic plant of claim 4, wherein said polynucleotide in said recombinant DNA molecule confers enhanced drought tolerance to said transgenic plant as compared to a plant of the same species lacking said recombinant DNA molecule.

15. The transgenic plant of claim 4, wherein said polynucleotide in said recombinant DNA molecule confers enhanced freezing tolerance to said transgenic plant as compared to a plant of the same species lacking said recombinant DNA molecule.

16. The transgenic plant of claim 4, wherein said polynucleotide in said recombinant DNA molecule confers enhanced biotic stress tolerance to said transgenic plant as compared to a plant of the same species lacking said recombinant DNA molecule.

17. The transgenic plant of claim 4, wherein said polynucleotide in said recombinant DNA molecule confers insect resistance to said transgenic plant as compared to a plant of the same species lacking said recombinant DNA molecule.

18. The transgenic plant of claim 4, wherein said polynucleotide in said recombinant DNA molecule confers herbicide tolerance to said transgenic plant as compared to a plant of the same species lacking said recombinant DNA molecule.

19. The transgenic plant of claim 4, wherein said polynucleotide in said recombinant DNA molecule confers increased yield in said transgenic plant as compared to a plant of the same species lacking said recombinant DNA molecule.

20. A plant germinated from the seed of claim 4.

21. A field of plants germinated from said seeds of claim 4.

22. Seeds produced from the field of claim 21, which comprise said recombinant DNA molecule.

23. A method of producing a transgenic plant that has increased yield comprising the steps of: a) inserting into the genome of a plant cell a recombinant nucleic acid comprising a first nucleic acid sequence according to claim 1, operably linked to a second nucleic acid sequence conferring increased yield, wherein the second nucleic acid sequence is operably linked to a transcription termination polynucleotide that functions in plants, wherein said first nucleic acid sequence is heterologous to said second nucleic acid sequence; b) obtaining a transformed plant cell comprising the recombinant nucleic acid; c) regenerating a transgenic plant from said transformed plant cell; and d) selecting said transgenic plant for enhanced yield as compared to a plant of the same species lacking said recombinant nucleic acid, and wherein expression of said second nucleic acid sequence in said transgenic plant results in said increased yield in the transgenic plant.

24. A transgenic plant produced by the method of claim 23.

25. A method of producing a transgenic plant that has improved cold germination comprising the steps of: a) inserting into the genome of a plant cell a recombinant nucleic acid comprising a first nucleic acid sequence according to claim 1, operably linked to a second nucleic acid sequence conferring improved cold germination, wherein the second nucleic acid sequence is operably linked to a transcription termination polynucleotide that functions in plants, and wherein said first nucleic acid sequence is heterologous to said second nucleic acid sequence; b) obtaining a transformed plant cell comprising the recombinant nucleic acid; c) regenerating a transgenic plant from said transformed plant cell; and d) selecting said transgenic plant for improved cold germination as compared to a plant of the same species lacking said recombinant nucleic acid, and wherein expression of said second nucleic acid sequence in said transgenic plant results in said improved cold germination in the transgenic plant.

26. A transgenic plant produced by the method of claim 25.

27. The recombinant DNA molecule of claim 3, wherein the isolated nucleic acid sequence comprises SEQ ID NO: 1.

28. The transgenic plant, seed or other propagule of claim 4, wherein the isolated nucleic acid sequence comprises SEQ ID NO: 1.

\* \* \* \* \*

UNITED STATES PATENT AND TRADEMARK OFFICE
CERTIFICATE OF CORRECTION

PATENT NO. : 7,659,448 B2 Page 1 of 1
APPLICATION NO. : 10/827659
DATED : February 9, 2010
INVENTOR(S) : Ahrens et al.

It is certified that error appears in the above-identified patent and that said Letters Patent is hereby corrected as shown below:

In claim 23, column 157, line 4, delete "plants, wherein" and insert --plants, and wherein--.

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,659,448 B2 |
| APPLICATION NO. | : 10/827659 |
| DATED | : February 9, 2010 |
| INVENTOR(S) | : Ahrens et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 161 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,659,448 B2 | Page 1 of 1 |
| APPLICATION NO. | : 10/827659 | |
| DATED | : February 9, 2010 | |
| INVENTOR(S) | : Ahrens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this
Twenty-sixth Day of April, 2011

David J. Kappos
*Director of the United States Patent and Trademark Office*

SEQUENCE LISTING

<160> NUMBER OF SEQ ID NOS: 231

<210> SEQ ID NO 1
<211> LENGTH: 2091
<212> TYPE: DNA
<213> ORGANISM: Zea mays

<400> SEQUENCE: 1

```
atccacgctc gctcgggtgt cgggtcagat cgatccagtt ggcgcacgta ataatccttt      60
tccccagaag gagtcgaacc cctcctcccc gtccaatcca atcaaagcga ccaatcgact     120
ggctgtccta cacacacaca aaaccgaccg aggcgacaca ccgcagcagt gatcattctg     180
agcatttgca gaaaaaggag aacgtcccga aatcctggtg gttgtattgt gtgattgctc     240
actcagtccg tgcagggtca gggtgaagcc aagccaacaa cccaacgctc gctgggagta     300
gggtccaccg gatttattgg cagtacatcg ctgtttggtc ctcctgccct tcgcttattt     360
tttaattcgg cagacgtgca cagacagggc accaccggac caaggaaggg cgcacaccgt     420
cgtcagtcac caggtgggtg tgatcagcag ccgcttctct tgtgctgctt tatagcgtat     480
gaaattccag tgtccctgtt ccacctgcat gcaattggtt tgactgaaca acatgatagc     540
aagtgatact atatatattt ttatagagga acacagtgaa aaaatattta gtattattac     600
gtgcatgaaa ttgtattcac agttatccct gatgcaacgc aattgttcaa tatatagcag     660
tatatattat acgaagtata tatgtatatc taatttttatg agaccgggag aaggtgtatt     720
cacagtacag tgcagggcca tggccatgca gcccttgggg cctgaaaagg gtcgcgtgaa     780
gtggccaacg ctgtgcaatt gcaaccaaac aaacttttgg tggcggggtc cctgtccctg     840
gccggctttg cccacaggcc acagcgcatc acaccaccgc tttatagcgc cacccccacca     900
ccctcgtctc tccccccgtc gagcacacaa cacaccctcc tcgtcctcca atccaatcaa     960
cctggtagac tcgcttcgct tctcccccca gctcggacgg agctcctcgc agcagccgcc    1020
gatcaacctg cgctcgggct cagcgctgga aggtgagagc tcagtgcctc gtcccgcccg    1080
ccccaaatct ggttcttgtg ctggctctgg ctgtgcgctg cacgaattct gcatctggtt    1140
ctttcgagac gcaattcccg gaccgtgggc tttggtttcg gaggggccg agagtaaggc    1200
gttaggactt tctccgagct gcaaggccgc tcgtcgttgc ggcatttttc gtttcgcttg    1260
tcctgtgatg agagatgtgc atttcccttt ggcgggctta ccgttccctg ctcgtctgta    1320
tgtgtgtatg tttgtgtgac cttccctca acgccaggct cttctcccct cttgctgttt    1380
ctttcagcag tacagacgcg catctgtaca gcgcctttct tcggtcctgg gttatgattg    1440
atccgttaac agttggtcac caagtgctgg ctgttaata tgtactataa gcttcttggt    1500
gccgctgcct ctgcctatac gactttatgc gctgcctgca caagtctcag ccatctgtgg    1560
```

-continued

```
gaacgtgtgt ctctcaccta cctttcatat tgcactagct ggattgaatc attctgcttt      1620
ggagagatgt ccggtcattt ttttttaaat cattttcatc tcgcgtacta gttttgtttt      1680
tgttttgcga gagagtaatt ttttttttaat atttactgtc tcctgtccca tttgctgttt     1740
ctttacccag aaatttccac cagattcagt caaacgaaac tcctgtgctc tttttttttct    1800 cccttttcaaa agggtgtgta accgactacc gactcagata atataagtgc ggtcacatat     1860
cacatgatat catctcgcct ctctcccttc tcctgtgttt tattttcctt ttttctaacc     1920
acagcgtgat gaacttcttt tttttttggg ggggggggg gggtaacta cagcttagcg       1980 aacatgaatg ggtagtttta caactaatgc aacggctggt tcactgaaca actgtaggtg     2040
ttggaagaga atagcctgaa ggttcacagt aaccttcatc tgtcggaagc c              2091
```

<210> SEQ ID NO 2
<211> LENGTH: 25
<212> TYPE: DNA
<213> ORGANISM: Artificial
<220> FEATURE:
<223> OTHER INFORMATION: PCR primer

<400> SEQUENCE: 2
tcggtgacaa tgcagccctc ttagc                                              25

<210> SEQ ID NO 3
<211> LENGTH: 30
<212> TYPE: DNA
<213> ORGANISM: Artificial
<220> FEATURE:
<223> OTHER INFORMATION: PCR primer

<400> SEQUENCE: 3
agccatggct tccgacagat gaaggttact                                         30

<210> SEQ ID NO 4
<211> LENGTH: 23
<212> TYPE: DNA
<213> ORGANISM: Artificial
<220> FEATURE:
<223> OTHER INFORMATION: PCR primer

<400> SEQUENCE: 4
atccgccgcc gatggaagag gag                                                23

<210> SEQ ID NO 5
<211> LENGTH: 28
<212> TYPE: DNA
<213> ORGANISM: Artificial
<220> FEATURE:
<223> OTHER INFORMATION: PCR primer

<400> SEQUENCE: 5
atctgcagat ccacgctcgc tcgggtgt                                           28

<210> SEQ ID NO 6
<211> LENGTH: 80
<212> TYPE: DNA
<213> ORGANISM: Artificial
<220> FEATURE:
<223> OTHER INFORMATION: PCR primer

<400> SEQUENCE: 6
agccatggct tccgacagat gaaggttact gtgaaccttc aggttattct cttccaacac      60
cttccagcgc tgagcccgag                                                    80

```
<210> SEQ ID NO 7
<211> LENGTH: 60
<212> TYPE: DNA
<213> ORGANISM: Artificial
<220> FEATURE:
<223> OTHER INFORMATION: PCR primer

<400> SEQUENCE: 7
agccatggct tccgacagat gaaggttact gtgaaccttc aggctattct cttccaacac    60

<210> SEQ ID NO 8
<211> LENGTH: 19
<212> TYPE: DNA
<213> ORGANISM: Artificial
<220> FEATURE:
<223> OTHER INFORMATION: PCR primer

<400> SEQUENCE: 8
tgaactttcc actggacgg                                                 19

<210> SEQ ID NO 9
<211> LENGTH: 22
<212> TYPE: DNA
<213> ORGANISM: Artificial
<220> FEATURE:
<223> OTHER INFORMATION: PCR primer

<400> SEQUENCE: 9
tgaagtaata catcatcgaa ca                                             22

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
aaccgttcta ctttactggc                                                20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
cattgacgca ggtgatcgga                                                20

<210> SEQ ID NO 12
<211> LENGTH: 23
<212> TYPE: DNA
<213> ORGANISM: Artificial
<220> FEATURE:
<223> OTHER INFORMATION: PCR primer

<400> SEQUENCE: 12
cccagtcacg acgttgtaaa acg                                            23

<210> SEQ ID NO 13
<211> LENGTH: 23
<212> TYPE: DNA
<213> ORGANISM: Artificial
<220> FEATURE:
```

<223> OTHER INFORMATION: PCR primer

<400> SEQUENCE: 13
agcggataac aatttcacac agg    23

<210> SEQ ID NO 14
<211> LENGTH: 907
<212> TYPE: DNA
<213> ORGANISM: Zea mays

<400> SEQUENCE: 14

```
atccacgctc gctcgggtgt cgggtcagat cgatccagtt ggcgcacgta ataatccttt      60
tccccagaag gagtcgaacc cctcctcccc gtccaatcca atcaaagcga ccaatcgact     120
ggctgtccta cacacacaca aaaccgaccg aggcgcacaca ccgcagcagt gatcattctg    180
agcatttgca gaaaaaggag aacgtcccga aatcctggtg gttgtattgt gtgattgctc    240
actcagtccg tgcagggtca gggtgaagcc aagccaacaa cccaacgctc gctgggagta    300
gggtccaccg gatttattgg cagtacatcg ctgtttggtc ctcctgccct tcgcttattt    360
tttaattcgg cagacgtgca cagacagggc accaccggac caaggaaggg cgcacaccgt    420
cgtcagtcac caggtgggtg tgatcagcag ccgcttctct tgtgctgctt tatagcgtat    480
gaaattccag tgtccctgtt ccacctgcat gcaattggtt tgactgaaca acatgatagc    540
aagtgatact atatatattt ttatagagga acacagtgaa aaaatattta gtattattac    600
gtgcatgaaa ttgtattcac agttatccct gatgcaacgc aattgttcaa tatatagcag    660
tatatattat acgaagtata tatgtatatc taattttatg agaccgggag aaggtgtatt    720
cacagtacag tgcagggcca tggccatgca gcccttgggg cctgaaaagg gtcgcgtgaa    780
gtggccaacg ctgtgcaatt gcaaccaaac aaacttttgg tggcggggtc cctgtccctg    840
gccggctttg cccacaggcc acagcgcatc acaccaccgc tttatagcgc caccccacca    900
ccctcgt                                                              907
```

<210> SEQ ID NO 15
<211> LENGTH: 1039
<212> TYPE: DNA
<213> ORGANISM: Zea mays

<400> SEQUENCE: 15

```
gtgagagctc agtgcctcgt cccgcccgcc ccaaatctgg ttcttgtgct ggctctggct      60
gtgcgctgca cgaattctgc atctggttct ttcgagacgc aattcccgga ccgtgggctt    120
tggtttcgga gggggccgag agtaaggcgt taggactttc tccgagctgc aaggccgctc    180
gtcgttgcgg catttttcgt ttcgcttgtc ctgtgatgag agatgtgcat ttcccttttgg   240
cgggcttacc gttccctgct cgtctgtatg tgtgtatgtt tgtgtgaacct ttccctcaac   300
gccaggctct tctcccctct tgctgtttct ttcagcagta cagacgcgca tctgtacagc    360
gcctttcttc ggtcctgggt tatgattgat ccgttaacag ttggtcacca agtgctggct    420
gtttaatatg tactataagc ttcttggtgc cgctgcctct gcctatacga ctttatgcgc    480
tgcctgcaca agtctcagcc atctgtggga acgtgtgtct ctcacctacc tttcatattg    540
cactagctgg attgaatcat tctgcttttgg agagatgtcc ggtcattttt ttttaaatca    600
ttttcatctc gcgtactagt ttttgttttg ttttgcgaga gagtaatttt tttttaatat    660
ttactgtctc ctgtcccatt tgctgtttct ttacccagaa atttccacca gattcagtca    720
aacgaaactc ctgtgctctt tttttttctcc cttttcaaaag ggtgtgtaac cgactaccga    780
```

```
ctcagataat ataagtgcgg tcacatatca catgatatca tctcgcctct ctcccttctc    840
ctgtgtttta ttttccttt ttctaaccac agcgtgatga acttctttt tttttggggg      900 ggggggggg ggtaactaca gcttagcgaa catgaatggg tagttttaca actaatgcaa    960
cggctggttc actgaacaac tgtaggtgtt ggaagagaat agcctgaagg ttcacagtaa   1020
ccttcatctg tcggaagcc                                                 1039

<210> SEQ ID NO 16
<211> LENGTH: 1597
<212> TYPE: DNA
<213> ORGANISM: Artificial
<220> FEATURE:
<223> OTHER INFORMATION: Corn promoter with rice DNA enhancer added

<400> SEQUENCE: 16
gatccacgct cgctcgggtg tcgggtcaga tcgatccagt tggcgcacgt aataatcctt     60
ttccccagaa ggagtcgaac ccctcctccc cgtccaatcc aatcaaagcg accaatcgac    120
tggctgtcct acacacacac aaaaccgacc gaggcgacac accgcagcag tgatcattct    180
gagcatttgc agaaaaagga gaacgtcccg aaatcctggt ggttgtattg tgtgattgct    240
cactcagtcc gtgcagggtc agggtgaagc caagccaaca acccaacgct cgctgggagt    300
agggtccacc ggatttattg gcagtacatc gctgtttggt cctcctgccc ttcgcttatt    360
ttttaattcg gcagacgtgc acagacaggg caccaccgga ccaaggaagg gcgcacaccg    420
tcgtcagtca ccaggtgggt gtgatcagca gccgcttctc ttgtgctgct ttatagcgta    480
tgaaattcca gtgtccctgt tccacctgca tgcaattggt ttgactgaac aacatgatag    540
caagtgatac tatatatatt tttatagagg aacacagtga aaaaatattt agtattatta    600
cgtgcatgaa attgtattca cagttatccc tgatgcaacg caattgttca atatatagca    660
gtatatatta tacgaagtat atatgtatat ctaattttat gagaccggga gaaggtgtat    720
tcacagtaca gtgcagggcc atggccatgc agcccttggg gcctgaaaag ggtcgcgtga    780
agtggccaac gctgtgcaat tgcaaccaaa caaactttg gtggcggggt ccctgtccct     840
ggccggcttt gcccacaggc cacagcgcat cacaccaccg ctttatagcg ccaccccacc    900
accctcgtct ctccccccgt cgagcacaca acacacccctc ctcgtcctcc aatccaatca    960
acctggtaga ctcgcttcgc ttctccccc agctcggacg gagctcctcg cagcagccgc   1020
cgatcaacct cgctcgggc tcagcgctgg aaggtgttgg aagagaatag cctgaaggtt   1080
cacagtaacc ttcatctgtc ggaagccctc cgccgccgcc ggtaaccacc ccgcccctct   1140
cctctttctt tctccgtttt tttttccgtc tcggtctcga tctttggcct tggtagtttg   1200
ggtgggcgag aggcggcttc gtgcgcgccc agatcggtgc gcgggagggg cgggatctcg   1260
cggctggggc tctcgccggc gtggatccgg cccggatctc gcggggaatg gggctctcgg   1320
atgtagatct gcgatccgcc gttgttgggg gagatgatgg ggggtttaaa atttccgccg   1380
tgctaaacaa gatcaggaag aggggaaaag ggcactatgg tttatatttt tatatatttc   1440
tgctgcttcg tcaggcttag atgtgctaga tctttctttc ttcttttgt gggtagaatt    1500 tgaatccctc agcattgttc atcggtagtt tttcttttca tgatttgtga caaatgcagc   1560
ctcgtgcgga gctttttgt aggtagaagt gatcaac                             1597

<210> SEQ ID NO 17
<211> LENGTH: 1106
<212> TYPE: DNA
```

<210> ORGANISM: Artificial
<220> FEATURE:
<223> OTHER INFORMATION: Zea mays CVY-CIK1p from Wigor line with 5' UTR intact, but intron removed

<400> SEQUENCE: 17

```
atccacgctc gctcgggtgt cgggtcagat cgatccagtt ggcgcacgta ataatccttt    60
tccccagaag gagtcgaacc cctcctcccc gtccaatcca atcaaagcga ccaatcgact   120
ggctgtccta cacacacaca aaaccgaccg aggcgacaca ccgcagcagt gatcattctg   180
agcatttgca gaaaaaggag aacgtcccga atcctggtg gttgtattgt gtgattgctc   240
actcagtccg tgcagggtca gggtgaagcc aagccaacaa cccaacgctc gctgggagta   300
gggtccaccg gatttattgg cagtacatcg ctgtttggtc ctcctgccct tcgcttattt   360
tttaattcgg cagacgtgca cagacagggc accaccggac caaggaaggg cgcacaccgt   420
cgtcagtcac caggtgggtg tgatcagcag ccgcttctct tgtgctgctt tatagcgtat   480
gaaattccag tgtccctgtt ccacctgcat gcaattggtt tgactgaaca acatgatagc   540
aagtgatact atatatattt ttatagagga acacagtgaa aaaatattta gtattattac   600
gtgcatgaaa ttgtattcac agttatccct gatgcaacgc aattgttcaa tatatagcag   660
tatatattat acgaagtata tatgtatatc taattttatg agaccgggag aaggtgtatt   720
cacagtacag tgcagggcca tggccatgca gcccttgggg cctgaaaagg gtcgcgtgaa   780
gtggccaacg ctgtgcaatt gcaaccaaac aaacttttgg tggcggggtc cctgtccctg   840
gccggctttg cccacaggcc acagcgcatc acaccaccgc tttatagcgc caccccacca   900
ccctcgtctc tcccccgtc gagcacacaa cacaccctcc tcgtcctcca atccaatcaa    960
cctggtagac tcgcttcgct tctcccccca gctcggacgg agctcctcgc agcagccgcc  1020
gatcaacctg cgctcgggct cagcgctgga aggtgttgga agagaatagc ctgaaggttc  1080
acagtaacct tcatctgtcg gaagcc                                        1106
```

<210> SEQ ID NO 18
<211> LENGTH: 3530
<212> TYPE: DNA
<213> ORGANISM: Oryza sativa

<400> SEQUENCE: 18

```
ggcttcccgc tgtgagagaa gtggctgcct ctcggttctc accaagcagt cgaaaatgcc    60
agaacagcga ccagatagga tcatcgtgcc atgcaggcat gcagcctttg agaactgaaa   120
gagccggtga agtcctgca aagcgaaaag caaatgaaca acatctgcc tgtgctgctg    180
cctcgcctcg ctgtccttt ccggtgggtt gccgctgcta acctctgcct ccgcgatacg    240
tgacacgtca tcctccccc accccacccc atgcttgcac ccccccccc cccctccct     300
cccttattac caccacccc ctcctccatc ctcctctgct cctccaacct ggctcagttt    360
cctcctgttc ttgagagaac tgaatctgct gtccagctgc tgctccggct ggtctctgag   420
ttgaaggtaa ggttaatcgg tgtctctcag cctgaatgaa tttgtctatc tcctatggct   480
ttgtggtggt tgaattttgc gttctgggga tgttaggacc ttcttgttgg acaatttct    540
gagattctgg cttgctttgg atgggttggg ggaagagtta ggtgcttgct ggtgtgtatt   600
tcttttgcat ttcggttgtc ctgtgaagga tgcgtgttct cggcatttcc agctcattgt   660
gtctttgccc ttcagataac agttatcctc gtgcttttcc ttttcttc agcaaaacat    720
atctggactt ctgtacaagt gcttttttt tcttctttgg acgatattt gttttgcatt    780
```

```
ctagtgattc tgtacaagtg ccatctgata gcatatcatc attcggcaac tggtgatttc      840
ccctatgcgg tctttcatgt acttgcatga ttgaacatat ggcagtgctt ctgtcggatg      900
ctatcgatgt tttacttgcg aaaggccggg aacttttttg cagatcttga ggttttagt       960 agtgatgcag tcattcaaaa agataacctt gtgctggtcc ttttgccttt cggctgcact     1020
tgcatgtgcg ttttctcaga gatgctgcat ctccagctca gcttctgtca tcagtcatta    1080
gtcattgcca tctttatgt ggataaagtc aagttaatt tagcaccgct gttttggagt      1140
tgtttggtca ttttatatat tttcatcagg tgttgtttac tgttcctggt actaaaattt    1200
cgaatttaca aatgactacc tcattctcct ttcttttttt ccttttcct tgtggcagac      1260 cggttcctga aagaatattc ttttcatgaa atgtacttcc ggtttttaa atagaatgat      1320 taaattacag taggatgaat aactaaattt gtcgatatgc cttgtaccgg tactccttgt    1380
tagttcttag tgaatctatg tatactattg cttgtcaaat tgtgaatttt actatcagct    1440
gtatgtatgt ctattgaaga actctcaaca gttctaactt cctaagatgt tttaatcaat    1500
tcttgctacc aacctggata cagtattctc cgtagttttt tcttcatttt tttttttaaag    1560 agatctattg agagtccttg gtacccatct tctgtagaat tgtccatgtg aacagttgct    1620
tcaagatttc tgctgcatct gtgatacggg atcactgata ctgtagtgat cagatccaaa    1680
acacatatat agttcgccac cattctaaaa cacatgtttg tgtgatcaga tctagctcgc    1740
caccatatat agttcaggtt ttcaagttgt aatatcactt gccttttgcg atagatatga    1800
caacacactt tgtgtcaggc tgtcccaatt ttctctgaat tttctctcat atatcatgat    1860
ttagttatgg cttttgttcc ttgacatttc aatgtctaat tgtccaatgt taagtaaatc    1920
cttttcatag cctgatttat tgaatacttg caggtacttg aataacttga aggttcctag    1980
gaaccttcat ttgttggaag atgtataggg ctaagagggc tgcattatct ccaaaggtga    2040
agcgccgtgt agggaagtat gagctcgggc gcaccattgg agaaggaacc tttgcaaagg    2100
tccggtttgc gaagaacact gaaaatgacg aaccagttgc tatcaaaatc cttgacaagg    2160
agaaggttca gaagcacaga ttggttgaac agattaggcg tgaaatttgt actatgaagt    2220
tagtaaagca tcctaatgtt gttcggctgt tcgaggtcat gggaagtaaa gcaagaattt    2280
tcattgttct ggaatatgtt actgaggag agctctttga aatcattgca actaatggaa    2340
ggttgaagga ggaggaagca cgaaaatact ttcaacaact tatcaatgca gttgactact    2400
gccacagtag gggtgtgtac cacagagact tgaagttaga aaatttgctg cttgatgctt    2460
ctggaaacct gaaagtatct gactttggtt tgagtgcttt aaccgagcaa gtgaaggctg    2520
acggtttgct gcacacgaca tgtggaactc ctaattatgt tgctccagag gtgattgagg    2580
acagaggcta tgatgggca gctgcagata tctggtcttg tggggtaatc ctttatgttc    2640
tgcttgctgg gttttaccca tttgaggatg acaacatcat tgctctttat aaaaagatct    2700
ctgaagctca gtttacctgt ccctcttggt ttttctactgg agctaagaag ctgatcacca    2760
gaattctgga tcccaaccct acaactagga tcaccatttc tcaaatactg aagatccttt    2820
ggttcaaaaa gggttacaaa ccgcctgtat ttgacgagaa atatgaaact agttttgacg    2880
atgtcgatgc tgcttttgga gactccgaag accggcatgt caagaagaa actgaagatc    2940 agcctacctc tatgaacgcg tttgaactca tttcactgaa tcaggcactg aatctggaca    3000
atttgttcga ggcaaaaaag gagtataaaa gagagacaag attcacatca caatgtcctc    3060
caaaagaaat tatcaccaag attgaagaag ctgcaaagcc acttggattt gatattcaaa    3120
agaaaaatta caagatgcgc atggagaacc tgaaagcagg tagaaaaggc aatctcaatg    3180
```

-continued

```
ttgcaactga ggttttccaa gtagctccat ccttacatgt ggttgagctc aagaaggcaa    3240 aggggggacac tctggagttc caaaaggtgc cattctttga caccggaaat ttcgctattt   3300
ccaacttgct atttactgcc aagtttaacc aaaatcaatt ctgctgtgaa acaacagttc    3360
tacagaaccc tgtcgaccca gctcaaggac gtggtctgga agtgcgacgg cgaggtcgaa    3420
ggcaacggcg ccgcggcgtg aacgtggttt ttgccatggc tttcggggca ccggttcttc    3480
gtgtacatag ctgctctgcc atcatcaatg gggtgttcgc cgtagagtag                3530

<210> SEQ ID NO 19
<211> LENGTH: 23
<212> TYPE: DNA
<213> ORGANISM: Artificial
<220> FEATURE:
<223> OTHER INFORMATION: primer

<400> SEQUENCE: 19
tatctggtct tgcggagtaa tcc                                             23

<210> SEQ ID NO 20
<211> LENGTH: 23
<212> TYPE: DNA
<213> ORGANISM: Artificial
<220> FEATURE:
<223> OTHER INFORMATION: pcr primer

<400> SEQUENCE: 20
tgtatagggc gatgatgttg tca                                             23

<210> SEQ ID NO 21
<211> LENGTH: 34
<212> TYPE: DNA
<213> ORGANISM: artificial
<220> FEATURE:
<223> OTHER INFORMATION: pcr primer

<400> SEQUENCE: 21
tttgttcttc ttgctggata tttaccttcc gagg                                 34

<210> SEQ ID NO 22
<211> LENGTH: 20
<212> TYPE: DNA
<213> ORGANISM: Artificial
<220> FEATURE:
<223> OTHER INFORMATION: pcr primer

<400> SEQUENCE: 22
aattctgcat gcgtttggac                                                 20

<210> SEQ ID NO 23
<211> LENGTH: 21
<212> TYPE: DNA
<213> ORGANISM: Artificial
<220> FEATURE:
<223> OTHER INFORMATION: pcr primer

<400> SEQUENCE: 23
aagaactcgc acacacatca a                                               21

<210> SEQ ID NO 24
<211> LENGTH: 27
<212> TYPE: DNA
<213> ORGANISM: Artificial
<220> FEATURE:
```

-continued

<223> OTHER INFORMATION: pcr primer

<400> SEQUENCE: 24
tatgctcatt caggttggag ccaattt                              27

<210> SEQ ID NO 25
<211> LENGTH: 20
<212> TYPE: DNA
<213> ORGANISM: Artificial
<220> FEATURE:
<223> OTHER INFORMATION: pcr primer

<400> SEQUENCE: 25
cgtccctgcc ctttgtacac                                      20

<210> SEQ ID NO 26
<211> LENGTH: 21
<212> TYPE: DNA
<213> ORGANISM: Artificial
<220> FEATURE:
<223> OTHER INFORMATION: pcr primer

<400> SEQUENCE: 26
cgaacacttc accggatcat t                                    21

<210> SEQ ID NO 27
<211> LENGTH: 21
<212> TYPE: DNA
<213> ORGANISM: Artificial
<220> FEATURE:
<223> OTHER INFORMATION: pcr primer

<400> SEQUENCE: 27
cgaacacttc accggatcat t                                    21

<210> SEQ ID NO 28
<211> LENGTH: 17
<212> TYPE: DNA
<213> ORGANISM: artificial
<220> FEATURE:
<223> OTHER INFORMATION: motif

<400> SEQUENCE: 28
gtccatctga ccagcgc                                         17

<210> SEQ ID NO 29
<211> LENGTH: 17
<212> TYPE: DNA
<213> ORGANISM: Triticum aestivum

<400> SEQUENCE: 29
gtccatctga ccagccc                                         17

<210> SEQ ID NO 30
<211> LENGTH: 17
<212> TYPE: DNA
<213> ORGANISM: Hordeum vulgare

<400> SEQUENCE: 30
gcctgtttga ccagcgc                                         17

<210> SEQ ID NO 31
<211> LENGTH: 17
<212> TYPE: DNA
<213> ORGANISM: Zea mays

```
<400> SEQUENCE: 31
gtccgtccga ggagcac                                                  17

<210> SEQ ID NO 32
<211> LENGTH: 17
<212> TYPE: DNA
<213> ORGANISM: Zea mays

<400> SEQUENCE: 32
gcgcatctgt acagcgc                                                  17

<210> SEQ ID NO 33
<211> LENGTH: 17
<212> TYPE: DNA
<213> ORGANISM: Hordeum vulgare

<400> SEQUENCE: 33
gctcatcgga caagaac                                                  17

<210> SEQ ID NO 34
<211> LENGTH: 17
<212> TYPE: DNA
<213> ORGANISM: Arabidopsis thaliana

<400> SEQUENCE: 34
gctcatcgga caagaac                                                  17

<210> SEQ ID NO 35
<211> LENGTH: 17
<212> TYPE: DNA
<213> ORGANISM: Arabidopsis thaliana

<400> SEQUENCE: 35
gctcatcgga caagaac                                                  17

<210> SEQ ID NO 36
<211> LENGTH: 17
<212> TYPE: DNA
<213> ORGANISM: Brassica napus

<400> SEQUENCE: 36
ttgcacccgg tgaccgt                                                  17

<210> SEQ ID NO 37
<211> LENGTH: 28
<212> TYPE: DNA
<213> ORGANISM: Artificial
<220> FEATURE:
<223> OTHER INFORMATION: consensus motif

<400> SEQUENCE: 37
agctgagcgt gatcagcagc cgccgctc                                      28

<210> SEQ ID NO 38
<211> LENGTH: 28
<212> TYPE: DNA
<213> ORGANISM: Zea mays

<400> SEQUENCE: 38
agctgagcgt gctccgtatc cgccgctc                                      28

<210> SEQ ID NO 39
```

<211> LENGTH: 28
<212> TYPE: DNA
<213> ORGANISM: Zea mays

<400> SEQUENCE: 39
aggtgggtgt gatcagcagc cgcttctc                                28

<210> SEQ ID NO 40
<211> LENGTH: 40
<212> TYPE: DNA
<213> ORGANISM: Artificial
<220> FEATURE:
<223> OTHER INFORMATION: motif

<400> SEQUENCE: 40
ccgcgggctc ggacgaggac ggtgacatcc gccgccgagc                   40

<210> SEQ ID NO 41
<211> LENGTH: 40
<212> TYPE: DNA
<213> ORGANISM: Triticum aestivum

<400> SEQUENCE: 41
ccgcgtcgtc ggacgggcac ggtgagatgc ggcgtcgggc                   40

<210> SEQ ID NO 42
<211> LENGTH: 40
<212> TYPE: DNA
<213> ORGANISM: Triticum aestivum

<400> SEQUENCE: 42
ccgcggtgtc ggacggggac ggtgagatgc ggtgtcgaac                   40

<210> SEQ ID NO 43
<211> LENGTH: 40
<212> TYPE: DNA
<213> ORGANISM: Triticum aestivum

<400> SEQUENCE: 43
ccgcggccgc catggcggcc gggagcatgc gacgtcgggc                   40

<210> SEQ ID NO 44
<211> LENGTH: 40
<212> TYPE: DNA
<213> ORGANISM: Zea mays

<400> SEQUENCE: 44
cccccagctc ggacggagct cctcgcagca gccgccgatc                   40

<210> SEQ ID NO 45
<211> LENGTH: 40
<212> TYPE: DNA
<213> ORGANISM: Zea mays

<400> SEQUENCE: 45
tagcgccacc ccaccaccct cgtctctccc cccgtcgagc                   40

<210> SEQ ID NO 46
<211> LENGTH: 40
<212> TYPE: DNA
<213> ORGANISM: Triticum aestivum

<400> SEQUENCE: 46
ccgtggcggg ggacgacaac gcggtcagtc gcggcagagg                   40

<210> SEQ ID NO 47
<211> LENGTH: 40
<212> TYPE: DNA
<213> ORGANISM: Hordeum vulgare

<400> SEQUENCE: 47
ccgcgtgcag gcccggggac acgtacacca cctccacatc                               40

<210> SEQ ID NO 48
<211> LENGTH: 40
<212> TYPE: DNA
<213> ORGANISM: Zea mays

<400> SEQUENCE: 48
taacgagctg gctcgagctt cctaacgagc cgagccgagc                               40

<210> SEQ ID NO 49
<211> LENGTH: 40
<212> TYPE: DNA
<213> ORGANISM: Zea mays

<400> SEQUENCE: 49
gagctggctc gttatagtaa cgagtcataa cgagccgagc                               40

<210> SEQ ID NO 50
<211> LENGTH: 40
<212> TYPE: DNA
<213> ORGANISM: Zea mays

<400> SEQUENCE: 50
gcgctggaag gtgagagctc agtgcctcgt cccgcccgcc                               40

<210> SEQ ID NO 51
<211> LENGTH: 40
<212> TYPE: DNA
<213> ORGANISM: Zea mays

<400> SEQUENCE: 51
gagcgtgctc cgtatccgcc gctcccactc cttctccgtc                               40

<210> SEQ ID NO 52
<211> LENGTH: 40
<212> TYPE: DNA
<213> ORGANISM: Hordeum vulgare

<400> SEQUENCE: 52
gcgcgctatc gtcatcgccc ctccatcgcc ggagtcgggc                               40

<210> SEQ ID NO 53
<211> LENGTH: 40
<212> TYPE: DNA
<213> ORGANISM: Zea mays

<400> SEQUENCE: 53
ccgtcgtcag tcaccaggtg ggtgtgatca gcagccgctt                               40

<210> SEQ ID NO 54
<211> LENGTH: 20
<212> TYPE: DNA
<213> ORGANISM: Artificial
<220> FEATURE:
<223> OTHER INFORMATION: consensus sequence -continued

```
<400> SEQUENCE: 54
gccggtcccg tggccgtggc                                               20

<210> SEQ ID NO 55
<211> LENGTH: 20
<212> TYPE: DNA
<213> ORGANISM: Zea mays

<400> SEQUENCE: 55
gcggggtccc tgtccctggc                                               20

<210> SEQ ID NO 56
<211> LENGTH: 20
<212> TYPE: DNA
<213> ORGANISM: Zea mays

<400> SEQUENCE: 56
ggcggtcccg tggccgtggc                                               20

<210> SEQ ID NO 57
<211> LENGTH: 20
<212> TYPE: DNA
<213> ORGANISM: Triticum aestivum

<400> SEQUENCE: 57
gccggatccg tggcggggga                                               20

<210> SEQ ID NO 58
<211> LENGTH: 20
<212> TYPE: DNA
<213> ORGANISM: Brassica napus

<400> SEQUENCE: 58
gccggtcctg atggcttggc                                               20

<210> SEQ ID NO 59
<211> LENGTH: 14
<212> TYPE: DNA
<213> ORGANISM: Artificial
<220> FEATURE:
<223> OTHER INFORMATION: consensus motif

<400> SEQUENCE: 59
gcagcacagt cgtg                                                     14

<210> SEQ ID NO 60
<211> LENGTH: 14
<212> TYPE: DNA
<213> ORGANISM: Hordeum vulgare

<400> SEQUENCE: 60
gcagcacagt cgtg                                                     14

<210> SEQ ID NO 61
<211> LENGTH: 14
<212> TYPE: DNA
<213> ORGANISM: Zea mays

<400> SEQUENCE: 61
gcagtacaga cgcg                                                     14

<210> SEQ ID NO 62
<211> LENGTH: 14
```

```
<212> TYPE: DNA
<213> ORGANISM: Hordeum vulgare

<400> SEQUENCE: 62
gcggtacagt cctg                                                        14

<210> SEQ ID NO 63
<211> LENGTH: 14
<212> TYPE: DNA
<213> ORGANISM: Hordeum vulgare

<400> SEQUENCE: 63
ccatcacagc cgtg                                                        14

<210> SEQ ID NO 64
<211> LENGTH: 20
<212> TYPE: DNA
<213> ORGANISM: Artificial
<220> FEATURE:
<223> OTHER INFORMATION: consensus motif

<400> SEQUENCE: 64
ccatccaccc ctagggaact                                                  20

<210> SEQ ID NO 65
<211> LENGTH: 20
<212> TYPE: DNA
<213> ORGANISM: Zea mays

<400> SEQUENCE: 65
ccatgcagcc cttggggcct                                                  20

<210> SEQ ID NO 66
<211> LENGTH: 20
<212> TYPE: DNA
<213> ORGANISM: Triticum aestivum

<400> SEQUENCE: 66
gcatccacgc gttgggagct                                                  20

<210> SEQ ID NO 67
<211> LENGTH: 20
<212> TYPE: DNA
<213> ORGANISM: Hordeum vulgare

<400> SEQUENCE: 67
ccatacaccc ctacggaact                                                  20

<210> SEQ ID NO 68
<211> LENGTH: 20
<212> TYPE: DNA
<213> ORGANISM: Zea mays

<400> SEQUENCE: 68
gaatccatct ctagggctct                                                  20

<210> SEQ ID NO 69
<211> LENGTH: 22
<212> TYPE: DNA
<213> ORGANISM: Artificial
<220> FEATURE:
<223> OTHER INFORMATION: consensus motif

<400> SEQUENCE: 69
```

| | |
|---|---|
| gctggccgac gtacacaagc tt | 22 |

<210> SEQ ID NO 70
<211> LENGTH: 22
<212> TYPE: DNA
<213> ORGANISM: Hordeum vulgare

<400> SEQUENCE: 70

| | |
|---|---|
| gttggcctac gtacacaagc tt | 22 |

<210> SEQ ID NO 71
<211> LENGTH: 22
<212> TYPE: DNA
<213> ORGANISM: Arabidopsis thaliana

<400> SEQUENCE: 71

| | |
|---|---|
| gttggccgac atacatttgt tt | 22 |

<210> SEQ ID NO 72
<211> LENGTH: 22
<212> TYPE: DNA
<213> ORGANISM: Hordeum vulgare

<400> SEQUENCE: 72

| | |
|---|---|
| ccggggacac gtacaccacc tc | 22 |

<210> SEQ ID NO 73
<211> LENGTH: 22
<212> TYPE: DNA
<213> ORGANISM: Brassica napus

<400> SEQUENCE: 73

| | |
|---|---|
| gttggccgac gtatactttt gt | 22 |

<210> SEQ ID NO 74
<211> LENGTH: 22
<212> TYPE: DNA
<213> ORGANISM: Zea mays

<400> SEQUENCE: 74

| | |
|---|---|
| gttggcgcac gtaataatcc tt | 22 |

<210> SEQ ID NO 75
<211> LENGTH: 22
<212> TYPE: DNA
<213> ORGANISM: Zea mays

<400> SEQUENCE: 75

| | |
|---|---|
| cccgggagac gttcgaaacc tt | 22 |

<210> SEQ ID NO 76
<211> LENGTH: 22
<212> TYPE: DNA
<213> ORGANISM: Triticum aestivum

<400> SEQUENCE: 76

| | |
|---|---|
| gcgggtatac gtacgtcggc ct | 22 |

<210> SEQ ID NO 77
<211> LENGTH: 22
<212> TYPE: DNA
<213> ORGANISM: Arabidopsis thaliana

<400> SEQUENCE: 77

-continued

```
tcaagccgac acagacacgc gt                                    22

<210> SEQ ID NO 78
<211> LENGTH: 15
<212> TYPE: DNA
<213> ORGANISM: Artificial
<220> FEATURE:
<223> OTHER INFORMATION: consensus motif

<400> SEQUENCE: 78
ggccatacac cccta                                            15

<210> SEQ ID NO 79
<211> LENGTH: 15
<212> TYPE: DNA
<213> ORGANISM: Triticum aestivum

<400> SEQUENCE: 79
ggccatgcag ccctt                                            15

<210> SEQ ID NO 80
<211> LENGTH: 15
<212> TYPE: DNA
<213> ORGANISM: Triticum aestivum

<400> SEQUENCE: 80
ggcccggccc ccta                                             15

<210> SEQ ID NO 81
<211> LENGTH: 15
<212> TYPE: DNA
<213> ORGANISM: Hordeum vulgare

<400> SEQUENCE: 81
gcccatacac cccta                                            15

<210> SEQ ID NO 82
<211> LENGTH: 15
<212> TYPE: DNA
<213> ORGANISM: Triticum aestivum

<400> SEQUENCE: 82
ggccattctg ccctt                                            15

<210> SEQ ID NO 83
<211> LENGTH: 15
<212> TYPE: DNA
<213> ORGANISM: Hordeum vulgare

<400> SEQUENCE: 83
gccccgacac cgcta                                            15

<210> SEQ ID NO 84
<211> LENGTH: 15
<212> TYPE: DNA
<213> ORGANISM: Zea mays

<400> SEQUENCE: 84
ggtcctcctg ccctt                                            15

<210> SEQ ID NO 85
<211> LENGTH: 28
<212> TYPE: DNA
```

```
<213> ORGANISM: Artificial
<220> FEATURE:
<223> OTHER INFORMATION: consensus motif

<400> SEQUENCE: 85
ctcgctattg tgacgggtca gatcgagc                                          28

<210> SEQ ID NO 86
<211> LENGTH: 28
<212> TYPE: DNA
<213> ORGANISM: Zea mays

<400> SEQUENCE: 86
ctcgctcggg tgtcgggtca gatcgatc                                          28

<210> SEQ ID NO 87
<211> LENGTH: 28
<212> TYPE: DNA
<213> ORGANISM: Zea mays

<400> SEQUENCE: 87
ctcgttatag taacgagtca taacgagc                                          28

<210> SEQ ID NO 88
<211> LENGTH: 28
<212> TYPE: DNA
<213> ORGANISM: Triticum aestivum

<400> SEQUENCE: 88
ctccccactg tttgggatca gttcgcgc                                          28

<210> SEQ ID NO 89
<211> LENGTH: 28
<212> TYPE: DNA
<213> ORGANISM: Hordeum vulgare

<400> SEQUENCE: 89 atagttttt tgaggggtca atgcgacc                                           28

<210> SEQ ID NO 90
<211> LENGTH: 26
<212> TYPE: DNA
<213> ORGANISM: Artificial
<220> FEATURE:
<223> OTHER INFORMATION: consensus motif

<400> SEQUENCE: 90
gggtcaaaac gatccatttg gaagac                                            26

<210> SEQ ID NO 91
<211> LENGTH: 26
<212> TYPE: DNA
<213> ORGANISM: Zea mays

<400> SEQUENCE: 91
gggtcagatc gatccagttg gcgcac                                            26

<210> SEQ ID NO 92
<211> LENGTH: 26
<212> TYPE: DNA
<213> ORGANISM: Hordeum vulgare

<400> SEQUENCE: 92
ggatcagaag gatccaattc gaagac                                            26
```

<210> SEQ ID NO 93
<211> LENGTH: 26
<212> TYPE: DNA
<213> ORGANISM: Hordeum vulgare

<400> SEQUENCE: 93
gggtcaatgc gaccaatttg gaagcc								26

<210> SEQ ID NO 94
<211> LENGTH: 26
<212> TYPE: DNA
<213> ORGANISM: Zea mays

<400> SEQUENCE: 94
gggtccaccg gatttattgg cagtac								26

<210> SEQ ID NO 95
<211> LENGTH: 14
<212> TYPE: DNA
<213> ORGANISM: Artificial
<220> FEATURE:
<223> OTHER INFORMATION: consesnsus motif

<400> SEQUENCE: 95
ttcgacctgc atgc								14

<210> SEQ ID NO 96
<211> LENGTH: 14
<212> TYPE: DNA
<213> ORGANISM: Triticum aestivum

<400> SEQUENCE: 96
gtcgacctgc aggc								14

<210> SEQ ID NO 97
<211> LENGTH: 14
<212> TYPE: DNA
<213> ORGANISM: Hordeum vulgare

<400> SEQUENCE: 97
gtcgacctgc aggc								14

<210> SEQ ID NO 98
<211> LENGTH: 14
<212> TYPE: DNA
<213> ORGANISM: Zea mays

<400> SEQUENCE: 98
ttccacctgc atgc								14

<210> SEQ ID NO 99
<211> LENGTH: 14
<212> TYPE: DNA
<213> ORGANISM: Hordeum vulgare

<400> SEQUENCE: 99
tgccacatgc atgg								14

<210> SEQ ID NO 100
<211> LENGTH: 14
<212> TYPE: DNA
<213> ORGANISM: Zea mays

```
<400> SEQUENCE: 100
tccgagctgc aagg                                                        14

<210> SEQ ID NO 101
<211> LENGTH: 14
<212> TYPE: DNA
<213> ORGANISM: Hordeum vulgare

<400> SEQUENCE: 101
tgcgacatgc atag                                                        14

<210> SEQ ID NO 102
<211> LENGTH: 14
<212> TYPE: DNA
<213> ORGANISM: Zea mays

<400> SEQUENCE: 102
ttcgatctgc gagc                                                        14

<210> SEQ ID NO 103
<211> LENGTH: 21
<212> TYPE: DNA
<213> ORGANISM: Artificial
<220> FEATURE:
<223> OTHER INFORMATION: consensus motif

<400> SEQUENCE: 103
gtcagcaggc accagcccat c                                                21

<210> SEQ ID NO 104
<211> LENGTH: 21
<212> TYPE: DNA
<213> ORGANISM: Triticum aestivum

<400> SEQUENCE: 104
gtcggcactc acctgcccat c                                                21

<210> SEQ ID NO 105
<211> LENGTH: 21
<212> TYPE: DNA
<213> ORGANISM: Triticum aestivum

<400> SEQUENCE: 105
gtcagcagcc acctgccgac c                                                21

<210> SEQ ID NO 106
<211> LENGTH: 21
<212> TYPE: DNA
<213> ORGANISM: Zea mays

<400> SEQUENCE: 106
gtcagcgggc cccacctcat c                                                21

<210> SEQ ID NO 107
<211> LENGTH: 21
<212> TYPE: DNA
<213> ORGANISM: Zea mays

<400> SEQUENCE: 107
gcccacaggc cacagcgcat c                                                21

<210> SEQ ID NO 108
<211> LENGTH: 47
```

```
<212> TYPE: DNA
<213> ORGANISM: Artificial
<220> FEATURE:
<223> OTHER INFORMATION: consensus motif

<400> SEQUENCE: 108
catcaaaagg agtacacgtg aaataaggag aacgacccga aactcgg          47

<210> SEQ ID NO 109
<211> LENGTH: 47
<212> TYPE: DNA
<213> ORGANISM: Brassica napus

<400> SEQUENCE: 109
caacaaaggt ggtacacgtg aagtaacgat aacgacccac aactccg          47

<210> SEQ ID NO 110
<211> LENGTH: 47
<212> TYPE: DNA
<213> ORGANISM: Arabidopsis thaliana

<400> SEQUENCE: 110
cacaaatatg attacacgtg gcctgaaaag aacgaacaga aactcgg          47

<210> SEQ ID NO 111
<211> LENGTH: 47
<212> TYPE: DNA
<213> ORGANISM: Zea mays

<400> SEQUENCE: 111
gatcattctg agcatttgca gaaaaggag aacgtcccga aatcctg           47

<210> SEQ ID NO 112
<211> LENGTH: 46
<212> TYPE: DNA
<213> ORGANISM: Hordeum vulgare

<400> SEQUENCE: 112 attaaaggg gtatctgaga ctcaaggaag aagtccctat gggagg            46

<210> SEQ ID NO 113
<211> LENGTH: 29
<212> TYPE: DNA
<213> ORGANISM: Artificial
<220> FEATURE:
<223> OTHER INFORMATION: consensus motif

<400> SEQUENCE: 113 gaaaggtga attgacagga cactgcagg                                29

<210> SEQ ID NO 114
<211> LENGTH: 29
<212> TYPE: DNA
<213> ORGANISM: Zea mays

<400> SEQUENCE: 114
gagaaggtgt attcacagta cagtgcagg                               29

<210> SEQ ID NO 115
<211> LENGTH: 29
<212> TYPE: DNA
<213> ORGANISM: Arabidopsis thaliana

<400> SEQUENCE: 115
```

```
gaaaaggtga attaagagga gagaggagg                                  29

<210> SEQ ID NO 116
<211> LENGTH: 29
<212> TYPE: DNA
<213> ORGANISM: Zea mays

<400> SEQUENCE: 116
gaggaggacg agtgggaggg cacttctgg                                  29

<210> SEQ ID NO 117
<211> LENGTH: 29
<212> TYPE: DNA
<213> ORGANISM: Zea mays

<400> SEQUENCE: 117
gcagacgtgc acagacaggg caccaccgg                                  29

<210> SEQ ID NO 118
<211> LENGTH: 26
<212> TYPE: DNA
<213> ORGANISM: Artificial
<220> FEATURE:
<223> OTHER INFORMATION: consensus motif

<400> SEQUENCE: 118
acgaattcag gatctggttg tatcga                                     26

<210> SEQ ID NO 119
<211> LENGTH: 26
<212> TYPE: DNA
<213> ORGANISM: Zea mays

<400> SEQUENCE: 119
acgaattctg catctggttc tttcga                                     26

<210> SEQ ID NO 120
<211> LENGTH: 26
<212> TYPE: DNA
<213> ORGANISM: Hordeum vulgare

<400> SEQUENCE: 120
aagaattcag gatctggttg cattga                                     26

<210> SEQ ID NO 121
<211> LENGTH: 26
<212> TYPE: DNA
<213> ORGANISM: Hordeum vulgare

<400> SEQUENCE: 121
acgatttgag gatctcgatg tgccga                                     26

<210> SEQ ID NO 122
<211> LENGTH: 20
<212> TYPE: DNA
<213> ORGANISM: Artificial
<220> FEATURE:
<223> OTHER INFORMATION: consesus motif

<400> SEQUENCE: 122
tcttggagcc ggtccctctg                                            20

<210> SEQ ID NO 123
<211> LENGTH: 20
```

```
<212> TYPE: DNA
<213> ORGANISM: Zea mays

<400> SEQUENCE: 123
tcttggtgcc gctgcctctg                                                    20

<210> SEQ ID NO 124
<211> LENGTH: 20
<212> TYPE: DNA
<213> ORGANISM: Zea mays

<400> SEQUENCE: 124
tcttgcagcc ggcccctctg                                                    20

<210> SEQ ID NO 125
<211> LENGTH: 20
<212> TYPE: DNA
<213> ORGANISM: Zea mays

<400> SEQUENCE: 125
ttttggtggc ggggtccctg                                                    20

<210> SEQ ID NO 126
<211> LENGTH: 20
<212> TYPE: DNA
<213> ORGANISM: Brassica napus

<400> SEQUENCE: 126
tctttgagcc ggtcctgatg                                                    20

<210> SEQ ID NO 127
<211> LENGTH: 14
<212> TYPE: DNA
<213> ORGANISM: Artificial
<220> FEATURE:
<223> OTHER INFORMATION: consensnsus motif

<400> SEQUENCE: 127
gttggaagag aata                                                          14

<210> SEQ ID NO 128
<211> LENGTH: 14
<212> TYPE: DNA
<213> ORGANISM: Zea mays

<400> SEQUENCE: 128
gttggaagag aata                                                          14

<210> SEQ ID NO 129
<211> LENGTH: 14
<212> TYPE: DNA
<213> ORGANISM: Hordeum vulgare

<400> SEQUENCE: 129
gtttgaagag aata                                                          14

<210> SEQ ID NO 130
<211> LENGTH: 14
<212> TYPE: DNA
<213> ORGANISM: Artificial
<220> FEATURE:
<223> OTHER INFORMATION: consensnsus motif

<400> SEQUENCE: 130
```

```
tcgggccgtt cacg                                                    14

<210> SEQ ID NO 131
<211> LENGTH: 14
<212> TYPE: DNA
<213> ORGANISM: Triticum aestivum

<400> SEQUENCE: 131
tcgggccgtt cacg                                                    14

<210> SEQ ID NO 132
<211> LENGTH: 14
<212> TYPE: DNA
<213> ORGANISM: Triticum aestivum

<400> SEQUENCE: 132
tcgggccgtt cacg                                                    14

<210> SEQ ID NO 133
<211> LENGTH: 14
<212> TYPE: DNA
<213> ORGANISM: Zea mays

<400> SEQUENCE: 133
tcagtccgtg cagg                                                    14

<210> SEQ ID NO 134
<211> LENGTH: 13
<212> TYPE: DNA
<213> ORGANISM: Artificial
<220> FEATURE:
<223> OTHER INFORMATION: consesnsus primer

<400> SEQUENCE: 134
ggagacacac cgc                                                     13

<210> SEQ ID NO 135
<211> LENGTH: 13
<212> TYPE: DNA
<213> ORGANISM: Zea mays

<400> SEQUENCE: 135
ggcgacacac cgc                                                     13

<210> SEQ ID NO 136
<211> LENGTH: 13
<212> TYPE: DNA
<213> ORGANISM: Hordeum vulgare

<400> SEQUENCE: 136
ggagacacac ctc                                                     13

<210> SEQ ID NO 137
<211> LENGTH: 15
<212> TYPE: DNA
<213> ORGANISM: Artificial
<220> FEATURE:
<223> OTHER INFORMATION: consensus primer

<400> SEQUENCE: 137
gttggccgac ataca                                                   15

<210> SEQ ID NO 138
<211> LENGTH: 15
```

```
<212> TYPE: DNA
<213> ORGANISM: Arabidopsis thaliana

<400> SEQUENCE: 138
gttggccgac ataca                                                    15

<210> SEQ ID NO 139
<211> LENGTH: 15
<212> TYPE: DNA
<213> ORGANISM: Hordeum vulgare

<400> SEQUENCE: 139
gttggcctac gtaca                                                    15

<210> SEQ ID NO 140
<211> LENGTH: 15
<212> TYPE: DNA
<213> ORGANISM: Brassica napus

<400> SEQUENCE: 140
gttggccgac gtata                                                    15

<210> SEQ ID NO 141
<211> LENGTH: 15
<212> TYPE: DNA
<213> ORGANISM: Zea mays

<400> SEQUENCE: 141
gctgtcctac acaca                                                    15

<210> SEQ ID NO 142
<211> LENGTH: 15
<212> TYPE: DNA
<213> ORGANISM: Artificial
<220> FEATURE:
<223> OTHER INFORMATION: consensus motif

<400> SEQUENCE: 142
ggtggttgga gtgtg                                                    15

<210> SEQ ID NO 143
<211> LENGTH: 15
<212> TYPE: DNA
<213> ORGANISM: Hordeum vulgare

<400> SEQUENCE: 143
ggtggttgga gtgtg                                                    15

<210> SEQ ID NO 144
<211> LENGTH: 15
<212> TYPE: DNA
<213> ORGANISM: Zea mays

<400> SEQUENCE: 144
ggtggttgta ttgtg                                                    15

<210> SEQ ID NO 145
<211> LENGTH: 14
<212> TYPE: DNA
<213> ORGANISM: Artificial
<220> FEATURE:
<223> OTHER INFORMATION: consensus motif

<400> SEQUENCE: 145
```

-continued

```
gttggaagag aata                                                    14

<210> SEQ ID NO 146
<211> LENGTH: 14
<212> TYPE: DNA
<213> ORGANISM: Zea mays

<400> SEQUENCE: 146
gttggaagag aata                                                    14

<210> SEQ ID NO 147
<211> LENGTH: 14
<212> TYPE: DNA
<213> ORGANISM: Hordeum vulgare

<400> SEQUENCE: 147
gtttgaagag aata                                                    14

<210> SEQ ID NO 148
<211> LENGTH: 17
<212> TYPE: DNA
<213> ORGANISM: Artificial
<220> FEATURE:
<223> OTHER INFORMATION: consensus motif

<400> SEQUENCE: 148
agcagccacc ggccaac                                                 17

<210> SEQ ID NO 149
<211> LENGTH: 17
<212> TYPE: DNA
<213> ORGANISM: Triticum aestivum

<400> SEQUENCE: 149
agcagccacc tgccgac                                                 17

<210> SEQ ID NO 150
<211> LENGTH: 17
<212> TYPE: DNA
<213> ORGANISM: Zea mays

<400> SEQUENCE: 150
agccgccccc gggagac                                                 17

<210> SEQ ID NO 151
<211> LENGTH: 17
<212> TYPE: DNA
<213> ORGANISM: Hordeum vulgare

<400> SEQUENCE: 151
acacgccacc agcaaac                                                 17

<210> SEQ ID NO 152
<211> LENGTH: 17
<212> TYPE: DNA
<213> ORGANISM: Zea mays

<400> SEQUENCE: 152
agcagccgcc gatcaac                                                 17

<210> SEQ ID NO 153
<211> LENGTH: 17
<212> TYPE: DNA
<213> ORGANISM: Hordeum vulgare
```

```
<400> SEQUENCE: 153
agagccctcc tgccagc                                              17

<210> SEQ ID NO 154
<211> LENGTH: 15
<212> TYPE: DNA
<213> ORGANISM: Artificial
<220> FEATURE:
<223> OTHER INFORMATION: consensus motif

<400> SEQUENCE: 154
tggccattca gccct                                                15

<210> SEQ ID NO 155
<211> LENGTH: 15
<212> TYPE: DNA
<213> ORGANISM: Zea mays

<400> SEQUENCE: 155
tggccatgca gccct                                                15

<210> SEQ ID NO 156
<211> LENGTH: 15
<212> TYPE: DNA
<213> ORGANISM: Triticum aestivum

<400> SEQUENCE: 156
tggccattct gccct                                                15

<210> SEQ ID NO 157
<211> LENGTH: 15
<212> TYPE: DNA
<213> ORGANISM: Hordeum vulgare

<400> SEQUENCE: 157
tcactattca gcgct                                                15

<210> SEQ ID NO 158
<211> LENGTH: 15
<212> TYPE: DNA
<213> ORGANISM: Zea mays

<400> SEQUENCE: 158
tcgatatcca cccct                                                15

<210> SEQ ID NO 159
<211> LENGTH: 15
<212> TYPE: DNA
<213> ORGANISM: Hordeum vulgare

<400> SEQUENCE: 159
agcccataca cccct                                                15

<210> SEQ ID NO 160
<211> LENGTH: 16
<212> TYPE: DNA
<213> ORGANISM: Artificial
<220> FEATURE:
<223> OTHER INFORMATION: consensus motif

<400> SEQUENCE: 160
agcgcgcaca ccgtcg                                               16
```

-continued

```
<210> SEQ ID NO 161
<211> LENGTH: 16
<212> TYPE: DNA
<213> ORGANISM: Hordeum vulgare

<400> SEQUENCE: 161
agcgcgcacg tcgtgg                                                  16

<210> SEQ ID NO 162
<211> LENGTH: 16
<212> TYPE: DNA
<213> ORGANISM: Zea mays

<400> SEQUENCE: 162
agggcgcaca ccgtcg                                                  16

<210> SEQ ID NO 163
<211> LENGTH: 21
<212> TYPE: DNA
<213> ORGANISM: artificial
<220> FEATURE:
<223> OTHER INFORMATION: consensus motif

<400> SEQUENCE: 163
accgaggcga gtcgaggcag c                                            21

<210> SEQ ID NO 164
<211> LENGTH: 21
<212> TYPE: DNA
<213> ORGANISM: Hordeum vulgare

<400> SEQUENCE: 164
actgaagcga gtcgagggcg c                                            21

<210> SEQ ID NO 165
<211> LENGTH: 21
<212> TYPE: DNA
<213> ORGANISM: Zea mays

<400> SEQUENCE: 165
aacgagccga gccgagccag c                                            21

<210> SEQ ID NO 166
<211> LENGTH: 21
<212> TYPE: DNA
<213> ORGANISM: Triticum aestivum

<400> SEQUENCE: 166
aacgcggtca gtcgcggcag a                                            21

<210> SEQ ID NO 167
<211> LENGTH: 21
<212> TYPE: DNA
<213> ORGANISM: Zea mays

<400> SEQUENCE: 167
accgaggcga cacaccgcag c                                            21

<210> SEQ ID NO 168
<211> LENGTH: 21
<212> TYPE: DNA
<213> ORGANISM: Hordeum vulgare

<400> SEQUENCE: 168
```

```
gctacgtgga gtgcaggtgg c                                              21

<210> SEQ ID NO 169
<211> LENGTH: 25
<212> TYPE: DNA
<213> ORGANISM: Artificial
<220> FEATURE:
<223> OTHER INFORMATION: consesnus primer

<400> SEQUENCE: 169
ccccgagctc cgacgaagct catcg                                          25

<210> SEQ ID NO 170
<211> LENGTH: 25
<212> TYPE: DNA
<213> ORGANISM: zea mays

<400> SEQUENCE: 170
cccccagctc ggacggagct cctcg                                          25

<210> SEQ ID NO 171
<211> LENGTH: 25
<212> TYPE: DNA
<213> ORGANISM: Zea mays

<400> SEQUENCE: 171
cgccgtgctc cgatgaagct gagcg                                          25

<210> SEQ ID NO 172
<211> LENGTH: 25
<212> TYPE: DNA
<213> ORGANISM: Zea mays

<400> SEQUENCE: 172
ctccgagctg caaggccgct cgtcg                                          25

<210> SEQ ID NO 173
<211> LENGTH: 17
<212> TYPE: DNA
<213> ORGANISM: Artificial
<220> FEATURE:
<223> OTHER INFORMATION: consensus motif

<400> SEQUENCE: 173
gccccatggg actaggg                                                   17

<210> SEQ ID NO 174
<211> LENGTH: 17
<212> TYPE: DNA
<213> ORGANISM: Zea mays

<400> SEQUENCE: 174
gctcgctggg agtaggg                                                   17

<210> SEQ ID NO 175
<211> LENGTH: 17
<212> TYPE: DNA
<213> ORGANISM: Hordeum vulgare

<400> SEQUENCE: 175
gccccatggt cctaggg                                                   17

<210> SEQ ID NO 176
```

```
<211> LENGTH: 28
<212> TYPE: DNA
<213> ORGANISM: Artificial
<220> FEATURE:
<223> OTHER INFORMATION: consensus motif

<400> SEQUENCE: 176
agctgagcgt gatcagcagc cgccgctc                                              28

<210> SEQ ID NO 177
<211> LENGTH: 28
<212> TYPE: DNA
<213> ORGANISM: Zea mays

<400> SEQUENCE: 177
agtcgaaccc ctcctccccg tccaatcc                                              28

<210> SEQ ID NO 178
<211> LENGTH: 28
<212> TYPE: DNA
<213> ORGANISM: Zea mays

<400> SEQUENCE: 178
acaacacacc ctcctcgtcc tccaatcc                                              28

<210> SEQ ID NO 179
<211> LENGTH: 28
<212> TYPE: DNA
<213> ORGANISM: Triticum aestivum

<400> SEQUENCE: 179
agtcggcact cacctgccca tccactca                                              28

<210> SEQ ID NO 180
<211> LENGTH: 28
<212> TYPE: DNA
<213> ORGANISM: Zea mays

<400> SEQUENCE: 180
agaatatgcc gtcccagccc accatccc                                              28

<210> SEQ ID NO 181
<211> LENGTH: 28
<212> TYPE: DNA
<213> ORGANISM: Hordeum vulgare

<400> SEQUENCE: 181
aaacagagcc ctcctgccag cccttgcc                                              28

<210> SEQ ID NO 182
<211> LENGTH: 28
<212> TYPE: DNA
<213> ORGANISM: Zea mays

<400> SEQUENCE: 182
acccctagct gtcaccgtcg cccagtcc                                              28

<210> SEQ ID NO 183
<211> LENGTH: 28
<212> TYPE: DNA
<213> ORGANISM: Hordeum vulgare

<400> SEQUENCE: 183
aggcggtaca gtcctggcca atatgacc                                              28
```

```
<210> SEQ ID NO 184
<211> LENGTH: 14
<212> TYPE: DNA
<213> ORGANISM: Artificial
<220> FEATURE:
<223> OTHER INFORMATION: consensus motif

<400> SEQUENCE: 184
aaagggccgc gcga                                                       14

<210> SEQ ID NO 185
<211> LENGTH: 14
<212> TYPE: DNA
<213> ORGANISM: Hordeum vulgare

<400> SEQUENCE: 185
aaagggccgt gcga                                                       14

<210> SEQ ID NO 186
<211> LENGTH: 14
<212> TYPE: DNA
<213> ORGANISM: Zea mays

<400> SEQUENCE: 186
aaagggtcgc gtga                                                       14

<210> SEQ ID NO 187
<211> LENGTH: 20
<212> TYPE: DNA
<213> ORGANISM: Artificial
<220> FEATURE:
<223> OTHER INFORMATION: consensus motif

<400> SEQUENCE: 187
tcttgcagcc gccccctctg                                                 20

<210> SEQ ID NO 188
<211> LENGTH: 20
<212> TYPE: DNA
<213> ORGANISM: Zea mays

<400> SEQUENCE: 188
tcttggtgcc gctgcctctg                                                 20

<210> SEQ ID NO 189
<211> LENGTH: 20
<212> TYPE: DNA
<213> ORGANISM: Zea mays

<400> SEQUENCE: 189
tcttgcagcc ggcccctctg                                                 20

<210> SEQ ID NO 190
<211> LENGTH: 21
<212> TYPE: DNA
<213> ORGANISM: Artificial
<220> FEATURE:
<223> OTHER INFORMATION: consensus motif

<400> SEQUENCE: 190
gaaagaattc agcatctggt t                                               21

<210> SEQ ID NO 191
```

```
<211> LENGTH: 21
<212> TYPE: DNA
<213> ORGANISM: Zea mays

<400> SEQUENCE: 191
gcacgaattc tgcatctggt t                                              21

<210> SEQ ID NO 192
<211> LENGTH: 21
<212> TYPE: DNA
<213> ORGANISM: Hordeum vulgare

<400> SEQUENCE: 192
gaaagaattc aggatctggt t                                              21

<210> SEQ ID NO 193
<211> LENGTH: 15
<212> TYPE: DNA
<213> ORGANISM: Artificial
<220> FEATURE:
<223> OTHER INFORMATION: consensus motif

<400> SEQUENCE: 193
ttcccggaca agggg                                                     15

<210> SEQ ID NO 194
<211> LENGTH: 15
<212> TYPE: DNA
<213> ORGANISM: Triticum aestivum

<400> SEQUENCE: 194
ttcccggaca aggag                                                     15

<210> SEQ ID NO 195
<211> LENGTH: 15
<212> TYPE: DNA
<213> ORGANISM: Zea mays

<400> SEQUENCE: 195
ttcccggacc gtggg                                                     15

<210> SEQ ID NO 196
<211> LENGTH: 15
<212> TYPE: DNA
<213> ORGANISM: Triticum aestivum

<400> SEQUENCE: 196
ttcccggacc gtggg                                                     15

<210> SEQ ID NO 197
<211> LENGTH: 15
<212> TYPE: DNA
<213> ORGANISM: Artificial
<220> FEATURE:
<223> OTHER INFORMATION: consensus motif

<400> SEQUENCE: 197
atggccatac agccc                                                     15

<210> SEQ ID NO 198
<211> LENGTH: 15
<212> TYPE: DNA
<213> ORGANISM: Zea mays

<400> SEQUENCE: 198
```

-continued

```
atggccatgc agccc                                                      15

<210> SEQ ID NO 199
<211> LENGTH: 15
<212> TYPE: DNA
<213> ORGANISM: Triticum aestivum

<400> SEQUENCE: 199
atggccattc tgccc                                                      15

<210> SEQ ID NO 200
<211> LENGTH: 15
<212> TYPE: DNA
<213> ORGANISM: Hordeum vulgare

<400> SEQUENCE: 200
aagcccatac acccc                                                      15

<210> SEQ ID NO 201
<211> LENGTH: 14
<212> TYPE: DNA
<213> ORGANISM: Artificial
<220> FEATURE:
<223> OTHER INFORMATION: consensus motif

<400> SEQUENCE: 201
ttcgacctgc aggc                                                       14

<210> SEQ ID NO 202
<211> LENGTH: 14
<212> TYPE: DNA
<213> ORGANISM: Triticum aestivum

<400> SEQUENCE: 202
gtcgacctgc aggc                                                       14

<210> SEQ ID NO 203
<211> LENGTH: 14
<212> TYPE: DNA
<213> ORGANISM: Hordeum vulgare

<400> SEQUENCE: 203
gtcgacctgc aggc                                                       14

<210> SEQ ID NO 204
<211> LENGTH: 14
<212> TYPE: DNA
<213> ORGANISM: Zea mays

<400> SEQUENCE: 204
ttccacctgc atgc                                                       14

<210> SEQ ID NO 205
<211> LENGTH: 14
<212> TYPE: DNA
<213> ORGANISM: Zea mays

<400> SEQUENCE: 205
ttcgatctgc gagc                                                       14

<210> SEQ ID NO 206
<211> LENGTH: 14
<212> TYPE: DNA
```

<213> ORGANISM: Hordeum vulgare

<400> SEQUENCE: 206
tgccacatgc atgg 14

<210> SEQ ID NO 207
<211> LENGTH: 15
<212> TYPE: DNA
<213> ORGANISM: Artificial
<220> FEATURE:
<223> OTHER INFORMATION: consensus motif

<400> SEQUENCE: 207
agcagcacag acgcg 15

<210> SEQ ID NO 208
<211> LENGTH: 15
<212> TYPE: DNA
<213> ORGANISM: Zea mays

<400> SEQUENCE: 208
agcagtacag acgcg 15

<210> SEQ ID NO 209
<211> LENGTH: 15
<212> TYPE: DNA
<213> ORGANISM: Hordeum vulgare

<400> SEQUENCE: 209
agcagcacag tcgtg 15

<210> SEQ ID NO 210
<211> LENGTH: 14
<212> TYPE: DNA
<213> ORGANISM: Artificial
<220> FEATURE:
<223> OTHER INFORMATION: consensus motif

<400> SEQUENCE: 210
ccattctcgt cccc 14

<210> SEQ ID NO 211
<211> LENGTH: 14
<212> TYPE: DNA
<213> ORGANISM: Zea mays

<400> SEQUENCE: 211
ccattctcgt cctc 14

<210> SEQ ID NO 212
<211> LENGTH: 14
<212> TYPE: DNA
<213> ORGANISM: Zea mays

<400> SEQUENCE: 212
ccctcctcgt cctc 14

<210> SEQ ID NO 213
<211> LENGTH: 14
<212> TYPE: DNA
<213> ORGANISM: Hordeum vulgare

<400> SEQUENCE: 213 ccctttttagt ccca 14

<210> SEQ ID NO 214
<211> LENGTH: 14
<212> TYPE: DNA
<213> ORGANISM: Triticum aestivum

<400> SEQUENCE: 214
ccgttcacgt ccgc                                                    14

<210> SEQ ID NO 215
<211> LENGTH: 14
<212> TYPE: DNA
<213> ORGANISM: Hordeum vulgare

<400> SEQUENCE: 215
ccatcttaat cccc                                                    14

<210> SEQ ID NO 216
<211> LENGTH: 10
<212> TYPE: DNA
<213> ORGANISM: Zea mays

<400> SEQUENCE: 216
ggtgctcttt                                                         10

<210> SEQ ID NO 217
<211> LENGTH: 10
<212> TYPE: DNA
<213> ORGANISM: Zea mays

<400> SEQUENCE: 217 accgccccccc                                                        10

<210> SEQ ID NO 218
<211> LENGTH: 10
<212> TYPE: DNA
<213> ORGANISM: Zea mays

<400> SEQUENCE: 218
ggtgcaccct                                                         10

<210> SEQ ID NO 219
<211> LENGTH: 10
<212> TYPE: DNA
<213> ORGANISM: Zea mays

<400> SEQUENCE: 219
ggtgccttgt                                                         10

<210> SEQ ID NO 220
<211> LENGTH: 10
<212> TYPE: DNA
<213> ORGANISM: Zea mays

<400> SEQUENCE: 220
ggtgctctgt                                                         10

<210> SEQ ID NO 221
<211> LENGTH: 10
<212> TYPE: DNA
<213> ORGANISM: Zea mays

<400> SEQUENCE: 221
ggtgctgccc 10

<210> SEQ ID NO 222
<211> LENGTH: 10
<212> TYPE: DNA
<213> ORGANISM: Zea mays

<400> SEQUENCE: 222
ggtgctgccc 10

<210> SEQ ID NO 223
<211> LENGTH: 9
<212> TYPE: DNA
<213> ORGANISM: Zea mays

<400> SEQUENCE: 223 ggcgccacc 9

<210> SEQ ID NO 224
<211> LENGTH: 10
<212> TYPE: DNA
<213> ORGANISM: Zea mays

<400> SEQUENCE: 224
ggtggggcta 10

<210> SEQ ID NO 225
<211> LENGTH: 10
<212> TYPE: DNA
<213> ORGANISM: Zea mays

<400> SEQUENCE: 225
agcgccgccc 10

<210> SEQ ID NO 226
<211> LENGTH: 10
<212> TYPE: DNA
<213> ORGANISM: Zea mays

<400> SEQUENCE: 226
accgccaccc 10

<210> SEQ ID NO 227
<211> LENGTH: 10
<212> TYPE: DNA
<213> ORGANISM: Zea mays

<400> SEQUENCE: 227
ggcgccaccc 10

<210> SEQ ID NO 228
<211> LENGTH: 11
<212> TYPE: DNA
<213> ORGANISM: Zea mays

<400> SEQUENCE: 228
cctcgtgtct c 11

<210> SEQ ID NO 229
<211> LENGTH: 10
<212> TYPE: DNA
<213> ORGANISM: Zea mays

<400> SEQUENCE: 229

```
aaaaaggagc                                                          10

<210> SEQ ID NO 230
<211> LENGTH: 10
<212> TYPE: DNA
<213> ORGANISM: Zea mays

<400> SEQUENCE: 230
aaaaagaagc                                                          10

<210> SEQ ID NO 231
<211> LENGTH: 10
<212> TYPE: DNA
<213> ORGANISM: Zea mays

<400> SEQUENCE: 231
gccacgtcac                                                          10
```